US008552176B2

(12) United States Patent
Thorson et al.

(10) Patent No.: US 8,552,176 B2
(45) Date of Patent: Oct. 8, 2013

(54) GLYCOSYLATED CHLORAMBUCIL ANALOGS AND USES THEREOF

(75) Inventors: Jon S. Thorson, Lexington, KY (US); Randal D. Goff, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 67 days.

(21) Appl. No.: 13/274,814

(22) Filed: Oct. 17, 2011

(65) Prior Publication Data

US 2012/0094946 A1 Apr. 19, 2012

Related U.S. Application Data

(60) Provisional application No. 61/393,674, filed on Oct. 15, 2010.

(51) Int. Cl.
C07H 5/04 (2006.01)
C40B 40/12 (2006.01)
(52) U.S. Cl.
USPC ............... 536/29.1; 506/19; 514/42
(58) Field of Classification Search
USPC ............... 536/29.1; 514/41; 506/19
See application file for complete search history.

(56) References Cited

U.S. PATENT DOCUMENTS

| 6,884,604 | B2 | 4/2005 | Thorson |
| 7,348,309 | B2 | 3/2008 | Thorson |
| 7,754,874 | B2 | 7/2010 | Thorson |
| 2005/0266523 | A1 | 12/2005 | Thorson |
| 2008/0114157 | A1 | 5/2008 | Thorson |
| 2010/0267655 | A1 | 10/2010 | Thorson |

OTHER PUBLICATIONS

Reux et al., Bioorg. Med. Chem., 2008, 16, p. 5004-5020.*
Beyer, et al., J. Med. Chem. 1998, 41, p. 2701-2708.*
Godula, et al., J. Am. Chem. Soc., 2010, 132(29), p. 9963-9965.*
Ahmed, A., et al., "Colchicine glycorandomization influences cytotoxicity and mechanism of action" (2006) J. Am. Chem. Soc. 128, 14224-14225.
Blanchard, S., et al., "Enzymatic tools for engineering natural product glycosylation" (2006) Curr. Opin. Chem. Biol. 10, 263-271.
Carrasco, M. R., et al., "A versatile set of aminooxy amino acids for the synthesis of Neoglycopeptides" (2003) J. Org. Chem. 68, 8853-8858.
Carrasco, M. R., et al., "Synthesis of neoglycopeptides by chemoselective reaction of carbohydrates with peptides containing a novel N'-methyl-aminooxy amino acid" (2002) Tetrahedron Lett. 43, 5727-5729.
Carrasco, M. R., et al., "Synthesis of N-Fmoc-O-(N'-Boc-N'-methyl)-aminohomoserine, an amino acid for the facile preparation of neoglycopeptides" (2003) J. Org. Chem. 68, 195-197.
Griffith, B. R., et al., "Model for antibiotic optimization via neoglycosylation: synthesis of liponeoglycopeptides active against VRE" (2007) J. Am. Chem. Soc. 129, 8150-8155.

Griffith, B. R., et al., "'Sweetening' natural products via glycorandomization" (2005) Curr. Opin. Biotechnol. 16, 622-630.
Iglesias-Guerra, F., et al., "Alkylating agents from sugars: synthesis of chlorambucil derivatives carried by chiral glycosyl glycerols derived from Dglucosamine" (2002) Chirality 14, 199-203.
Kfen, V., et al., "Sweet Antibiotics. The role of glycosidic residues in antibiotic and antitumor activity and their randomization" (2008) FEMS Microbiol. Rev. 32, 858-889.
Langenhan, J. M., et al., "Recent carbohydrate-based chemoselective ligation Applications" (2005) Curr. Org. Syn. 2, 59-81.
Langenhan, J. M., et al., "Enhancing the anticancer properties of cardiac glycosides by neoglycorandomization" (2005) Proc. Nat. Acad. Sci. U.S.A. 102, 12305-12310.
Langenhan, J. M., et al., "Modifying the glycosidic linkage in digitoxin analogs provides selective cytotoxins" (2008) Bioorg. Med. Chem. Lett. 18, 670-673.
Langenhan, J. M., et al., "Neoglycorandomization and chemoenzymatic glycorandomization: two complementary tools for natural product diversification" (2005) J. Nat. Prod. 68, 1696-1711.
Nicotra, F., et al., "Chemoselective neoglycosylation" (2007) Adv. Carbohydr. Chem. Biochem. 61, 353-398.
Peri, F. "Extending chemoselective ligation to sugar chemistry: convergent assembly of bioactive neoglycoconjugates" (2003) Mini-Rev. Med. Chem. 3, 651-658.
Peri, F., et al., "Chemo- and stereoselective glycosylation of hydroxylamino derivatives: a versatile approach to glycoconjugates" (1998) Tetrahedron 54, 12269-12278.
Peri, F., et al., "Chemoselective ligation in glycochemistry" (2004) Chem. Commun. 623-627.
Peri, F., et al., "Solution and solid-phase chemoselective synthesis of (1-6)-amino(methoxy) di- and trisaccharide analogs" (2002) Chem. Commun. 1504-1505.
Peri, F., et al., "Synthesis and conformational analysis of novel N(OCH3)-linked disaccharide analogues" (2004) Chem. Eur. J. 10, 1433-1444.

(Continued)

Primary Examiner — Shaojia Anna Jiang
Assistant Examiner — Jonathan S Lau
(74) Attorney, Agent, or Firm — Quarles & Brady LLP

(57) ABSTRACT

A library of glycosylated chlorambucil analogs which are useful as anti-tumor and/or anti-metastatic agents is disclosed. The glycosylated chlorambucil analogs have the general formula

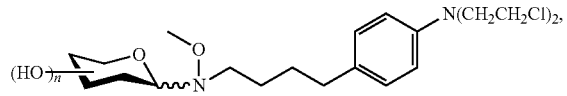

wherein

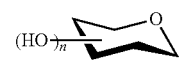

represents a reducing sugar moiety.

17 Claims, 22 Drawing Sheets

(56) References Cited

OTHER PUBLICATIONS

Reux, B., et al., "Synthesis and cytotoxic properties of new fluorodeoxyglucose-coupled chlorambucil derivatives" (2008) Bioorg. Med. Chem. 16, 5004-5020.
Salas, J. A., et al., "Engineering the glycosylation of natural products in Actinomycetes" (2007) Trends Microbiol. 15, 219-232.
Thibodeaux, C. J., et al., "Unusual sugar biosynthesis and natural product glycodiversification" (2007) Nature 446, 1008-1016.
Thorson, J. S., et al., "Nature's carbohydrate chemists: the enzymatic glycosylation of bioactive bacterial metabolites" (2001) Curr. Org. Chem. 5, 139-167.
Weymouth-Wilson, A. C. "The role of carbohydrates in biologically active natural products" (1997) Nat. Prod. Rep. 14, 99-110.

\* cited by examiner

GLYCOSYLATED CHLORAMBUCIL ANALOGS AND USES THEREOF

CROSS-REFERENCE TO RELATED APPLICATIONS

This application claims the benefit of U.S. Provisional Patent Application No. 61/393,647, filed on Oct. 15, 2010, which is incorporated by reference herein in its entirety.

STATEMENT REGARDING FEDERALLY SPONSORED RESEARCH

This invention was made with government support under CA113297 and AI052218 awarded by the National Institutes of Health. The government has certain rights in the invention.

FIELD OF THE INVENTION

This invention relates generally to the synthesis of glycosylated compounds. More particularly, the present invention is directed to glycosylated chlorambucil analogs and their use as therapeutics and as research tools with novel and/or improved bioactivities.

BACKGROUND OF THE INVENTION

The sugars attached to pharmaceutically important natural products dictate the pharmacokinetics and/or pharmacodynamics of the selected agent. Yet, studies designed to systematically understand and/or exploit the attachment of carbohydrates in drug discovery remain limited by the availability of practical synthetic and/or biosynthetic tools. Neoglycosylation takes advantage of a chemoselective reaction between free reducing sugars and N-methoxyamino-substituted acceptors. This reaction has enabled the process of 'neoglycorandomization' wherein alkoxyamine-appended natural product-based drugs are differentially glycosylated with a wide array of natural and unnatural reducing sugars. Neoglycorandomization has led to the discovery of cardenolide neoglycosides with enhanced in vitro and in vivo anticancer activity and lower in vivo toxicity, colchicine neoglycosides with a novel anticancer mechanism and lower in vivo toxicity, vancomycin neoglycosides which displayed improved in vitro potency against clinical isolates of vancomycin-resistant *Enterococci*, and betulinic acid neoglycosides improved for either in vitro anticancer or antiviral potency. While these examples clearly highlight the potential impact of differential glycosylation in drug lead discovery, this work has not addressed the impact of the chemoselective glycosylation 'handles.'

SUMMARY OF THE INVENTION

In a first aspect, the invention encompasses chlorambucil neoglycosides and compositions containing chlorambucil neoglycosides. In some embodiments, this aspect encompasses one or more of the chlorambucil neoglycosides having the general formula

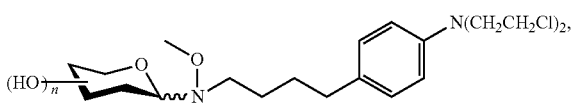

wherein

represents a reducing sugar moiety. Such chlorambucil neoglycosides are tertiary amines, where one of the three moieties attached to the amino nitrogen is a methoxy moiety, the second of the three moieties attached to the amine nitrogen is a chlorambucil analog, and the third of the three moieties attached to the amino nitrogen is a generalized sugar moiety.

In certain such embodiments, the sugar moiety is a reducing sugar selected from an L-sugar, a D-sugar, a deoxy-sugar, a dideoxy-sugar, a glucose epimer, a substituted sugar, a uronic acid, and an oligosaccharide. In some such embodiments, the reducing sugar moiety is selected from the group consisting of D-allose (10), L-allose (11), D-altrose (12), L-altrose (13), D-arabinose (14), L-arabinose (15), 2,3,5-O-tribenzyl-D-arabinose (16), D-cellobiose (17), D-digitoxose (18), D-erythrose (19), D-fucose (20), L-fucose (21), 2,3,4-O-tribenzyl-L-fucose (22), D-galactose (23), L-galactose (24), 2-deoxy-D-galactose (25), D-galacturonose (26), N-acetyl-D-galactose (27), D-glucose (28), L-glucose (29), 2-deoxy-D-glucose (30), 2-fluoro-D-glucose (31), 3-fluoro-D-glucose (32), 3-O-methyl-D-glucose (33), 6-amino-D-glucose (34), 6-N-alloc-D-glucose (35), 6-chloro-D-glucose (36), 6-deoxy-D-glucose (37), D-glucuronose (38), D-glucuronolactone (39), L-gulose (40), D-lyxose (41), L-lyxose (42), D-mannose (43), L-mannose (44), N-acetyl-D-mannose (45), D-Galacto-(1,4)-β-D-Mannose (46), D-melibiose (47), D-MurNAc (48), L-noviose (49), D-olivose (50), L-rhamnose (51), 2,3,4-tri-O-acetyl-L-rhamnose (52), D-ribose (53), L-ribose (54), 2-deoxy-D-ribose (55), 2-deoxy-L-ribose (56), 2,3,5-tri-O-benzyl-D-ribose (57), D-talose (58), L-talose (59), D-threose (60), L-threose (61), D-xylose (62), and L-xylose (63). The numbers in parenthesis are the compound designations used throughout the application. In particular, the designations are used in the structures shown in FIGS. 2A and 2B, and in the reaction schemes and tables presented throughout the application.

Preferably, the reducing sugar moiety is D-arabinose (14), L-arabinose (15), D-glucuronolactone (39), D-threose (60), L-threose (61), D-xylose (62), or L-xylose (63). Of these reducing sugar moieties, D-glucuronolactone (39) and D-threose (60) are more preferred, and D-threose (60) is the most preferred.

In other embodiments, the chlorambucil neoglycoside has the general formula:

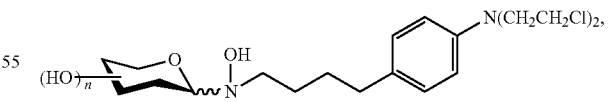

wherein

represents a reducing sugar moiety. Preferably, the reducing sugar moiety is D-fucose (66), D-glucuronolactone (67), or D-ribose (68).

In yet other embodiments, the chlorambucil neoglycoside has the general formula:

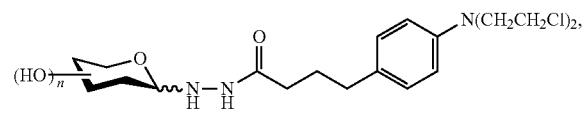

wherein

represents a reducing sugar moiety. Preferably, the reducing sugar moiety is D-fucose (72), D-glucuronolactone (73), D-threose (74), or D-xylose (75).

This aspect additionally encompasses chlorambucil neoglycoside that are produced when an aglycon chlorambucil analog containing a secondary alkoxylamine moiety, a hydroxylamine moiety, or a hydrazine moiety is contacted with a reducing sugar selected from the group consisting of an L-sugar, a D-sugar, a deoxy-sugar, a dideoxy-sugar, a glucose epimer, a substituted sugar, a uronic acid, an oligosaccharide and mixtures thereof. Preferred reducing sugars are selected from the group consisting of D-allose, L-allose, D-altrose, L-altrose, D-arabinose, L-arabinose, 2,3,5-O-tribenzyl-D-arabinose, D-cellobiose, D-digitoxose, D-erythrose, D-fucose, L-fucose, 2,3,4-O-tribenzyl-L-fucose, D-galactose, L-galactose, 2-deoxy-D-galactose, D-galacturonose, N-acetyl-D-galactose, D-glucose, L-glucose, 2-deoxy-D-glucose, 2-fluoro-D-glucose, 3-fluoro-D-glucose, 3-O-methyl-D-glucose, 6-amino-D-glucose, 6-N-alloc-D-glucose, 6-chloro-D-glucose, 6-deoxy-D-glucose, D-glucuronose, D-glucuronolactone, L-gulose, D-lyxose, L-lyxose, D-mannose, L-mannose, N-acetyl-D-mannose, D-Galacto-(1,4)-β-D-Mannose, D-melibiose, D-MurNAc, L-noviose, D-olivose, L-rhamnose, 2,3,4-tri-O-acetyl-L-rhamnose, D-ribose, L-ribose, 2-deoxy-D-ribose, 2-deoxy-L-ribose, 2,3,5-tri-O-benzyl-D-ribose, D-talose, L-talose, D-threose, L-threose, D-xylose, L-xylose; and mixtures thereof.

Preferred aglycon chlorambucil analogs are selected from the group consisting of:

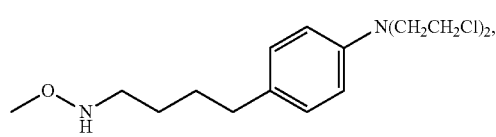

9

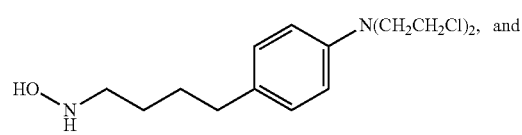

65

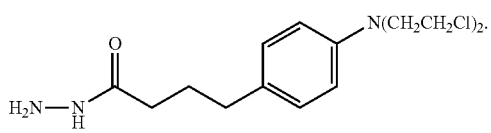

71

This aspect additionally encompasses compositions comprising the chlorambucil neoglycosides described above, as well as pharmaceutically acceptable esters, salts, or prodrugs thereof, combined with a pharmaceutically acceptable carrier. Furthermore, this aspect encompasses a library of chlorambucil neoglycosides comprising two or more of the chlorambucil neoglycosides as described above.

In a second aspect, the invention encompasses methods of treating cancer cells in a subject. The methods comprise the step of contacting the cancer cells with an effective amount of one or more of the chlorambucil neoglycosides described above, whereby the cancer cells are effectively treated. Preferably, the cancer cells are contacted with one or more chlorambucil neoglycosides having the formula:

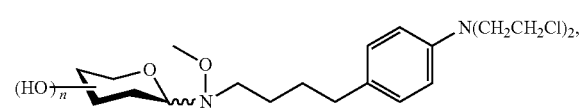

wherein

represents a reducing sugar moiety selected from the group consisting of D-allose (10), D-altrose (12), D-arabinose (14), D-fucose (20), L-fucose (21), 2-deoxy-D-glucose (30), D-glucuronose (38), D-glucuronolactone (39), L-gulose (40), D-lyxose (41), L-lyxose (42), L-ribose (54), 2-deoxy-D-ribose (55), D-threose (60), L-threose (61), D-xylose (62), and L-xylose (63); or a pharmaceutically acceptable ester, salt or prodrug thereof. More preferably, the reducing sugar moiety is D-glucuronolactone (39) or D-threose (60). The most preferred reducing sugar moiety is D-threose (60).

In certain embodiments of the method, the cancer cell types being contacted with an effective amount of the chlorambucil neoglycoside or pharmaceutically acceptable ester, salt or prodrug thereof are human lung cancer cells, human colorectal cancer cells, human liver cancer cells, human breast cancer cells, human ovarian cancer cells, or human central nervous system cancer cells.

In certain embodiments, a pharmaceutically acceptable ester, salt or prodrug of the described chlorambucil neoglycosides is used in the described method of treatment.

Other objects, features and advantages of the present invention will become apparent after review of the specification, claims and drawings.

DETAILED DESCRIPTION OF THE INVENTION

1. Definitions

Figure 1:
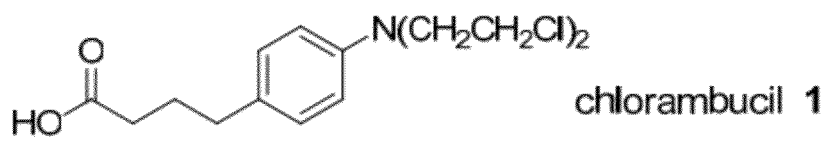
FIG. 1 shows the chemical structure of chlorambucil (1) and other nitrogen mustard compounds including N-oxide 2 (PX-478), FDA-approved bendamustine (3), and glycosylated variants glufosfamide (4) and 5. The latter was found to inhibit the brain/erythrocyte D-glucose GLUT1 transporter and thereby decrease glucose uptake.
Figure 1:
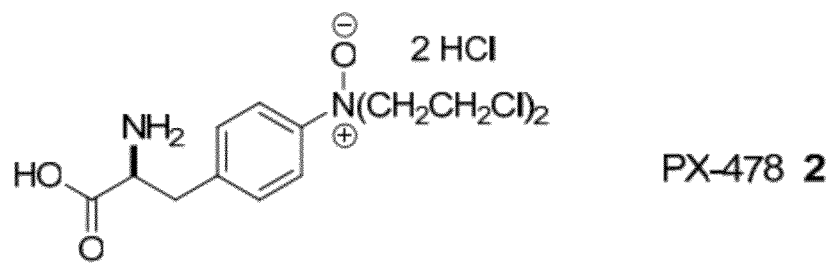
Figure 1:
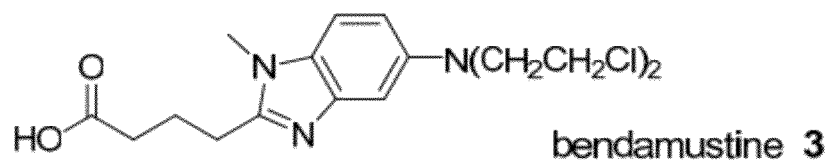
Figure 1:
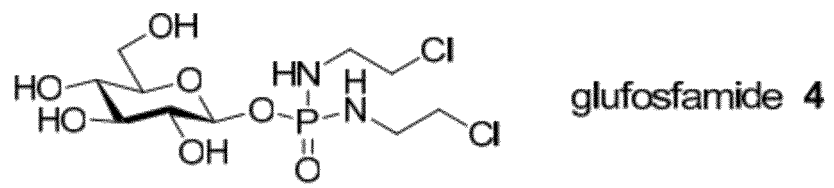
Figure 1:
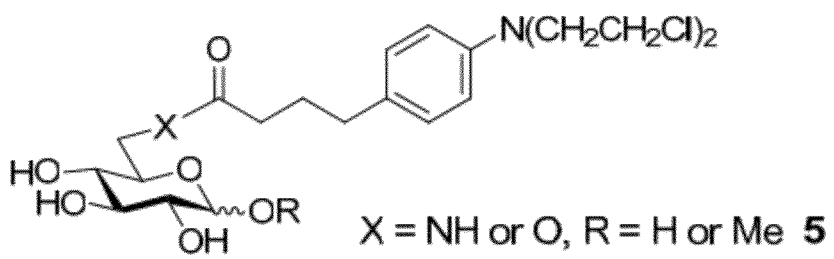

It must be noted that as used herein and in the appended claims, the singular forms "a", "an", and "the" include the plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The following abbreviations are used throughout this application: BH$_3$.Et$_3$N, borane-triethylamine complex; CLL, chronic lymphocytic leukemia; CNS, central nervous system; DIC, N,N' diisopropylcarbodiimide; DMAP, 4-(N',N'-dimethylamino)pyridine; EDAC, 1-ethyl-3-(3 dimethylaminopropyl) carbodiimide; GI50, growth inhibitory concentration for 50% of the cell population under study; GLUT1, glucose transporter 1; LAH, lithium aluminum hydride; NMM, N-methylmorpholine; SAAT1, sodium/amino acid transporter 1; SGLT3, sodium/glucose transporter 3; SPE, solid phase extraction; THF, tetrahydrofuran.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable carrier" as used herein means a chemical composition with which a biologically active ingredient can be combined and which, following the combination, can be used to administer the active ingredient to a subject.

A "pharmaceutically acceptable" ester or salt as used herein means an ester or salt form of the active ingredient which is compatible with any other ingredients of the pharmaceutical composition and which is not deleterious to the subject to which the composition is to be administered. The terms "pharmaceutically acceptable salts" or "prodrugs" includes the salts and prodrugs of compounds that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of the compounds.

"Pro-drug" means a pharmacologically inactive form of a compound which must be metabolized in vivo by a subject after administration into a pharmacologically active form of the compound in order to produce the desired pharmacological effect. After administration to the subject, the pharmacologically inactive form of the compound is converted in vivo under the influence of biological fluids or enzymes into a pharmacologically active form of the compound. Although metabolism occurs for many compounds primarily in the liver, almost all other tissues and organs, especially the lung, are able to carry out varying degrees of metabolism. For example, metabolism of the pro-drug may take place by hydrolysis in blood. Pro-drug forms of compounds may be utilized, for example, to improve bioavailability, mask unpleasant characteristics such as bitter taste, alter solubility for intravenous use, or to provide site-specific delivery of the compound. Reference to a compound herein includes pro-drug forms of a compound.

A discussion of the use of pro-drugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. For example, if a compound contains a carboxylic acid functional group, a pro-drug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino ($C_2$-$C_3$) alkyl.

Similarly, if a compound comprises an alcohol functional group, a pro-drug can be formed by the replacement of the hydrogen atom of the alcohol group with a group such as ($C_1$-$C_6$)alkanoyloxymethyl, 1-($C_1$-$C_6$)alkanoyloxy)ethyl, 1-methyl-1-($C_1$-$C_6$)alkan-oyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a compound comprises an amine functional group, a pro-drug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural alpha-aminoacyl or natural alpha-aminoacyl-, —C(OH)C(O)OY wherein Y is H, ($C_1$-$C_6$)alkyl or benzyl, —C(OY$_0$)Y$_1$ wherein Y$_0$ is ($C_1$-$C_4$)alkyl and Y$_1$ is (($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, —C(Y$_2$)Y$_3$ wherein Y$_2$ is H or methyl and Y$_3$ is mono-N— or di-N,N—($C_1$-$C_6$)-alkylamino, morpholino, piperidin-1-yl or pyrrolidin-1-yl.

"Reducing sugar" means any sugar that contains an aldehyde groups in its open chain form or that is capable of forming aldehyde group in solution through isomerisation. The aldehyde functional group allows the sugar to act as a reducing agent when used in, for example, the Tollens' test or Benedict's test. As the skilled artisan would understand, sugars with ketone groups in their open chain form are capable of isomerizing via a series of tautomeric shifts to produce an aldehyde group in solution. Therefore, ketone-bearing sugars are considered reducing sugars.

The term "salts" refers to inorganic and organic salts of compounds. These salts can be prepared in situ during the final isolation and purification of a compound, or by separately reacting a purified compound with a suitable organic or inorganic acid or base, as appropriate, and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Compounds having N-oxides of amino groups, such as produced by reaction with hydrogen peroxide, are also encompassed.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder.

2. The Invention

As further described in the Example below, the inventors have used a glycorandomization procedure to synthesize a number of novel chlorambucil neoglycosides. Further, the inventors have demonstrated the biological activity of selected novel chlorambucil neoglycosides against certain tumor cell lines.

To assess the impact of alternative chemoselective glycosylation methods in the context of neoglycorandomization, we selected the synthetic anticancer agent chlorambucil (FIG. 1, 1) as a model. First synthesized over five decades ago, chlorambucil remains a current treatment for chronic lymphocytic leukemia (CLL) and has served as the basis for newer generation analogs such as the recently approved bendamustine (3). A nitrogen mustard, 1 leads to guanine alkylation and DNA cross-linking, and ultimately prohibits DNA replication and transcription. The primary cellular uptake mechanism of 1 is passive diffusion and like many cytotoxics, the lack of nitrogen mustard tumor-specificity contributes to serious side effects. Thus, improvements have focused upon (1) the development of tumor-activated prodrugs exemplified by the hypoxia-activated N-oxide PX-478 (FIG. 1, 2) currently in phase I; or (2) modifications to engage tumor-specific transport—exemplified by the β-D-glucosyl analog of ifosfamide (glufosfamide, FIG. 1, 4) which is actively transported into tumor cells by the sodium/D-glucose cotransporter SGLT3 (SAAT1). While the specific glycosylation of 1 has presented analogs which display slight improvements in a perceived therapeutic index (slightly improved in vitro potency and subtle reductions of in vivo peripheral toxicity), the analogs synthesized to date have been restricted to the use of D-gluco or D-galacto-based sugars.

Accordingly, the invention provides in a first aspect one or more of the newly synthesized glycolsylated analogs of chlorambucil. In some embodiments, this aspect encompasses one or more of the chlorambucil neoglycosides having the general formula

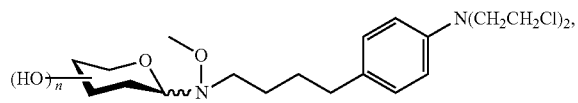

wherein

represents a reducing sugar moiety that is not limited to the specific cyclic structure shown. In certain embodiments, the reducing sugar moiety is a monosaccharide. In such embodiments, the reducing sugar may be a tetrose, a pentose, a hexose, or a deoxy sugar, and n can be 1-6.

The chlorambucil neoglycosides are tertiary amines, where one of the three moieties attached to the amino nitrogen is a methoxy moiety, the second of the three moieties attached to the amine nitrogen is a chlorambucil analog, and the third of the three moieties attached to the amino nitrogen is a generalized sugar moiety, preferably a reducing sugar moiety.

In certain such embodiments, the sugar moeity is a reducing sugar selected from an L-sugar, a D-sugar, a deoxy-sugar, a dideoxy-sugar, a glucose epimer, a substituted sugar, a uronic acid, and an oligosaccharide. The inventors report in the Example below the synthesis of a library of such compounds where the reducing sugar moiety is D-allose (10), L-allose (11), D-altrose (12), L-altrose (13), D-arabinose (14), L-arabinose (15), 2,3,5-O-tribenzyl-D-arabinose (16), D-cellobiose (17), D-digitoxose (18), D-erythrose (19), D-fucose (20), L-fucose (21), 2,3,4-O-tribenzyl-L-fucose (22), D-galactose (23), L-galactose (24), 2-deoxy-D-galactose (25), D-galacturonose (26), N-acetyl-D-galactose (27), D-glucose (28), L-glucose (29), 2-deoxy-D-glucose (30), 2-fluoro-D-glucose (31), 3-fluoro-D-glucose (32), 3-O-methyl-D-glucose (33), 6-amino-D-glucose (34), 6-N-alloc-D-glucose (35), 6-chloro-D-glucose (36), 6-deoxy-D-glucose (37), D-glucuronose (38), D-glucuronolactone (39), L-gulose (40), D-lyxose (41), L-lyxose (42), D-mannose (43), L-mannose (44), N-acetyl-D-mannose (45), D-Galacto-(1,4)-β-D-Mannose (46), D-melibiose (47), D-MurNAc (48), L-noviose (49), D-olivose (50), L-rhamnose (51), 2,3,4-tri-O-acetyl-L-rhamnose (52), D-ribose (53), L-ribose (54), 2-deoxy-D-ribose (55), 2-deoxy-L-ribose (56), 2,3,5-tri-O-benzyl-D-ribose (57), D-talose (58), L-talose (59), D-threose (60), L-threose (61), D-xylose (62), and L-xylose (63).

Based on the bioactivity studies further outlined in the Example below, the chlorambucil neoglycosides where the sugar moiety is D-arabinose (14), L-arabinose (15), D-glucuronolactone (39), D-threose (60), L-threose (61), D-xylose (62), or L-xylose (63) had the greatest bioactivity. Of these reducing sugar moieties, D-glucuronolactone (39) and D-threose (60) are more preferred, and D-threose (60) is the most preferred.

In other embodiments, this aspect includes chlorambucil neoglycosides having the general formula:

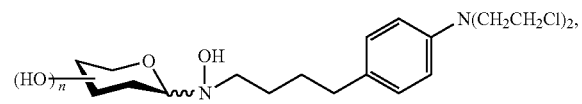

wherein

represents a reducing sugar moiety. In the chlorambucil neoglycoside library reported in the Example below, the reducing sugar moiety is D-fucose (66), D-glucuronolactone (67), or D-ribose (68).

In yet other embodiments, this aspect includes chlorambucil neoglycosides having the general formula:

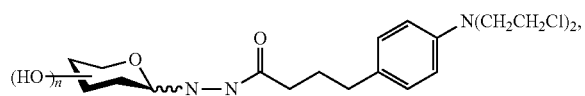

wherein

represents a reducing sugar moiety. In the chlorambucil neoglycoside library reported in the Example below, the reducing sugar moiety is D-fucose (72), D-glucuronolactone (73), D-threose (74), or D-xylose (75).

This aspect additionally encompasses chlorambucil neoglycoside that are produced when an aglycon chlorambucil analog containing a secondary alkoxylamine moiety, a hydroxylamine moiety, or a hydrazine moiety is contacted with a reducing sugar selected from the group consisting of an L-sugar, a D-sugar, a deoxy-sugar, a dideoxy-sugar, a glucose epimer, a substituted sugar, a uronic acid, an oligosaccharide and mixtures thereof. Preferred reducing sugars are selected from the group consisting of D-allose, L-allose, D-altrose, L-altrose, D-arabinose, L-arabinose, 2,3,5-O-tribenzyl-D-arabinose, D-cellobiose, D-digitoxose, D-erythrose, D-fucose, L-fucose, 2,3,4-O-tribenzyl-L-fucose, D-galactose, L-galactose, 2-deoxy-D-galactose, D-galacturonose, N-acetyl-D-galactose, D-glucose, L-glucose, 2-deoxy-D-glucose, 2-fluoro-D-glucose, 3-fluoro-D-glucose, 3-O-methyl-D-glucose, 6-amino-D-glucose, 6-N-alloc-D-glucose, 6-chloro-D-glucose, 6-deoxy-D-glucose, D-glucuronose, D-glucuronolactone, L-gulose, D-lyxose, L-lyxose, D-mannose, L-mannose, N-acetyl-D-mannose, D-Galacto-(1,4)-β-D-Mannose, D-melibiose, D-MurNAc, L-noviose, D-olivose, L-rhamnose, 2,3,4-tri-O-acetyl-L-rhamnose, D-ribose, L-ribose, 2-deoxy-D-ribose, 2-deoxy-L-ribose, 2,3,5-tri-O- benzyl-D-ribose, D-talose, L-talose, D-threose, L-threose, D-xylose, L-xylose; and mixtures thereof. Preferred aglycon chlorambucil analogs are selected from the group consisting of:

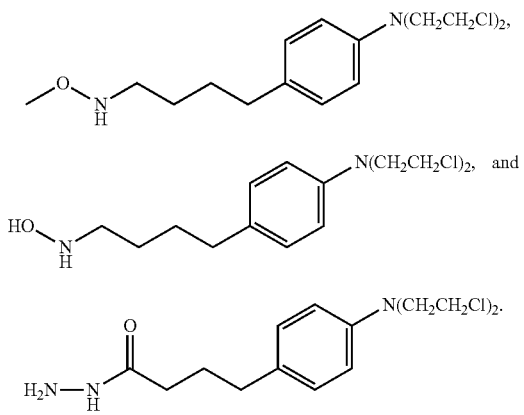

This aspect additionally encompasses compositions comprising the chlorambucil neoglycosides described above, as well as pharmaceutically acceptable esters, salts, or prodrugs thereof, combined with a pharmaceutically acceptable carrier. Furthermore, this aspect encompasses a library of chlorambucil neoglycosides comprising two or more of the chlorambucil neoglycosides as described above.

As further shown in the Example section below, the inventors have demonstrated that the compounds and compositions of the present invention exhibit biological activity against certain tumor cell lines. Thus, in a second aspect, the invention encompasses a method of treating cancer cells in a subject by contacting the cancer cells with an effective amount of one or more of the chlorambucil neoglycosides described above, a pharmaceutically acceptable ester, salt, or prodrugs thereof. Accordingly, in certain embodiments, the compositions of the present invention may encompass pharmaceutically acceptable esters, salts, or prodrugs of the chlorambucil neoglocosides described above. In some preferred embodiments, the compositions of the present invention may include a pharmaceutically acceptable carrier. In some embodiments, the compositions are for use in cancer treatment or for use in manufacturing a medicament for treating cancer.

In some preferred embodiments of the method of treating a subject having cancer cells, the cancer cells being contacted with an effective amount of the chlorambucil neoglycoside or pharmaceutically acceptable ester, salt or prodrug thereof are human lung cancer cells, human colorectal cancer cells, human liver cancer cells, human breast cancer cells, human ovarian cancer cells, or human central nervous system cancer cells.

In preferred embodiments of the method, the sugar moiety attached to the nitrogen atom in the chlorambucil neoglycoside used in the method is D-allose (10), D-altrose (12), D-arabinose (14), D-fucose (20), L-fucose (21), 2-deoxy-D-glucose (30), D-glucuronose (38), D-glucuronolactone (39), L-gulose (40), D-lyxose (41), L-lyxose (42), L-ribose (54), 2-deoxy-D-ribose (55), D-threose (60), L-threose (61), D-xylose (62), or L-xylose (63); or a pharmaceutically acceptable ester, salt or prodrug thereof. More preferably, the reducing sugar moiety is D-arabinose (14), L-arabinose (15), D-glucuronolactone (39), D-threose (60), L-threose (61), D-xylose (62), or L-xylose (63), with chlorambucil neoglycosides containing D-glucuronolactone (39) and D-threose (60) showing the highest anticancer cell line activity.

The form in which the active compound is administered to the cells is not critical; the active compound need only reach the cells, directly or indirectly. The invention encompasses preparation and use of medicaments and pharmaceutical compositions comprising a compound described herein as an active ingredient.

A chlorambucil neoglycoside is administered to a patient in a therapeutically effective amount. A chlorambucil neoglycoside can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A chlorambucil neoglycoside can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about 2 grams of the active ingredient, and preferably comprises from about 200 milligrams to about 1.0 gram of the active ingredient.

In addition, a chlorambucil neoglycoside can be administered alone, in combination with other chlorambucil neoglycosides, or with other pharmaceutically active compounds. The other pharmaceutically active compounds can be selected to treat the same disease as the chlorambucil neoglycoside or a different disease. If the patient is to receive or is receiving multiple pharmaceutically active compounds, the compounds can be administered simultaneously or sequentially in any order. For example, in the case of tablets, the active compounds may be found in one tablet or in separate tablets, which can be administered at once or sequentially in any order. In addition, it should be recognized that the compositions can be different forms. For example, one or more compounds may be delivered via a tablet, while another is administered via injection or orally as a syrup.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. For example, a kit may comprise two separate pharmaceutical compositions comprising respectively a first composition comprising a chlorambucil neoglycoside and a pharmaceutically acceptable carrier; and a composition comprising second pharmaceutically active compound and a pharmaceutically acceptable carrier. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . . . Second Week, Monday, Tuesday," etc. Other variations of memory aids will be readily apparent. A "daily dose" can be a single tablet or capsule or several pills or capsules to be taken on a given day. Also, a daily dose of a chlorambucil neoglycoside composition can consist of one tablet or capsule, while a daily dose of the second compound can consist of several tablets or capsules and vice versa. The memory aid should reflect this and assist in correct administration.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

In the treatment method of the present invention, a chlorambucil neoglycoside composition, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an effective amount of a chlorambucil neoglycoside and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(ε-caprolactone), a polyanhydride, a poly(beta-hydroxy butyrate), a poly(ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pregelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol.

Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like. Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

In other embodiments, the pharmaceutical composition can be prepared as a nutraceutical, i.e., in the form of, or added to, a food (e.g., a processed item intended for direct consumption) or a foodstuff (e.g., an edible ingredient intended for incorporation into a food prior to ingestion). Examples of suitable foods include candies such as lollipops, baked goods such as crackers, breads, cookies, and snack cakes, whole, pureed, or mashed fruits and vegetables, beverages, and processed meat products. Examples of suitable foodstuffs include milled grains and sugars, spices and other seasonings, and syrups.

Compositions for rectal or vaginal administration can be prepared by mixing a chlorambucil neoglycoside and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the chlorambucil neoglycoside. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a chlorambucil neoglycoside include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmalmically administrable formulations comprise the active ingredient in microcrystalline form or in a liposomal preparation.

A pharmaceutical composition of the invention can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point below 65 degrees F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares. Formulations suitable for nasal administration can, for example, comprise from about as little as 0.1% (w/w) and as much as 100% (w/w) of the active ingredient, and can further comprise one or more of the additional ingredients described herein.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the compound or compounds may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The chlorambucil neoglycoside of the present invention, the stereoisomers and prodrugs thereof, and the pharmaceutically acceptable salts of the peptides, stereoisomers, and prodrugs, can be administered to a patient at dosage levels in the range of from about 0.01 to about 1,000 mg per day. For a normal adult human having a body weight of about 70 kg, a dosage in the range of from about 0.01 to about 300 mg is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compound is administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the chlorambucil neoglycoside. In some embodiments, the minimum amount is generally in the range from $10^{-9}$ to $10^{-5}$ molar. In other embodiments, the minimum amount is typically in the range from $10^{-7}$ to $10^{-5}$ molar.

In preferred embodiments, a pharmaceutical composition comprising a chlorambucil neoglycoside can be administered to a patient at dosage levels in the range of about 0.1 to about 7,000 mg per day. A preferred dosage range is about 1 to about 100 mg per day. In other embodiments, a pharmaceutical composition comprising a neoglycoside can be administered to deliver a dose of between 1 nanogram per day per kilogram body weight and 100 milligrams per day per kilogram body weight, preferably from about 0.1 to about 10 mg/kg body weight of the individual per day, and preferably to deliver of between 100 milligrams and 2 grams, to a human patient.

The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill of one in the art in view of this disclosure. It is understood that the ordinarily skilled physician or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

In some embodiments, a chlorambucil neoglycoside of the present invention, a stereoisomer or prodrug thereof, or a pharmaceutically acceptable salt of the stereoisomer or prodrug; is administered to a subject in need of treatment therewith, preferably in the form of a pharmaceutical composition. It is generally preferred that such administration be oral or pulmonary. However, if the subject being treated is unable to swallow, or oral administration is otherwise impaired or undesirable, parenteral or transdermal administration will be appropriate.

While this invention has been described in conjunction with the various exemplary embodiments outlined in the Examples below, various alternatives, modifications, variations, improvements and/or substantial equivalents, whether known or that are or may be presently unforeseen, may become apparent to those having at least ordinary skill in the art.

3. Examples

Example 1

Synthesis and Characterization of Chlorambucil Neoglycosides

Summary

To systematically assess the impact of glycosylation and the corresponding chemoselective linker upon the anticancer activity/selectivity of the drug chlorambucil, herein we report the synthesis and anticancer activities of a 63-member library of chlorambucil-based neoglycosides. A comparison of N-alkoxyamine-, N-acyl hydrazine- and N-hydroxyamine-based chemoselective glycosylation of chlorambucil revealed sugar- and linker-dependent partitioning among open and closed-ring neoglycosides and corresponding sugar-dependent variant biological activity. Cumulatively, this study represents the first neoglycorandomization of a synthetic drug and expands our understanding of the impact of sugar structure upon product distribution/equilibria in the context of N-alkoxyamino-, N-hydroxyamino- and N-acyl hydrazine-based chemoselective glycosylation. This study also revealed several analogs with increased in vitro anticancer activity, most notably D-threoside 60, which displayed much broader tumor specificity and notably increased potency over the parent drug.

More specifically, D-threoside 60 displayed increases in potency of up to 15-fold compared to 1—representing the most active chlorambucil glycoside reported to date. Representative sugars identified as hits in the context of N-methoxyaminosubstituted 1, were subsequently conjugated via N-acyl hydrazine- and N-hydroxyamine-based strategies and the products characterized and evaluated for anticancer activity. Analysis of these second generation neoglycoside analogs revealed sugar-dependent partitioning among open and closed-ring neoglycosides and corresponding sugar-dependent variant biological activity.

Results and Discussion

Chlorambucil N-alkoxyamino-Based Neoglycorandomization (Scheme 1).

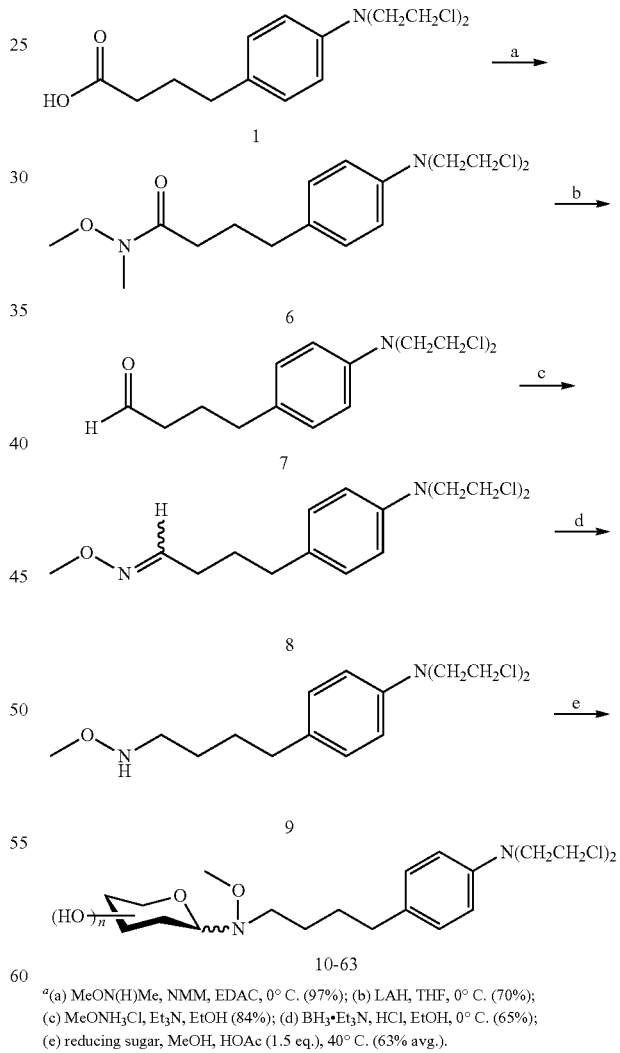

Scheme 1. Synthesis of the N-alkoxyamino-based chlorambucil library[a]

[a](a) MeON(H)Me, NMM, EDAC, 0° C. (97%); (b) LAH, THF, 0° C. (70%); (c) MeONH$_3$Cl, Et$_3$N, EtOH (84%); (d) BH$_3$•Et$_3$N, HCl, EtOH, 0° C. (65%); (e) reducing sugar, MeOH, HOAc (1.5 eq.), 40° C. (63% avg.).

Chlorambucil was converted to the Weinreb amide 6 using the EDAC coupling agent in excellent yield (97%) and then selectively reduced to the corresponding aldehyde with LAH.

Compound 7 was subsequently condensed with methoxyamine.HCl in the presence of organic base providing a mixture of E- and Z-oximes (8). Reduction of the carbon-nitrogen double bond was accomplished with BH3.Et3N in a manner similar to that for previously described neoaglycons. This convenient strategy yielded neoaglycon 9 in four steps with an overall yield of 37% and required only a single chromatographic purification. While standard neoglycosylation conditions (3/1 DMF/HOAc) provided a slightly greater yield (68%) of neo-D-riboside 53 in a pilot reaction, the use of MeOH with a small molar excess of HOAc (i.e., 1.5 equivalents) as an acidic proton source was sufficient for the reaction to proceed in an equivalent amount of time (54% yield) and also simplified subsequent solvent evacuation (See Table 1).

TABLE 1

Optimization of Neoglycorandomization Conditions

| entry | sugar (no. eq.) | solvent[a] | reaction time | yield[d] |
|---|---|---|---|---|
| 1 | D-ribose (3) | MeOH | 6 h | 56% |
| 2 | D-ribose (3) | MeOH + HOAc (1.5 eq.) | 3 h | 54% |
| 3 | D-ribose (3) | MeOH:10 mM NaOAc 1:1[b] | n/r[c] | — |
| 4 | D-ribose (3) | DMF:HOAc 3:1 | 4 h | 68% |
| 5 | L-ribose (2) | MeOH + HOAc (1.5 eq.) | 3.5 h | 54% |

[a]Concentration of 9 at 90 mM.
[b]pH = 5.5.
[c]No reaction due to decomposition of starting material.
[d]Percent yield of 53.

Figure 2A:
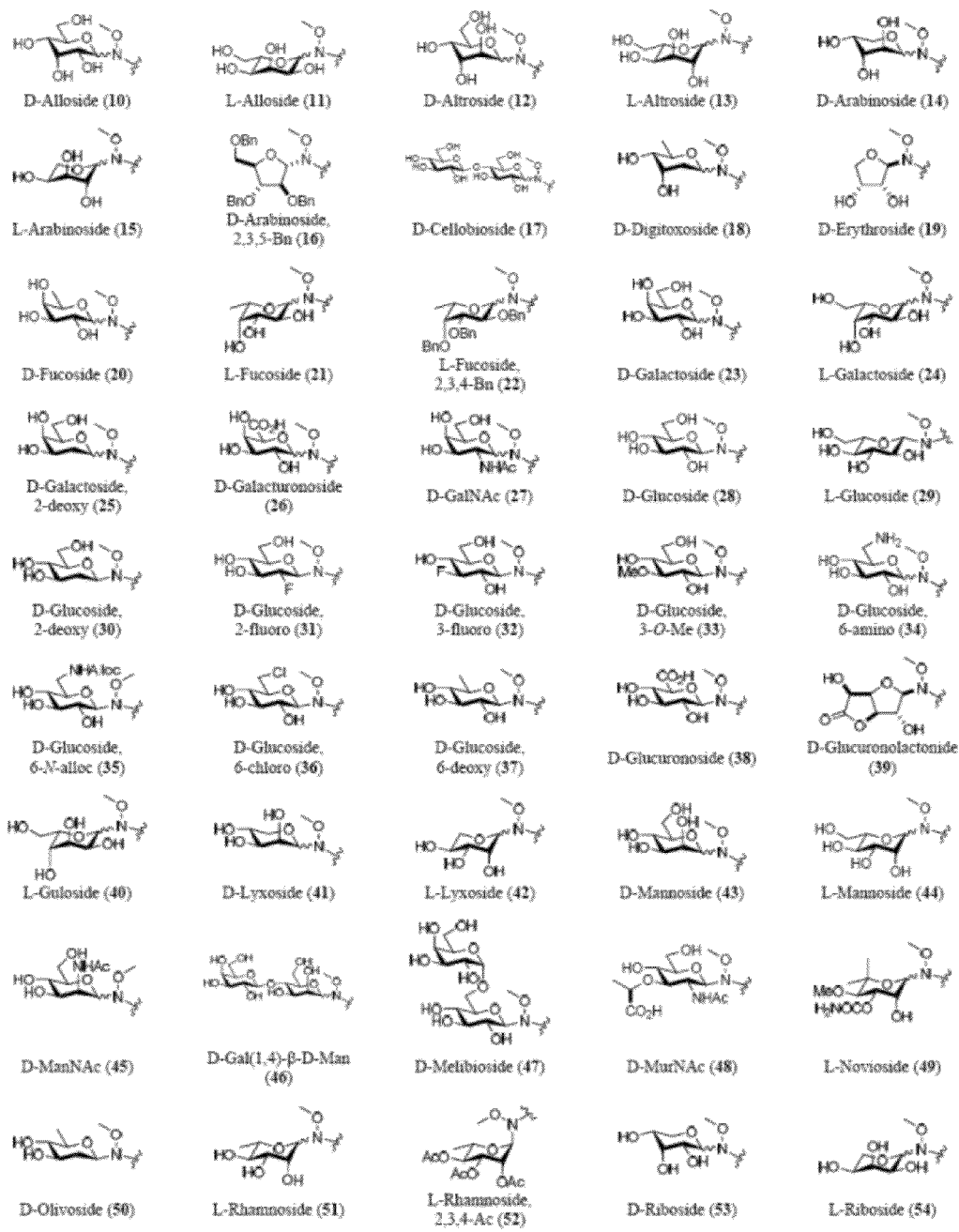
FIGS. 2A and 2B together show the chlorambucil neoglycoside library of the present invention.
Figure 2B:
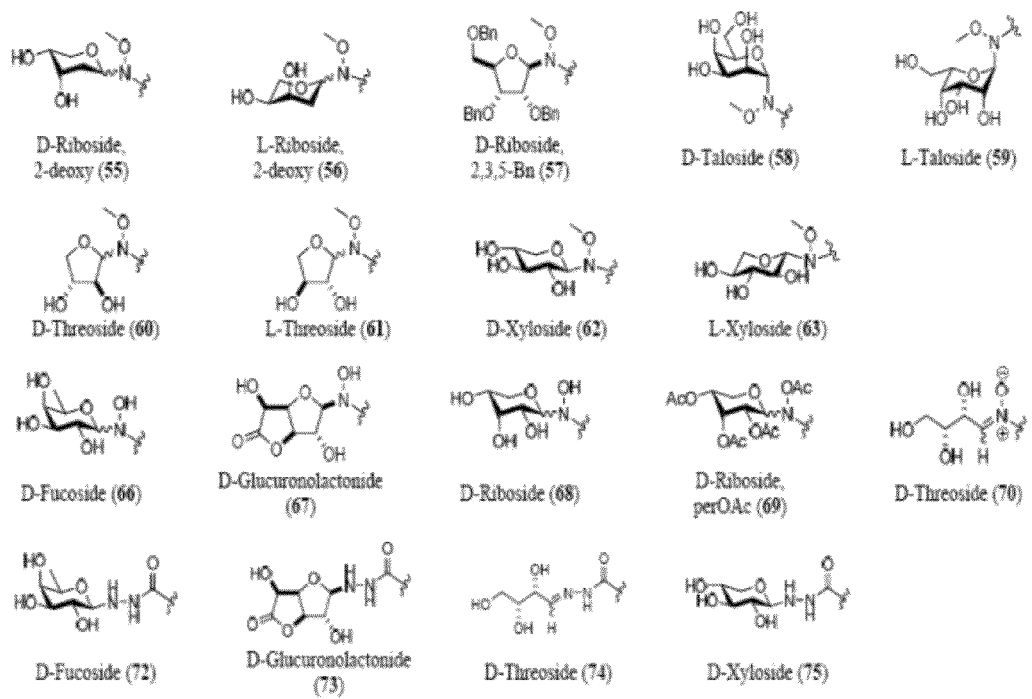

Using these optimized conditions (90 μM 9, 2 equiv. sugar, 40° C., 1.5 eq. HOAc in MeOH) a 54-member library of neoglycosides (10-63, see FIGS. 2A and 2B) was synthesized with an average isolated yield of 63% wherein high-throughput solid phase extraction provided an average purity of 92.9% (see Table 2).

TABLE 2

HPLC-Determined Purity of Neoglycoside Library

| entry | purity (%) |
|---|---|
| 10 | 95.5 |
| 11 | 95.1 |
| 12 | 95.1 |
| 13 | 95.0 |
| 14 | 95.5 |
| 15 | 93.4 |
| 16 | 94.1 |
| 17 | 94.6 |
| 18 | 95.9 |
| 19 | 92.1 |
| 20 | 93.5 |
| 21 | 95.6 |
| 22 | 91.1 |
| 23 | 90.1 |
| 24 | 92.9 |
| 25 | 91.6 |
| 26 | 91.8 |
| 27 | 90.1 |
| 28 | 90.2 |
| 29 | 91.6 |
| 30 | 92.6 |
| 31 | 95.4 |
| 32 | 91.0 |
| 33 | 90.6 |
| 34 | 91.5 |
| 35 | 91.3 |
| 36 | 90.0 |
| 37 | 91.0 |
| 38 | 92.1 |
| 39 | 96.7 |
| 40 | 96.8 |
| 41 | 95.5 |
| 42 | 97.0 |
| 43 | 97.1 |
| 44 | 90.7 |
| 45 | 90.9 |
| 46 | 91.7 |
| 47 | 92.2 |
| 48 | 94.9 |
| 49 | 95.3 |
| 50 | 96.7 |
| 51 | 97.1 |
| 52 | 95.2 |
| 53 | 96.8 |
| 54 | 96.7 |
| 55 | 95.5 |
| 56 | 94.3 |
| 57 | 95.9 |
| 58 | 94.5 |
| 59 | 97.2 |
| 60 | 95.8 |
| 61 | 95.0 |
| 62 | 96.0 |
| 63 | 95.9 |
| 66 | 95.5 |
| 67 | 95.0 |
| 68 | 95.6 |
| 69 | 96.6 |
| 70 | 95.7 |
| 72 | 96.5 |
| 73 | 95.6 |
| 74 | 98.1 |
| 75 | 97.3 |
| 9 | 98.9 |
| 65 | 98.1 |
| 71 | 98.3 |

Figure 3:
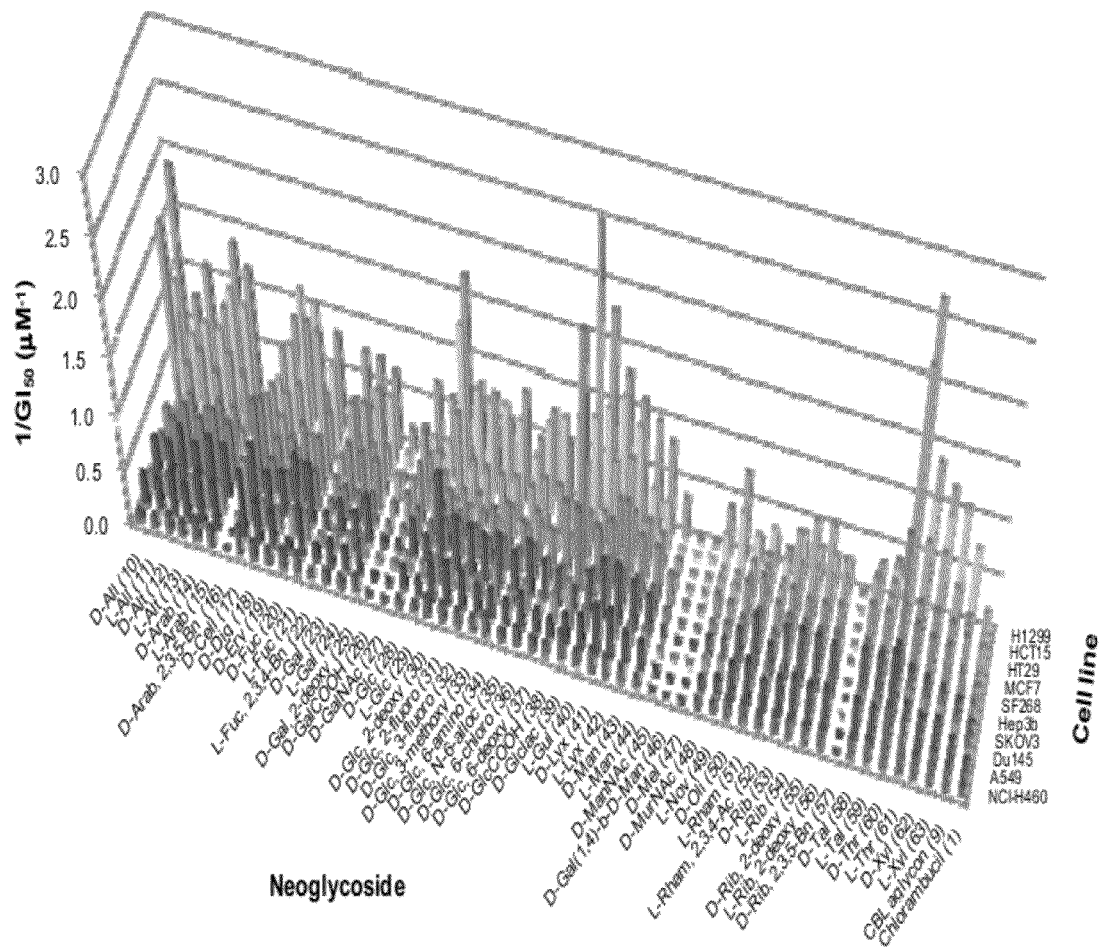
FIG. 3 is a summary of GI50 data from the high-throughput growth inhibition assay of 10-63 (reciprocal values displayed). Comparisons were performed against the aglycon (9) and chlorambucil (1). GI50 data and error values are provided in Table 5. Representative cancer cell lines tested include: NCI-H460 (lung), A549 (lung), Du145 (prostate), SKOV3 (ovary), Hep3b (liver), SF268 (brain), MCF7 (breast), HT29 (colorectal), HCT15 (colorectal), and H1299 (lung).
Figure 4:
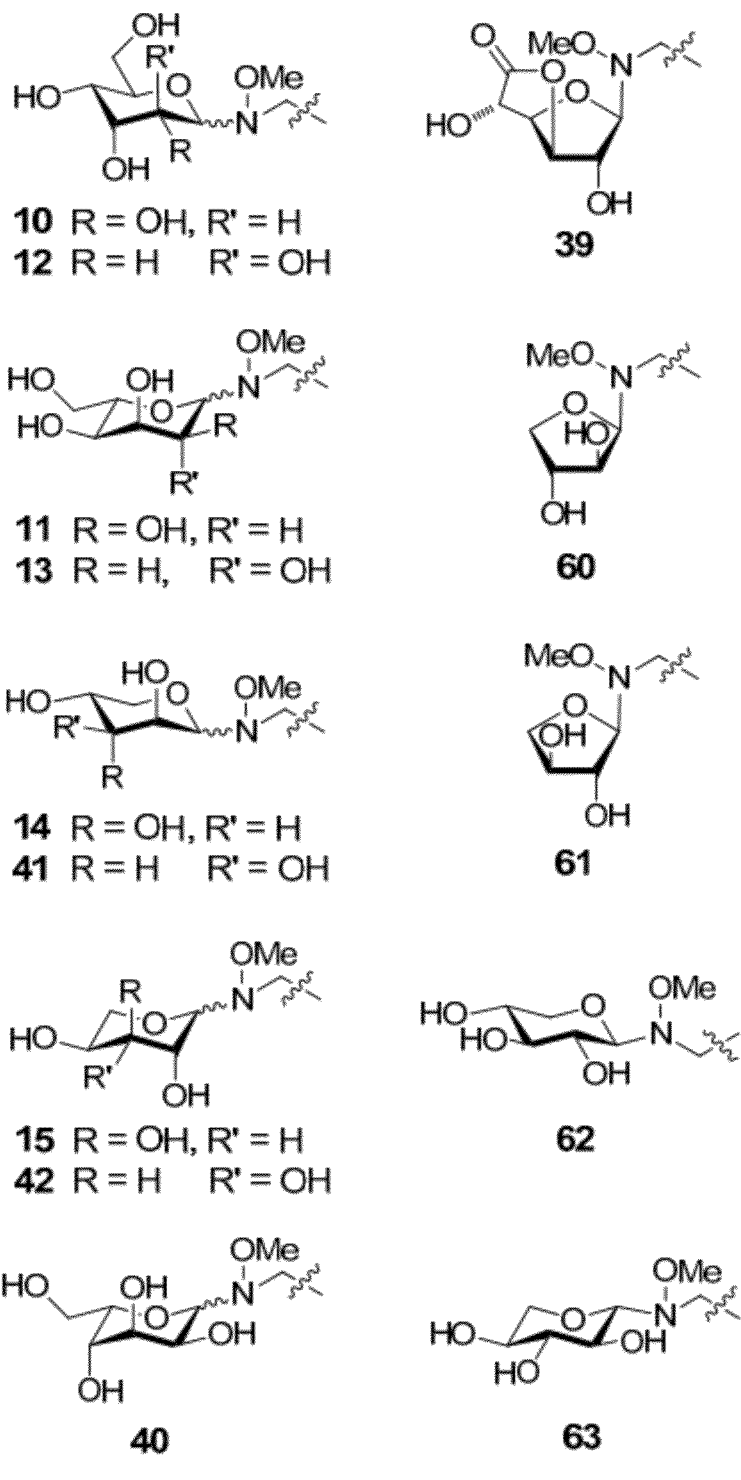
FIG. 4 shows structures of the most antiproliferative chlorambucil N-alkoxyamino-based neoglycosides against a ten-member carcinoma panel.
Figure 4:
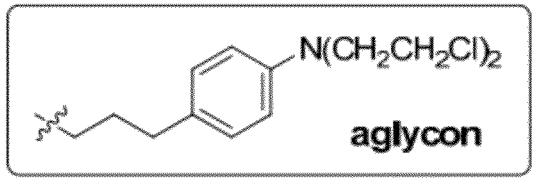

Product yields paralleled the overall reactivity trend: tetroses (79±10%)>deoxy sugars (69±6%)>pentoses (62±7%)>hexoses (56±5%)—likely reflecting the general reducing sugar solubility in the selected solvent system. Unlike prior neoglycorandomized libraries, a preference for β-anomer formation of chlorambucil neoglycosides was generally less predominate. Rather, a strong 1,2-trans relationship was typically observed (see Tables 3 and 4). Anticancer activity of chlorambucil N-alkoxyamino-based neoglycosides. The antiproliferative activity (i.e., GI50) of neoglycosides 10-63 were evaluated using a ten-member panel of human carcinomas from various lung, colorectal, liver, breast, prostate, CNS, and ovarian cell lines with 1 and neoaglycon 9 as comparators (see FIG. 3). Based upon this study, aglycon 9 displayed slightly better GI50 values (1.1-4.4 μM) compared to the parent drug 1 (5.0-11.0 μM) and the vast majority of the library members had an average GI50 also comparable to or lower than chlorambucil (see Table 5). Out of the 54 analogs, 19 possessed GI50s in the high nanomolar range in at least one cell line, six of which displayed GI50s in the high nanomolar range in three or more lines. Of this latter set, two neoglycosides (D-glucuronolactonide 39 and D-threoside 60, see FIG. 3) were identified as the two most potent neoglycosides. In comparison to the parent 1, 39 displayed a 6-fold improvement in average growth inhibition across the cell panel, with the most sensitive cell line being SF268 glioblastoma (12-fold improved). Likewise, D-threoside 60 presented an average elevated potency of 8-fold over 1, with 12-, 13-, and 15-fold improved activities toward HT29 (colorectal), H1299 (lung), and HCT15 (colorectal) cancers, respectively, over the parent drug. FIG. 4 shows the structures of the most antiproliferative chlorambucil N-alkoxyamino-based neoglycosides against a ten-member carcinoma panel.

TABLE 3

¹H NMR Anomeric Proton and HRMS Characterization of Methoxyneoglocosides

| entry | neoglycoside | α-anomeric H1 δ (ppm) | α-anomeric H1 J (Hz) | β-anomeric H1 δ (ppm) | β-anomeric H1 J (Hz) | α:β ratio | HRMS m/z measured | HRMS m/z calculated |
|---|---|---|---|---|---|---|---|---|
| 10 | D-Alloside | 4.55 | 4.4 | 4.38 | 9.2 | 1:7 | 503.1699[a] | 503.1687 |
| 11 | L-Alloside | 4.55 | 4.4 | 4.38 | 9.0 | 1:7 | 503.1674[a] | 503.1687 |
| 12 | D-Altroside | 4.46 | 5.2 | 4.64 | 5.8 | 19:1 | 503.17047[b] | 503.16861 |
| 13 | L-Altroside | 4.46 | 5.2 | 4.64 | 5.7 | 19:1 | 503.16993[b] | 503.16861 |
| 14 | D-Arabinoside | 4.45 | 5.5 | 4.66 | 6.1 | 19:1 | 473.1581[a] | 473.1581 |
| 15 | L-Arabinoside | 4.45 | 5.5 | 4.66 | 6.1 | 19:1 | 473.1568[a] | 473.1581 |
| 16 | D-Arabinoside, 2,3,5-Bn | not observed | | 4.71 | 7.3 | β only | 743.2981[a] | 743.2989 |
| 17 | D-Cellobioside | 4.44 | 7.9 | 4.02 | 9.2 | 1:4 | 665.22336[b] | 665.22144 |
| 18 | D-Digitoxoside | 4.75 | 4.9 | 4.91 | 6.9 | 1:4 | 471.1805[a] | 471.1788 |
| 19 | D-Erythroside | 4.52 | 4.0 | not observed | | α only | 421.16665[c] | 421.16554 |
| 20 | D-Fucoside | 4.44 | 5.5 | 3.94 | 9.0 | 1:3 | 487.17411[b] | 487.17370 |
| 21 | L-Fucoside | 4.43 | 5.4 | 3.94 | 9.0 | 1:3 | 487.17473[b] | 487.17370 |
| 22 | L-Fucoside, 2,3,4-Bn | 5.00-4.60[d] | n/d[e] | 4.28 | 9.0 | 1:2 | 757.3162[a] | 757.3146 |
| 23 | D-Galactoside | 4.45 | 5.7 | 4.01 | 9.0 | 1:2 | 503.16995[b] | 503.16861 |
| 24 | L-Galactoside | 4.45 | 5.7 | 4.01 | 9.0 | 1:2 | 503.17016[b] | 503.16861 |
| 25 | D-Galactoside, 2-deoxy | 4.91 | 6.6 | 4.21 | 10.9 | 1:2 | 465.1908[c] | 465.1918 |
| 26 | D-Galacturonoside | 4.46 | 5.2 | 4.05 | 9.0 | 5:1 | 495.16835[f] | 495.16593 |
| 27 | D-GalNAc | 4.46 | 6.9 | 4.24 | 9.8 | 1:1.1 | 544.19466[b] | 544.19516 |
| 28 | D-Glucoside | not observed | | 4.03 | 8.9 | β only | 503.17059[b] | 503.16861 |
| 29 | L-Glucoside | not observed | | 4.03 | 8.9 | β only | 503.17047[b] | 503.16861 |
| 30 | D-Glucoside, 2-deoxy | not observed | | 4.24 | 9.8 | β only | 465.19310[f] | 465.19175 |
| 31 | D-Glucoside, 2-fluoro | not observed | | 4.32 | 8.9 | β only | 505.16620[b] | 505.16428 |
| 32 | D-Glucoside, 3-fluoro | not observed | | 4.04 | 9.0 | β only | 505.16630[b] | 505.16428 |
| 33 | D-Glucoside, 3-O-Me | not observed | | 4.02 | 9.0 | β only | 517.18392[b] | 517.18426 |
| 34 | D-Glucoside, 6-amino | 4.69 | 3.5 | 4.03 | 9.0 | 1:3 | 502.1850[a] | 502.1846 |
| 35 | D-Glucoside, 6-N-alloc | not observed | | 4.01 | 8.9 | β only | 586.20644[b] | 586.20573 |
| 36 | D-Glucoside, 6-chloro | not observed | | 4.03 | 9.0 | β only | 521.13454[b] | 521.13473 |
| 37 | D-Glucoside, 6-deoxy | not observed | | 3.97 | 9.0 | β only | 487.17556[b] | 487.17370 |
| 38 | D-Glucuronoside | not observed | | 4.07 | 9.0 | β only | 495.16863[f] | 495.16593 |
| 39 | D-Glucuronolactonide | not observed | | 4.62 | 2.1 | β only | 477.15721[f] | 477.15537 |
| 40 | L-Guloside | 4.58 | 4.7 | 4.40 | 9.3 | 1:6 | 503.17060[b] | 503.16861 |
| 41 | D-Lyxoside | 4.57 | 5.4 | 4.28 | 8.1 | 1:4 | 473.15997[b] | 473.15805 |
| 42 | L-Lyxoside | 4.57 | 5.4 | 4.28 | 8.3 | 1:4 | 473.15950[b] | 473.15805 |
| 43 | D-Mannoside | 4.14 | 1.8 | 4.55 | 6.4 | 3:1 | 503.17006[b] | 503.16861 |
| 44 | L-Mannoside | 4.14 | 1.9 | 4.55 | 6.4 | 3:1 | 503.16992[b] | 503.16861 |
| 45 | D-ManNAc | 4.66 | 4.1 | 4.02 | 7.8 | 2:1 | 544.19559[b] | 544.19516 |
| 46 | D-Gal(1,4)-β-D-Man | 4.10 | 2.9 | 4.38 | 7.3 | 1:1.1 | 665.22165[b] | 665.22144 |
| 47 | D-Melibioside | not observed | | 4.01 | 8.9 | β only | 665.22060[b] | 665.22144 |
| 48 | D-MurNAc | not observed | | 4.31 | 9.6 | β only | 616.2163[a] | 616.2163 |
| 49 | L-Novioside | 4.16 | 2.6 | 4.40 | 8.1 | 1:1 | 558.2083[a] | 558.2109 |
| 50 | D-Olivoside | not observed | | 4.17 | 9.9 | β only | 449.19692[f] | 449.19684 |
| 51 | L-Rhamnoside | 4.14 | 3.2 | 4.53 | 6.1 | 3:1 | 487.1751[a] | 487.1737 |
| 52 | L-Rhamnoside, 2,3,4-Ac | 4.11 | singlet | not observed | | α only | 613.20527[b] | 613.20539 |
| 53 | D-Riboside | 4.56 | 3.4 | 4.27 | 8.7 | 1:3 | 473.1587[a] | 473.1581 |
| 54 | L-Riboside | 4.59 | 3.4 | 4.21 | 8.7 | 1:3 | 473.1579[a] | 473.1581 |
| 55 | D-Riboside, 2-deoxy | 4.91 | 6.3 | 4.11 | 9.2 | 1:2 | 435.18194[f] | 435.18119 |
| 56 | L-Riboside, 2-deoxy | 4.91 | 6.4 | 4.12 | 9.2 | 1:2 | 435.18191[f] | 435.18119 |
| 57 | D-Riboside, 2,3,5-Bn | 4.78 | 3.5 | not observed | | α only | 743.3005[a] | 743.2989 |
| 58 | D-Taloside | 4.55 | 3.4 | not observed | | α only | 503.16941[b] | 503.16861 |
| 59 | L-Taloside | 4.55 | 3.4 | not observed | | α only | 503.17051[b] | 503.16861 |
| 60 | D-Threoside | not observed | | 4.41 | 4.0 | β only | 443.14850[b] | 443.14748 |
| 61 | L-Threoside | not observed | | 4.41 | 4.0 | β only | 443.14794[b] | 443.14748 |
| 62 | D-Xyloside | not observed | | 3.95 | 9.0 | β only | 473.15906[b] | 473.15805 |
| 63 | L-Xyloside | not observed | | 3.95 | 9.0 | β only | 473.15941[b] | 473.15805 |

[a] HRMS (ESI) m/z for [M + Na]⁻.
[b] HRMS (MALDI) m/z for [M + Na]⁻.
[c] HRMS (ESI) m/z for [M + H]⁻.
[d] Anomeric proton obscured by another peak.
[e] Not determined.
[f] HRMS (MALDI) m/z for [M + H]⁻.

TABLE 4

$^1$H NMR Anomeric Proton and HRMS Characterization of Hydroxy- and Hydrazidoneoglycosides

| | | iminyl H1[2] | | α-anomeric H1 | | β-anomeric H1 | | im.:α:β[b] | HRMS m/z | |
|---|---|---|---|---|---|---|---|---|---|---|
| entry | neoglycoside | δ (ppm) | J (Hz) | δ (ppm) | J (Hz) | δ (ppm) | J (Hz) | ratio | measured | calculated |
| 66 | D-Fucoside | 7.25 | 5.8 | 4.40 | 4.9 | 3.86-3.79[c] | n/d[d] | 1.8:2.7:1 | 473.15911[e] | 473.15805 |
| 67 | D-Glucuronolactonide | 7.25 | 6.3 | not observed | | 4.57 | 2.3 | 2.5:0:1 | 485.12254[e] | 485.12166 |
| 68 | D-Riboside | 7.17 | 6.3 | 4.51 | 2.9 | 4.16 | 8.7 | 2:1:1 | 459.1441[f] | 459.1424 |
| 69 | D-Riboside, perOAc | not observed | | 4.89 | 2.9 | 4.58 | 9.2 | 0:2:1 | 627.1859[f] | 627.1847 |
| 70 | D-Threoside | 7.22 | 5.8 | not observed | | not observed | | im. only | 429.13188[e] | 429.13183 |
| 72 | D-Fucoside | not observed | | not observed | | 3.86 | 8.7 | β only | 486.15233[e] | 486.15330 |
| 73 | D-Glucuronolactonide | 7.57 | 4.3 | not observed | | 4.78 | 1.4 | 1:0:1 | 498.11631[e] | 498.11691 |
| 74 | D-Threoside | 7.53 | 4.9 | not observed | | not observed | | im. only | 442.12721[e] | 442.12708 |
| 75 | D-Xyloside | 7.54 | 5.0 | not observed | | 3.85 | 8.7 | 1:0:2.3 | 472.13712[e] | 472.13765 |

[a]Data of most prevalent imine isomer if more than one are present.
[b]Ratio of iminyl (im.) isomers:α anomer:β anomer.
[c]Anomeric proton obscured by another peak.
[d]Not determined.
[e]HRMS (MALDI) m/z for [M + Na]⁻.
[f]HRMS (ESI) m/z for [M + Na]⁻.

The activity assessment described above revealed the following general structure-activity relationships. First, sugars that favor furanosyl-derived neoglycosides (e.g., threosides 60 & 61, glucuronolactonide 39, arabinosides 14 & 15, lyxosides 41 & 42, and xylosides 62 & 63) led to the greatest improvements in anticancer activity. Second, relative configuration within this furanoside-derived neoglycoside series influenced potency. Specifically, those tetroses or pentoses with a 2,3-trans dihydroxy orientation [e.g., D-threoside 60 (2S,3R), L-threoside 61 (2R,3S), and 39 (D-2S,3R)] were generally more potent than those with a corresponding 2,3-cis configuration [e.g., D-erythroside 19 (2R,3R), D-riboside 53 (2R,3R), and L-riboside 54 (2S,3S)] while D- and L-saccharide enantiomers of this furanoside-derived group were found to have similar values. Third, among neohexosides, a 3R hydroxyl group (i.e., axial in the chair conformation) enhances selectivity toward lung (H1299) and colon (HCT-15) cancer cell lines (e.g., allosides 10 & 11, altrosides 12 & 13, and L-guloside 40). Finally, most neoglycosides deriving from sugars known to be GLUT substrates and mediate GLUT-dependent uptake of conjugates (e.g., D-glucoside 28 or 3-methoxy-D-glucoside 33) were not among the most active and/or selective hits identified. Additionally, comparison of the anomeric composition of either the most active neoglycosides or the library as a whole to the inhibitory data does not reveal that a distinct correlation exists between anomers and activity. To illustrate using the antiproliferative neo-D-pentosides (the two with the most extreme anomeric biases), D-arabinoside 14 (α/β19/1) and D-xyloside 62 (β only) have similar GI50s in nine of the ten cell lines, not providing any distinction between the two anomers and overall impact on growth inhibition.

Chlorambucil N-Hydroxyamino-Based Neoglycosylation (Scheme 2).

Given the clear impact of chlorambucil neoglycosylation upon anticancer activity, we subsequently set out to examine the specific contribution of the neoglycoside handle. Similar to alkoxyamino-based chemoselective neoglycosylation, previous studies have revealed hydroxyamines and hydrazides to also provide the corresponding closed-ring glycosides. Additionally, we envisioned that use of a hydroxyamino handle may allow for additional modification at the hydroxyl group, providing a facile means for further diversification. To create the two modified aglycons, only slight changes in the synthesis were required. In a fashion similar to the procedure described in Scheme 1, aldehyde 7 was combined with hydroxyamine HCl to form a mixture of E- and Z-oximes (64) that were reduced with BH$_3$.Et$_3$N complex. As with the synthesis described in Scheme 1, only aglycon 65 required column chromatography for purification in the four-step process from 1 (Scheme 2, 44% overall yield). Hydrazide formation (71) was achieved by reacting the N-hydroxysuccinimidyl ester of 1 with hydrazine in the presence of DMAP in pyridine. Using the previously described neoglycosylation conditions (see Scheme 1), the focused hydroxyamine (66-70) and hydrazide (72-75) neoglycosyl sets were synthesized using sugars identified as hits from the alkoxyamino-based series 10-63—specifically: D-glucuronolactone and D-threose, which had superior performance throughout the panel; D-xylose, the most active of the pentoses; and D-fucose, which displayed the most pronounced selectivity toward one tumor line (HCT-15 colorectal).

Scheme 2. Synthesis of the N-acyl hydrazine- and N-hydroxyamino-based chlorambucil libraries[a]

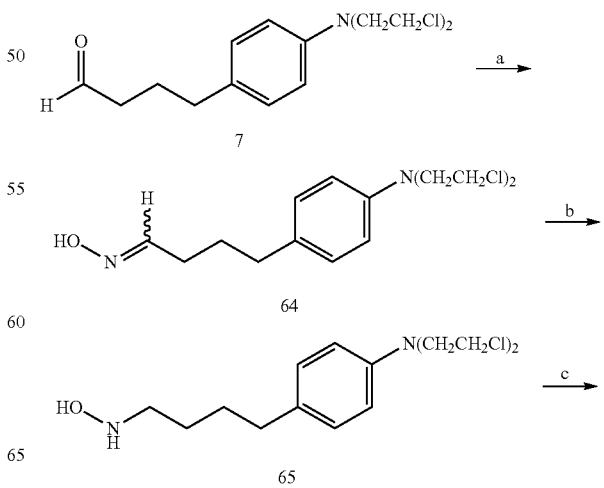

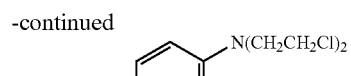

66-70

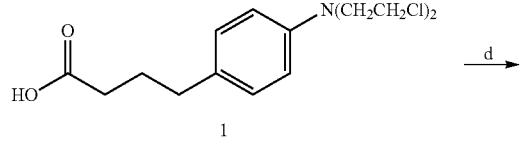

1

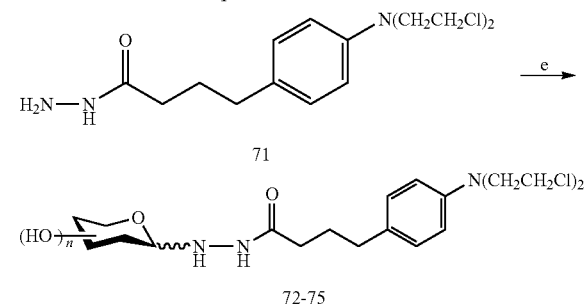

72-75

*(a) HONH₃Cl, Et₃N, EtOH (98%); (b) BH·Et₃N·HCl, EtOH, 0° C. (65%); (c) reducing sugar, MeOH, HOAc (1.5 eq.), 40° C. (47 avg.); (d) (i) N-hydroxysuccinimide, DIC, THF, 40° C., (ii) NH₂NH₂, pyridine, DMAP, 40° C. (85%); (e) reducing sugar, MeOH, HOAc (1.5 eq.), 40° C. (62% avg.).

Figure 5:
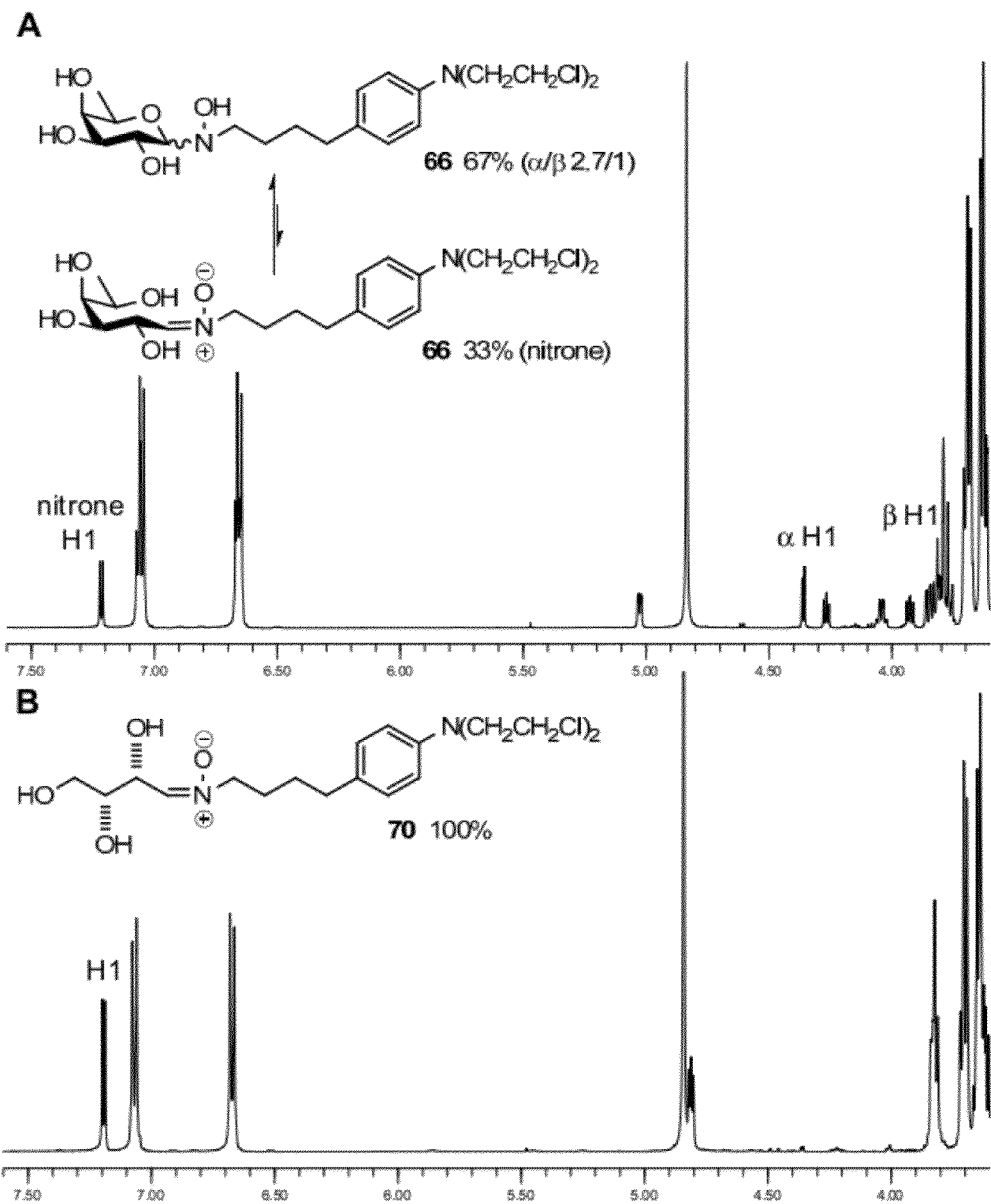
FIG. 5 shows $^1$H NMR spectra of N-hydroxyaminochlorambucil glycosides. A. Equilibrium between the cyclic neoglycoside and acyclic nitrone of D-fucoside 66. B. Nitrone form of the chlorambucil Dthreoside 70. Both spectra obtained at 500 MHz in CD$_3$OD.
Figure 6:
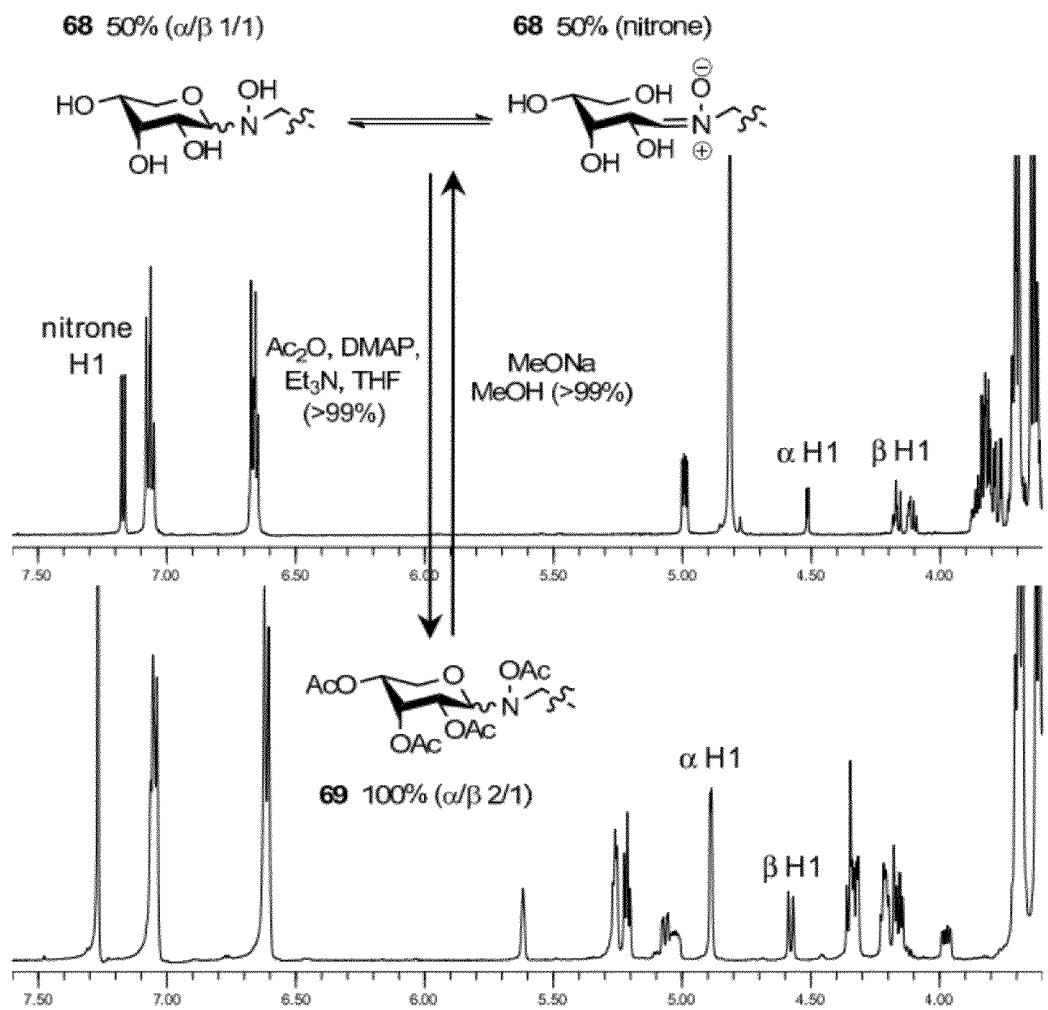
FIG. 6 shows $^1$H NMR spectra demonstrating interconversion of N-hydroxyaminochlorambucil-D-riboside between the cyclic neoglycoside and acyclic nitrone 68 and peracetylated analog 69. Both spectra obtained at 500 MHz with 68 in CD$_3$OD and 69 in CDCl$_3$.

NMR analysis of the 66-70 neoglycosides revealed the desired closed-ring α- and β-anomeric forms were usually in equilibrium with an open-chain imine isomer. Evidence for this was based upon the observed $^1$H NMR chemical shift of the H1 (doublets) and H2 (doublets of doublets) protons at 7.2-7.5 and 5.1-5.0 ppm, respectively, indicating the presence of an iminyl double-bond. Such nitrone formation is well-precedented for the condensation of aldehydes and monosubstituted hydroxyamines. However, in the context of glycoside formation, only a handful of such glycosides have been reported, comprised of protected saccharides and small N-alkyl-N-hydroxyamines. From the current study, the nature of the sugar influences the thermodynamic equilibrium and thereby, product distribution. Specifically, the D-fucoside-derived 66 predominately adopted the closed-ring isomer (67%), Dglucuronolactone (67) and D-ribose (68) favored the open-chain nitrone (71% and 50%, respectively), while D-threose (70) led solely to nitrone (see FIG. 5; Table 2). These equilibria could be shifted upon nitrone modification. For example, peracetylation of neoriboside 68 using acetic anhydride and DMAP in THF promoted ring closure based upon $^1$H NMR (see FIG. 6) and ESI-MS analysis. Deacetylation of the peracetate 69 in base reestablished the mixture of isomers, demonstrating that changing the electronics of the nitrone oxygen will promote ring opening and closure, as will the type of ligated sugar. Interestingly, the anomeric ratio also changed, moving from a 1/1 ratio as the nitrone to 2/1 as the tetraacetate, contrasting from the ⅓ α/β ratio of methoxyamine D-riboside (53).

Chlorambucil N-Acyl Hydrazine-Based Neoglycosylation (Scheme 2).

Figure 7:
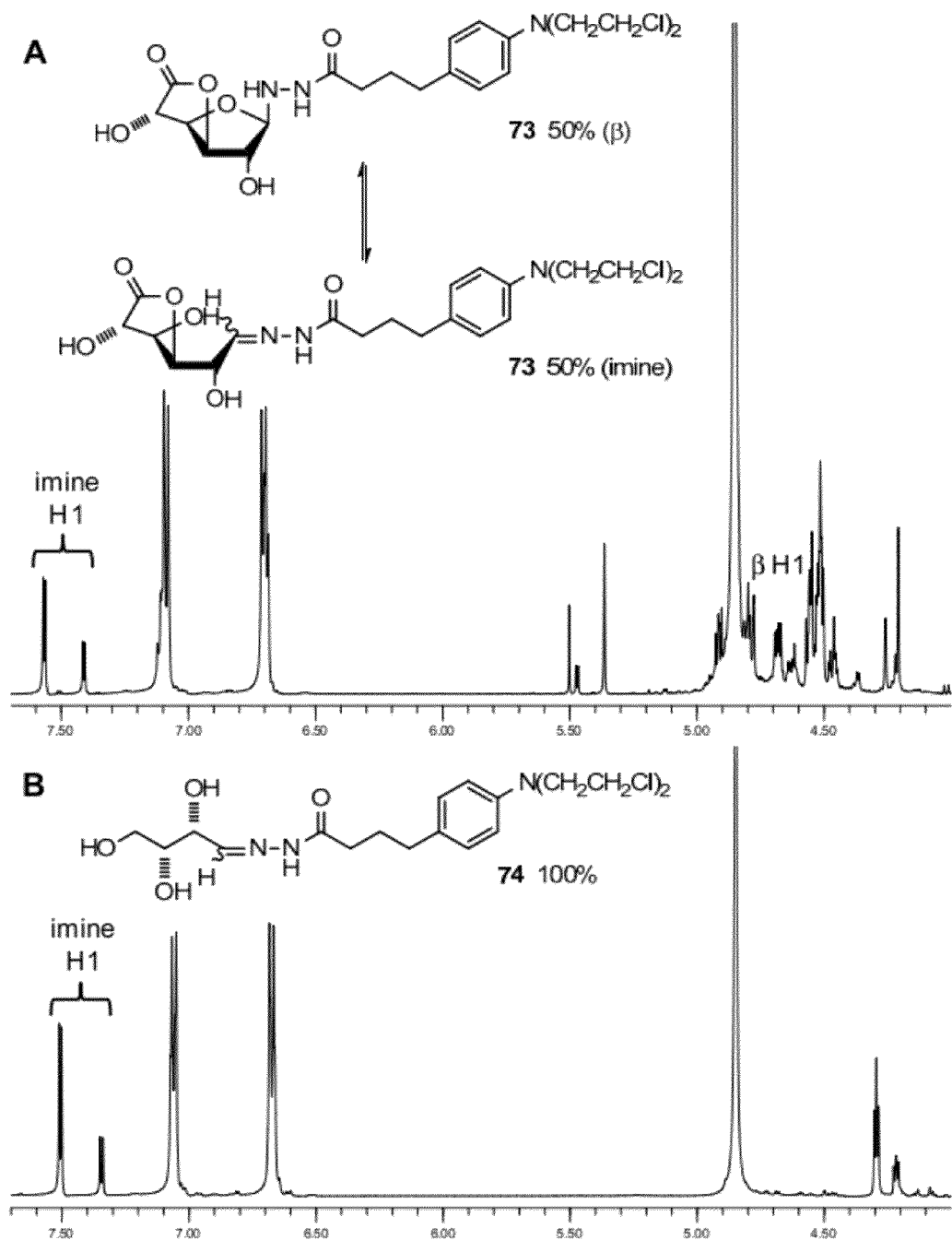
FIG. 7 shows $^1$H NMR spectra of N-hydrazidochlorambucil glycosides. A. Equilibrium between the cyclic neoglycoside and acyclic imine of D-glucurono-6,3-lactonide 73. B. Nitrone form of the chlorambucil D-threoside 74. Both spectra obtained at 500 MHz in CD$_3$OD.

A conformational study of sugar acetylhydrazides by Bendiak indicated that natural hexose and pentose (e.g., D-Glc, D-Gal, D-Xyl, etc.) analogs formed pyranosides, as evidenced by $^1$H NMR. Similar findings were reported for mono- and oligosaccharide chemoselective ligations with biotinyl, long-chain acyl, peptidyl, and adipyl hydrazides. In contrast, the current chlorambucil study revealed a trend that mirrored that which was observed for the 66-70 subset. Specifically, D-fucoside 72 was formed only as the cyclic compound (67% yield), D-glucuronolactonide 73 and D-xyloside 75 were a mixture of the open and closed conformers (46% and 47%, respectively), and D-threoside 74 adopted the open-chain imine (86%). These results indicate that closure of the glycoside may not only be dependent on the type of sugar but possibly the nature of the aglycon as well. It was also notable that only the β-anomer of the closed-rings was observed while the hydrazyl imines were isolated as mixtures of E- and Z-isomers (FIG. 7).

Anticancer Activity of Chlorambucil N-Hydroxyamino- and N-Acyl Hydrazine-Based Neoglycosides.

Neoglycosides 66-70, 72-75, and their respective aglycons, 65 and 71, were assayed for antiproliferative activity using the same cell lines as 10-63. In general, the alternate handle glycosides did not perform as well as their methoxyamine analogs with the most notable difference being between the 66-70 and 72-75 analogs. While some of the hydroxyamine compounds produced comparable inhibitory responses to the methoxyamine group, 72-75 had universally diminished anticancer properties over 10-63 with average GI50 values 5- to 13-fold greater across the ten-member panel. 6670 and 72-75 were also found to have GI50 values up to 6-fold larger than the corresponding aglycons, though aglycons 65 and 71 were of similar activity to 9 (see Table 5).

Figure 8:
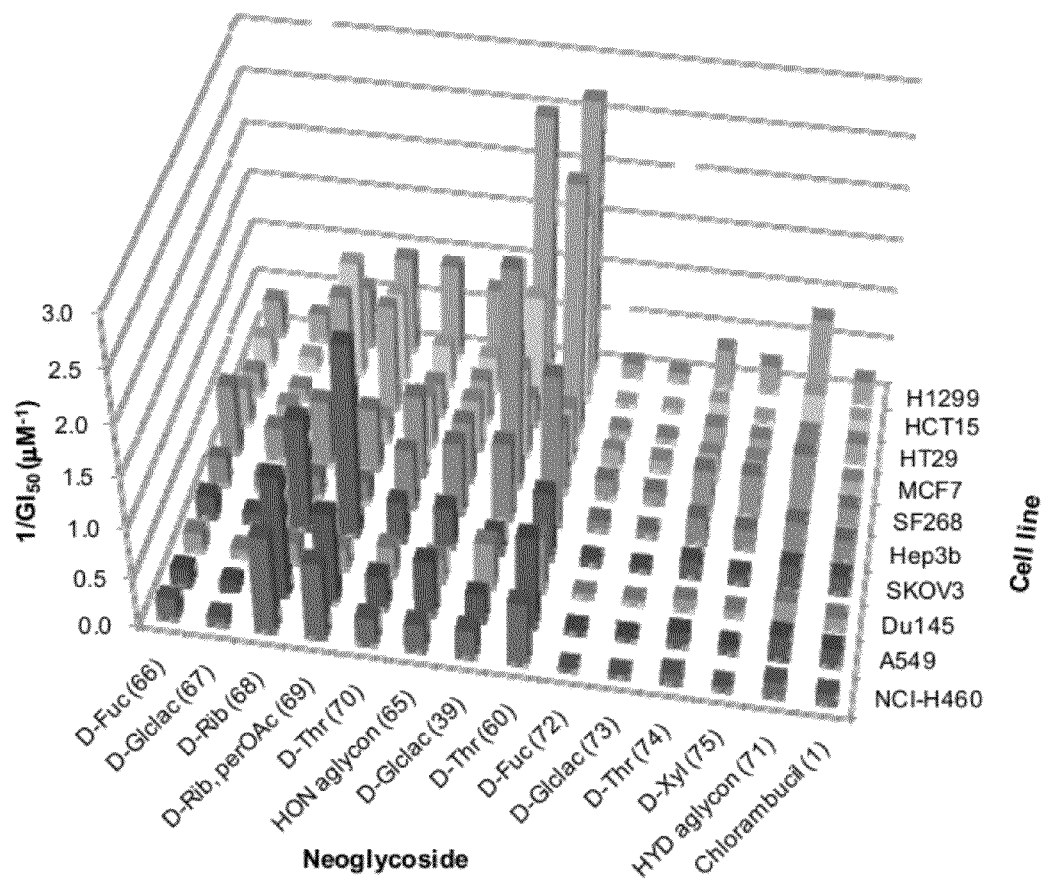
FIG. 8 is a summary of GI50 data from the high-throughput growth inhibition assay of 66-70 hydroxyamines and 72-75 hydrazides (reciprocal values displayed). Comparisons were performed against methoxyamines 39 and 60, aglycons 65 and 71, and chlorambucil (1). GI50 data and error values are provided in the Supporting Information, Table 5. Representative cancer cell lines tested include: NCI-H460 (lung), A549 (lung), Du145 (prostate), SKOV3 (ovary), Hep3b (liver), SF268 (brain), MCF7 (breast), HT29 (colorectal), HCT15 (colorectal), H1299 (lung).
Figure 9:
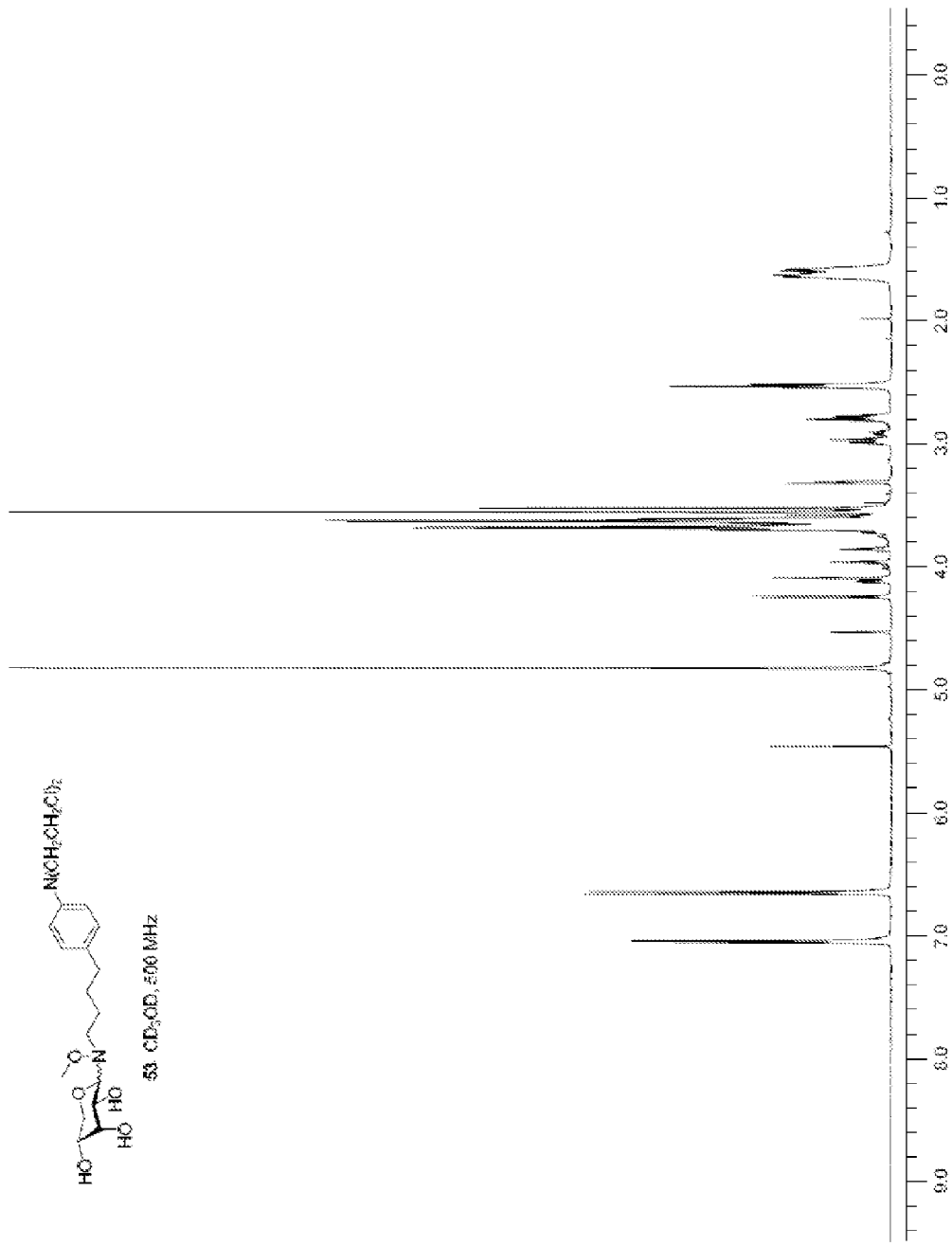
FIG. 9 is an $^1$H NMR spectrum (500 MHz, CD$_3$OD) for a purified sample of compound 53.
Figure 10:
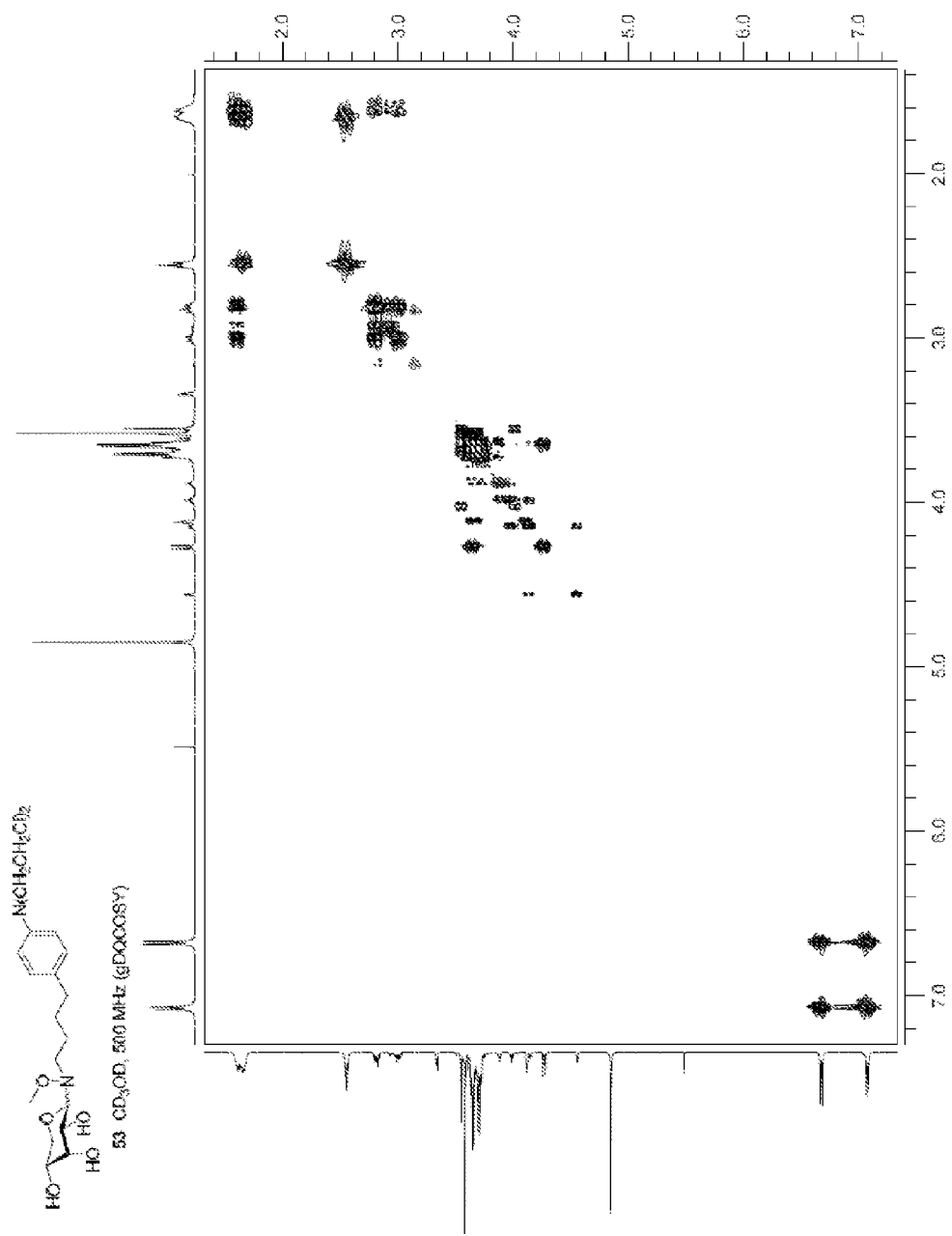
FIG. 10 is a DQCOSY NMR spectrum (500 MHz, CD$_3$OD) for a purified sample of compound 53.
Figure 11:
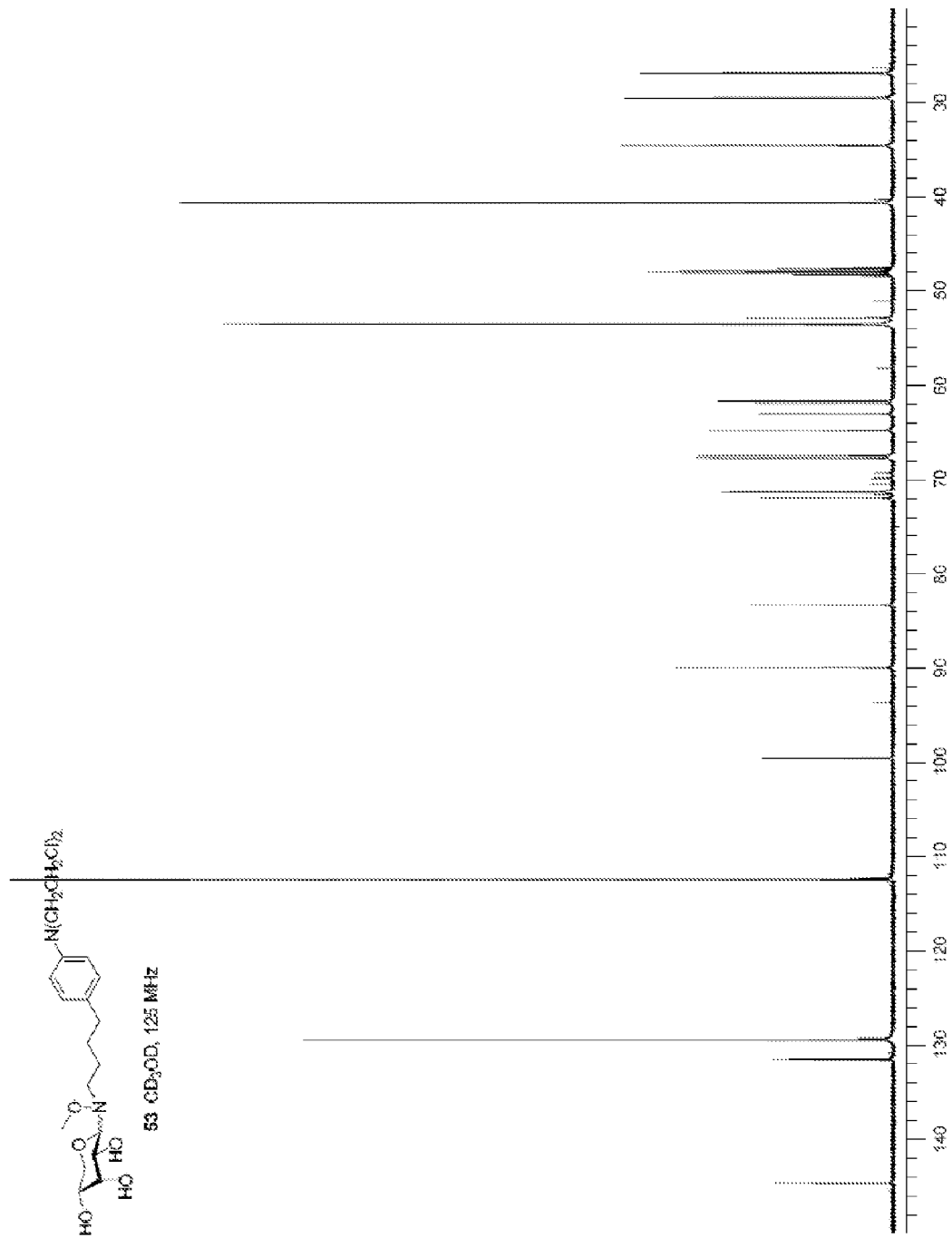
FIG. 11 is a $^{13}$C NMR spectrum (125 MHz, CD$_3$OD) for a purified sample of compound 53.
Figure 12:
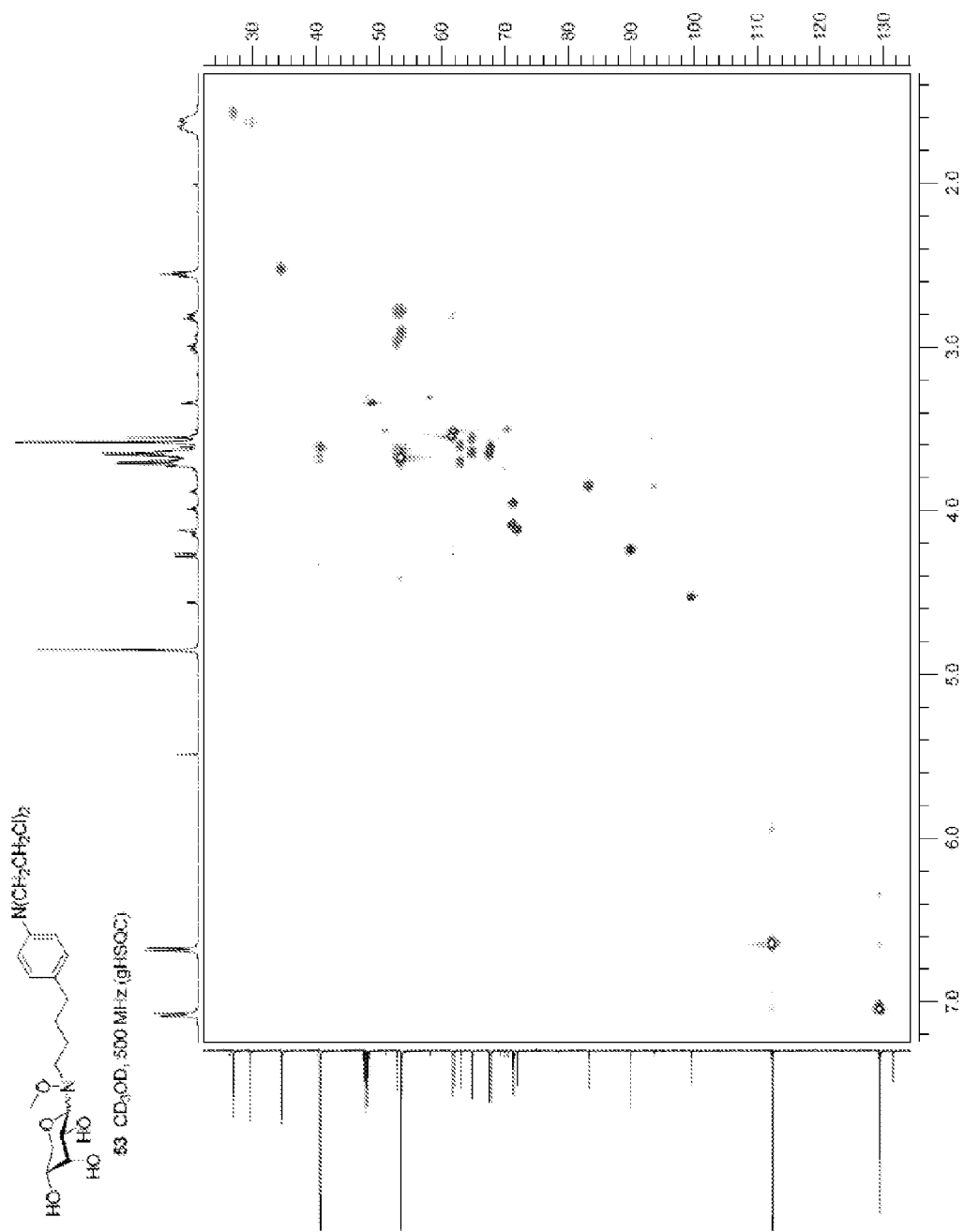
FIG. 12 is an HSQC NMR spectrum (500 MHz, CD$_3$OD) for a purified sample of compound 53.
Figure 13:
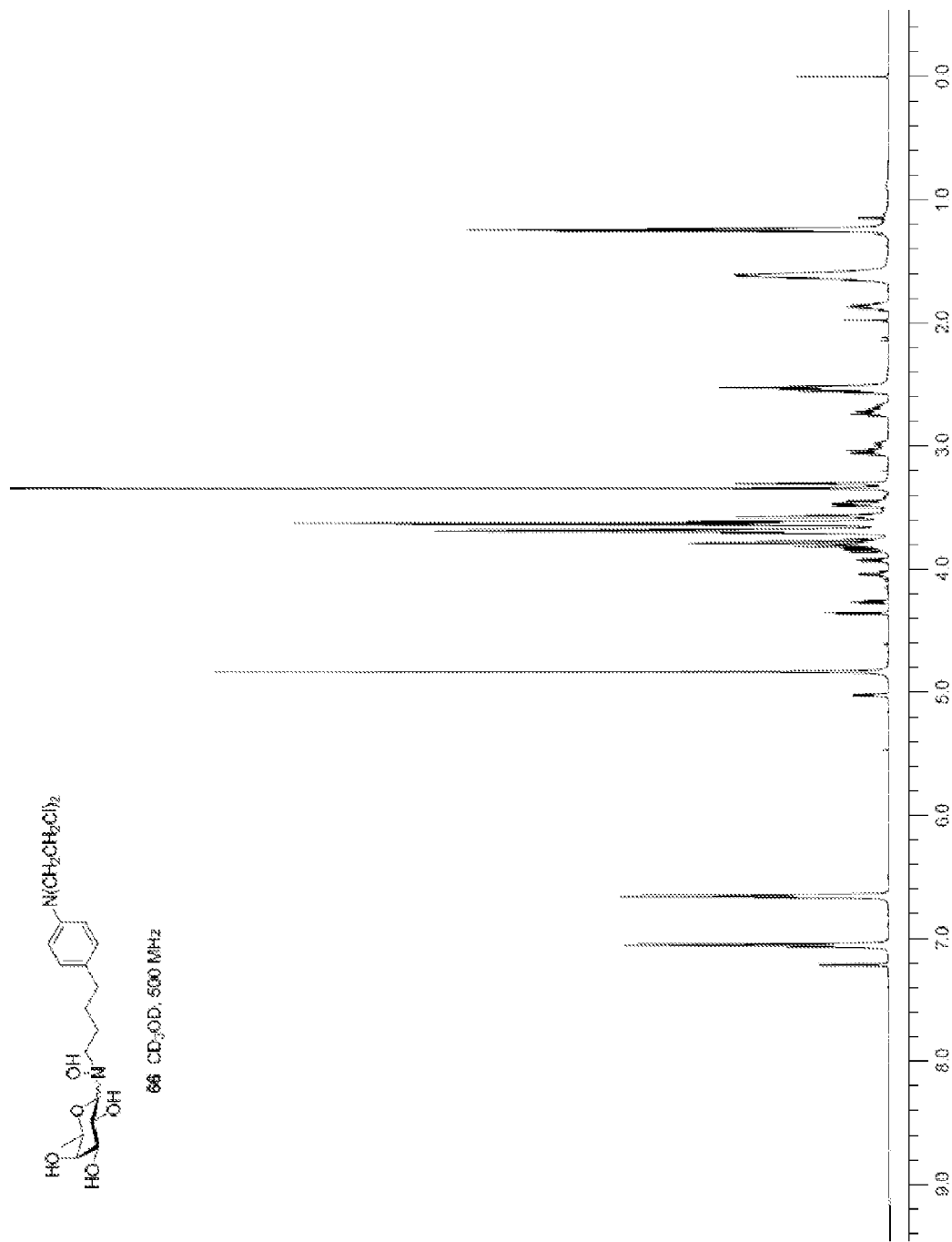
FIG. 13 is an $^1$H NMR spectrum (500 MHz, CD$_3$OD) for a purified sample of compound 66.
Figure 14:
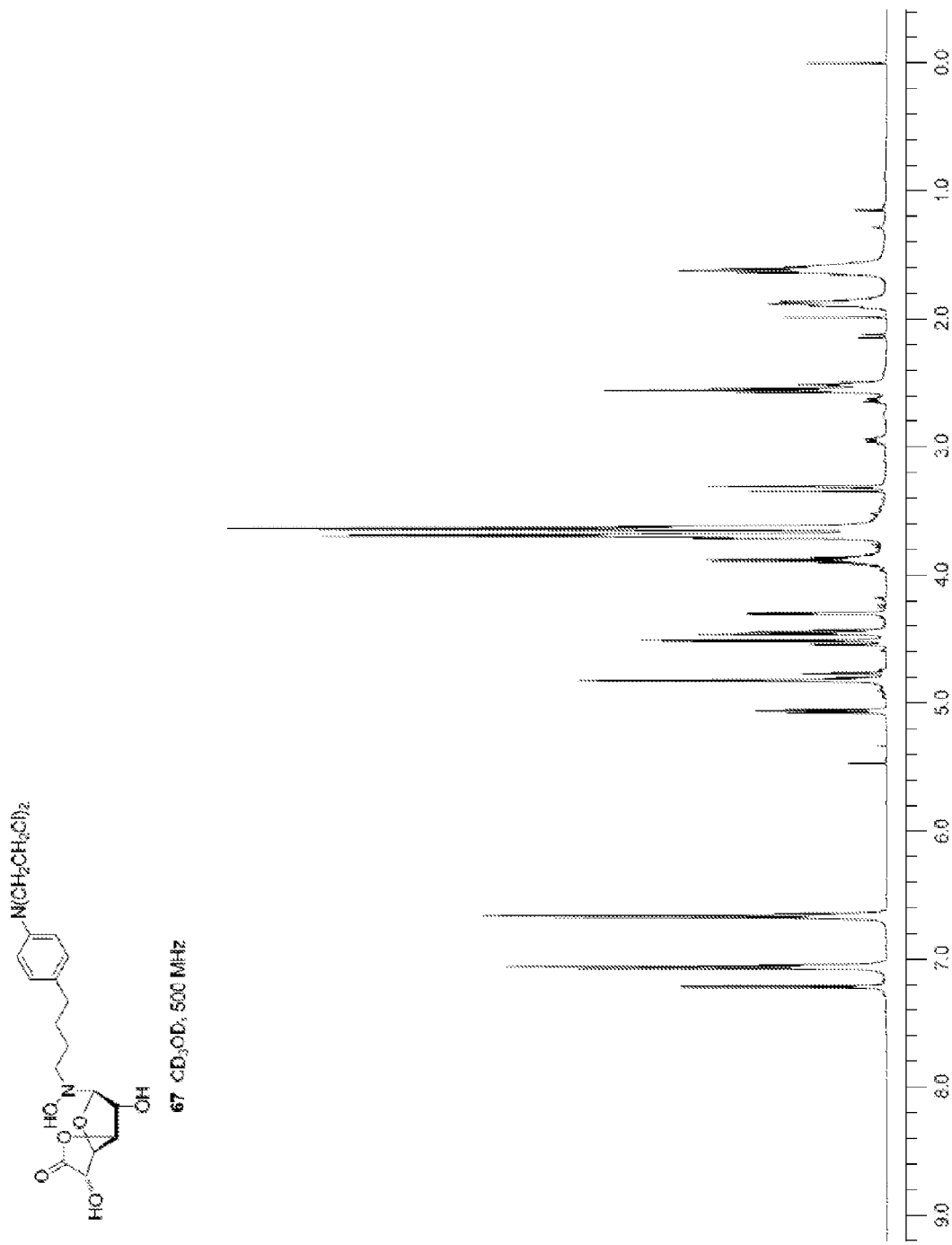
FIG. 14 is an $^1$H NMR spectrum (500 MHz, CD$_3$OD) for a purified sample of compound 67.
Figure 15:
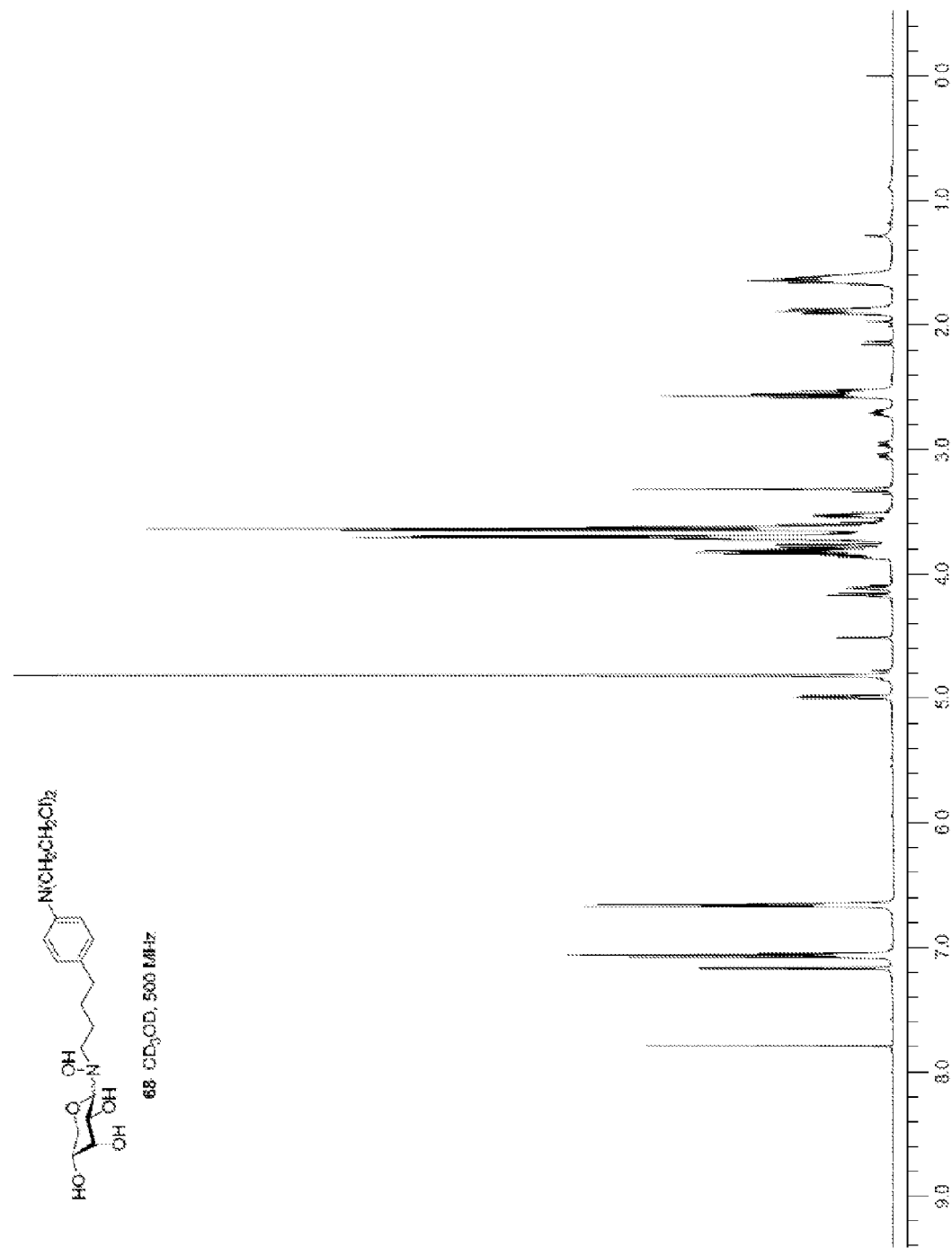
FIG. 15 is an $^1$H NMR spectrum (500 MHz, CD$_3$OD) for a purified sample of compound 68.
Figure 16:
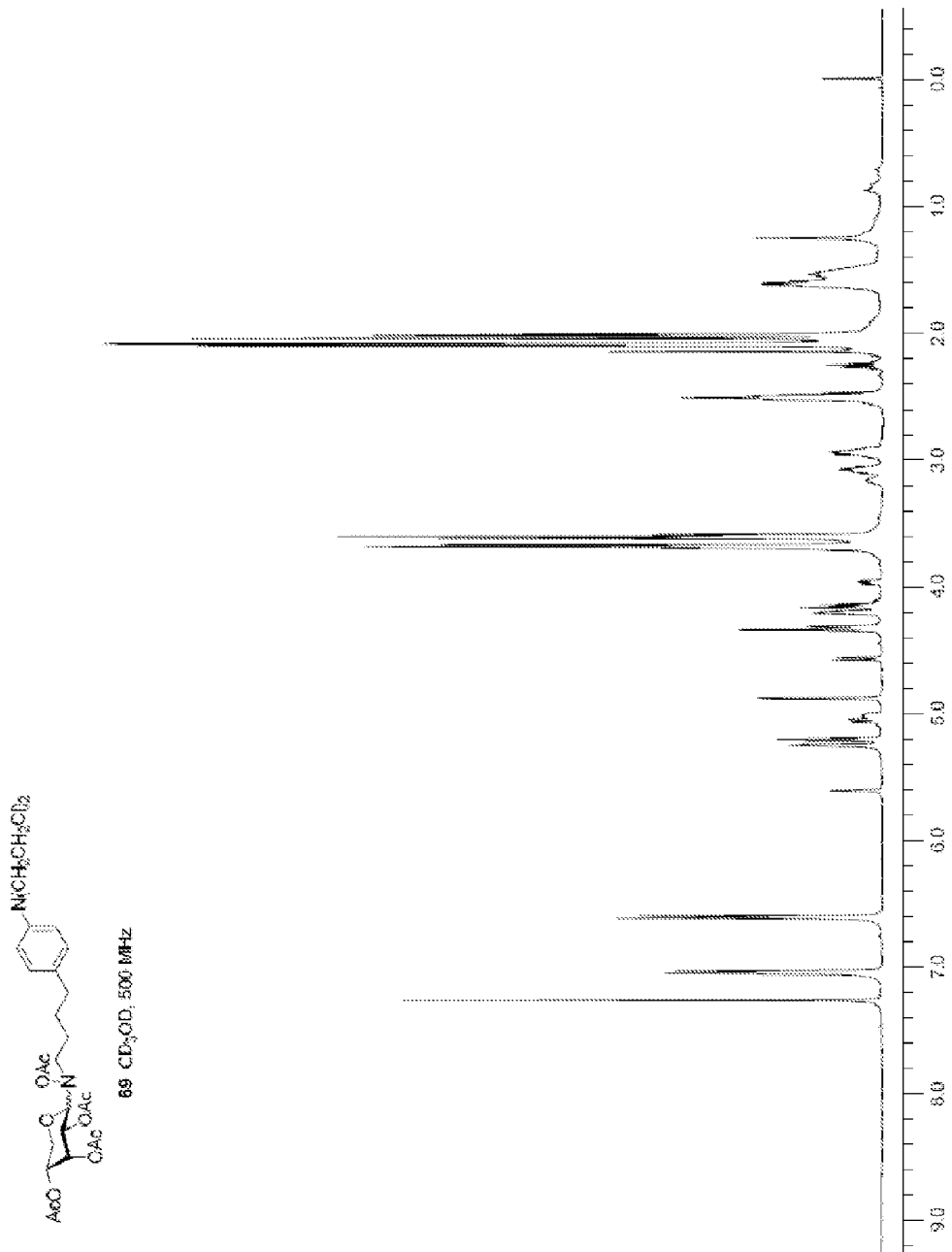
FIG. 16 is an $^1$H NMR spectrum (500 MHz, CD$_3$OD) for a purified sample of compound 69.
Figure 17:
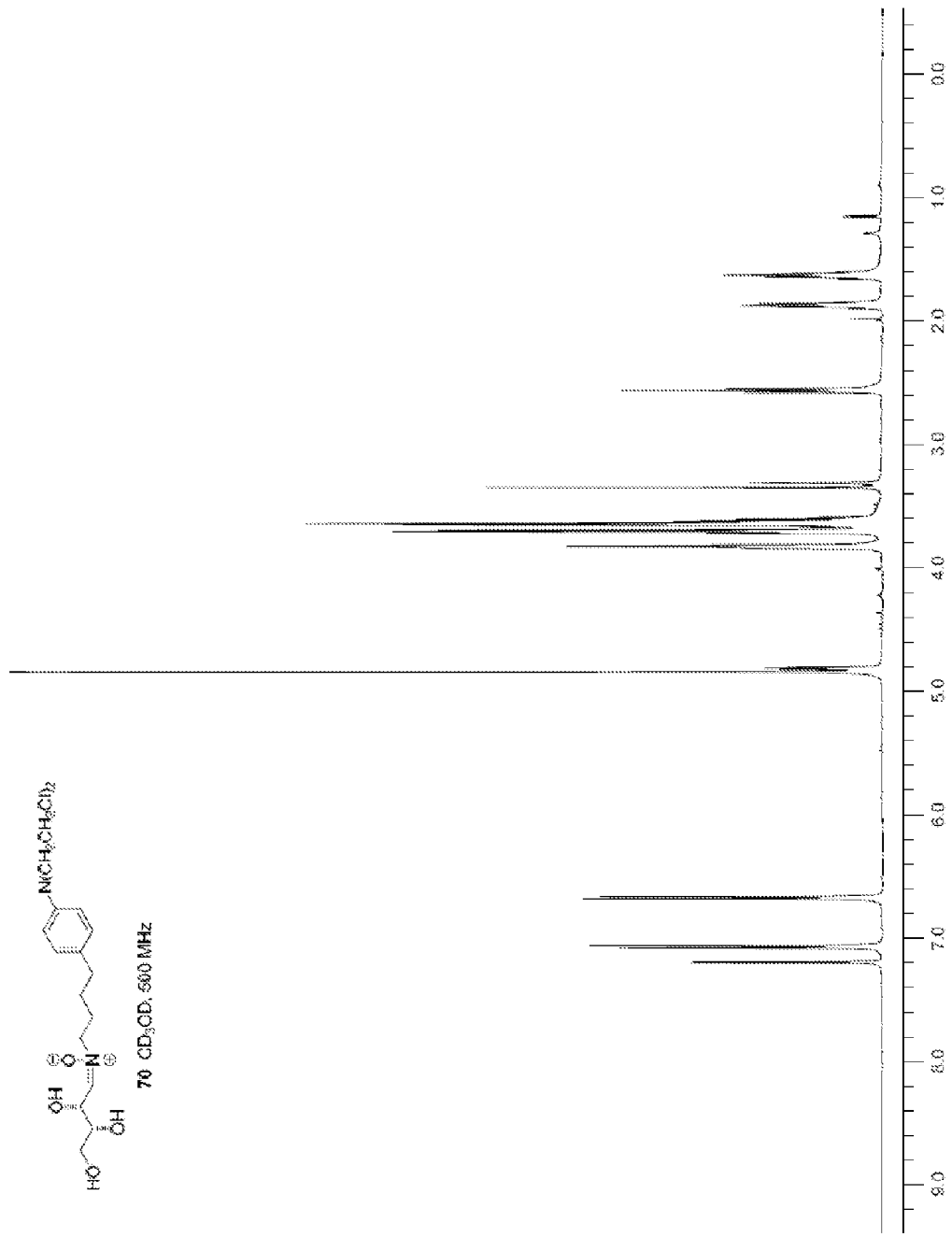
FIG. 17 is an $^1$H NMR spectrum (500 MHz, CD$_3$OD) for a purified sample of compound 70.
Figure 18:
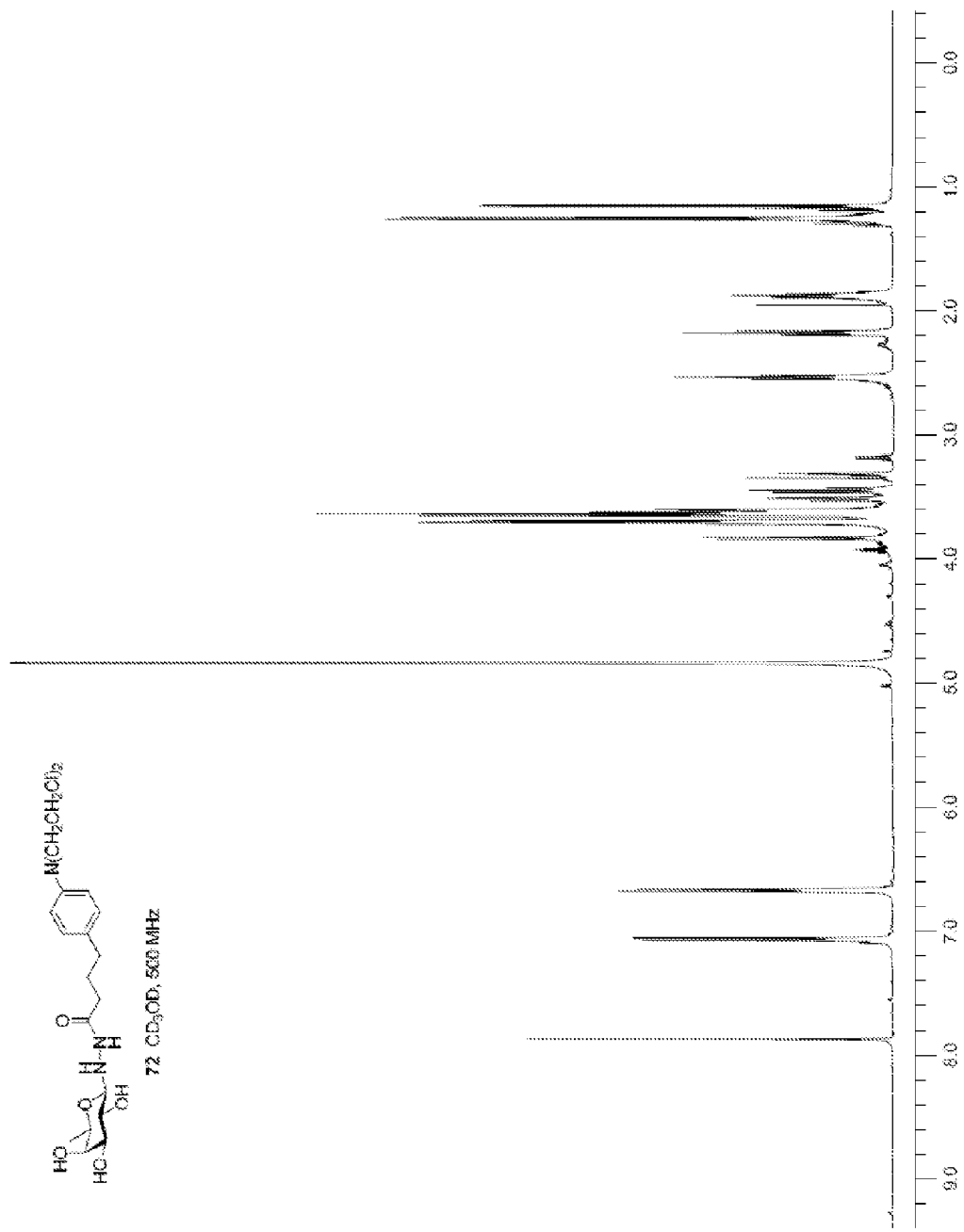
FIG. 18 is an $^1$H NMR spectrum (500 MHz, CD$_3$OD) for a purified sample of compound 72.
Figure 19:
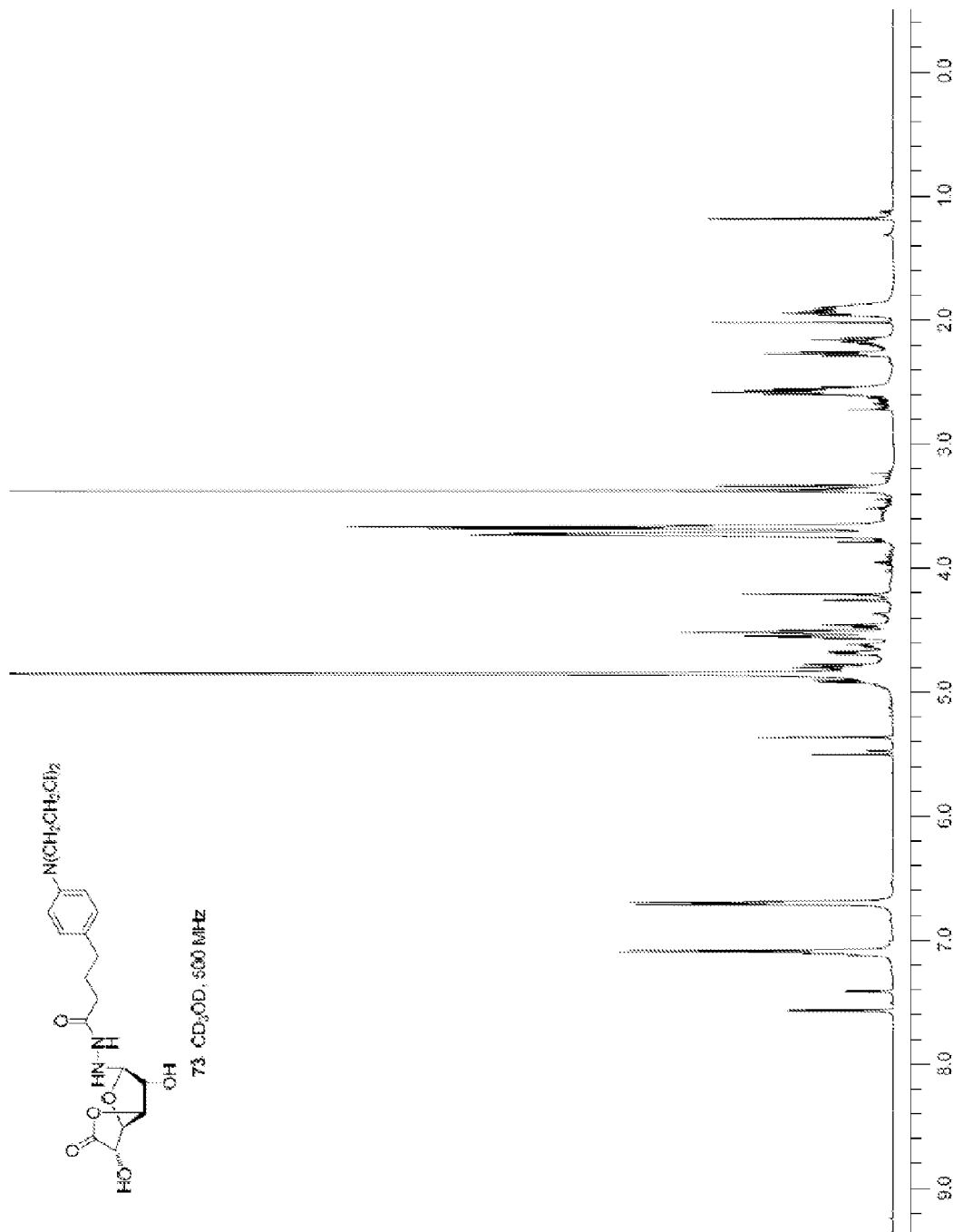
FIG. 19 is an $^1$H NMR spectrum (500 MHz, CD$_3$OD) for a purified sample of compound 73.
Figure 20:
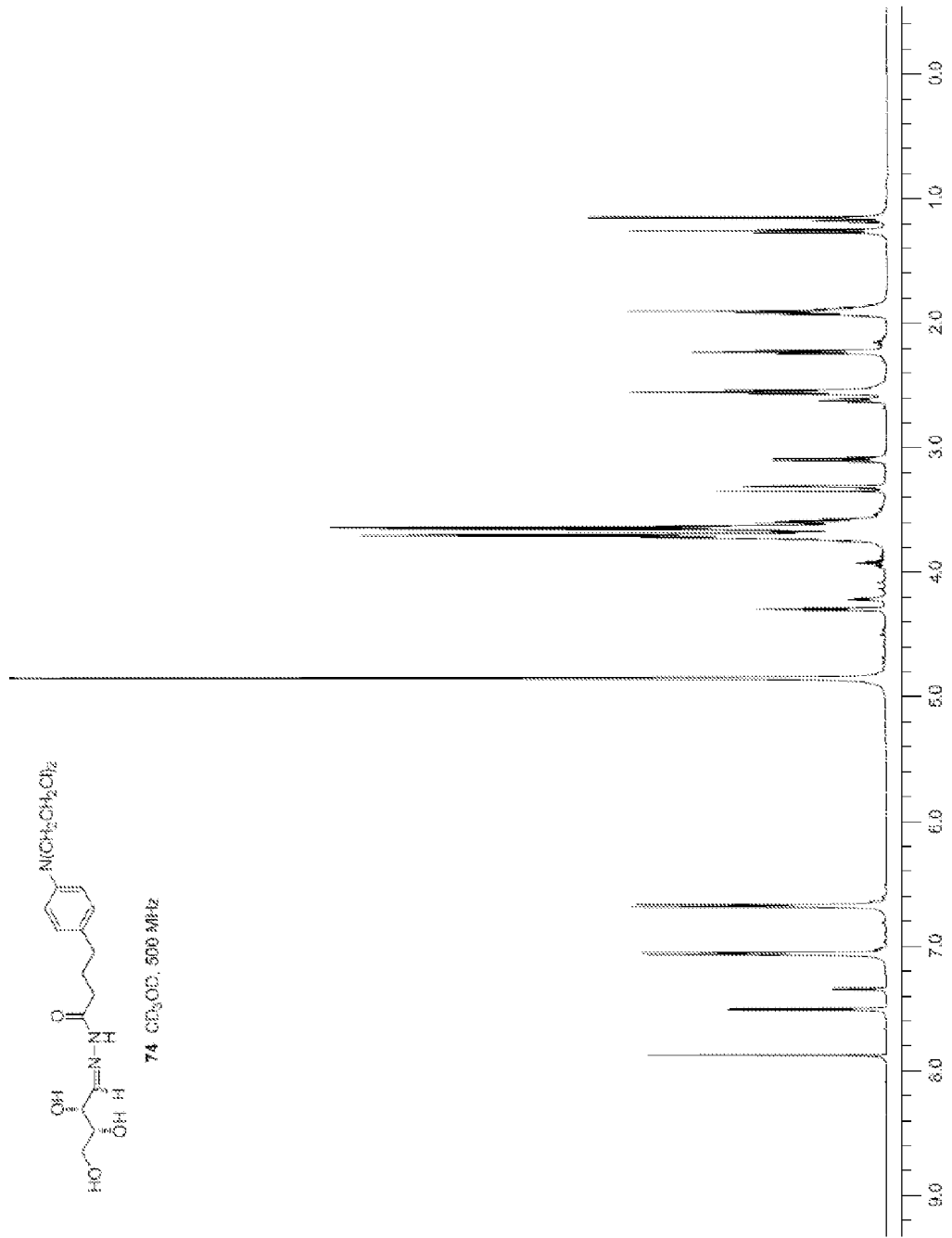
FIG. 20 an $^1$H NMR spectrum (500 MHz, CD$_3$OD) for a purified sample of compound 74.
Figure 21:
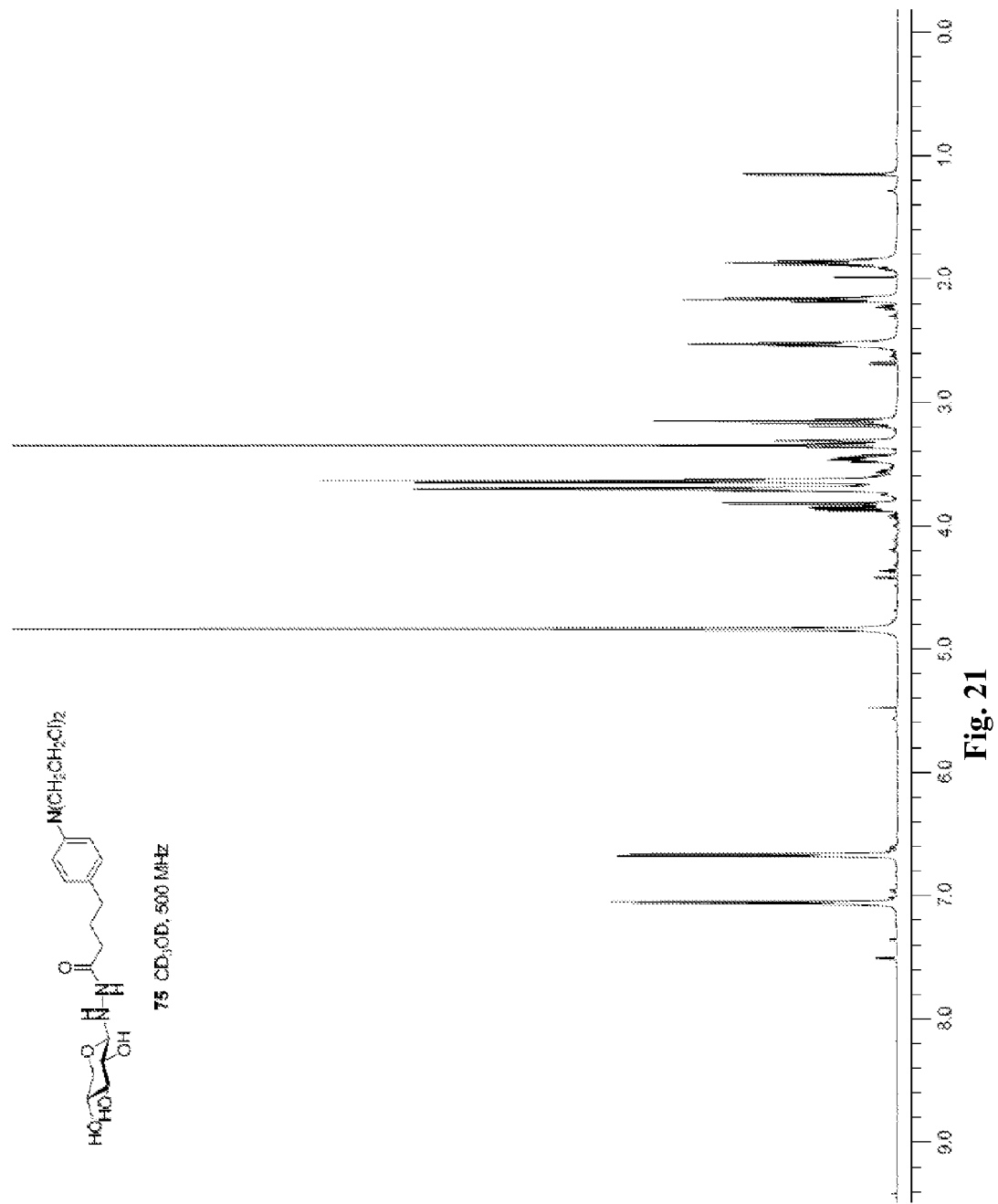
FIG. 21 an NMR spectrum (500 MHz, CD$_3$OD) for a purified sample of compound 75.

Two exceptions to this overall trend, D-riboside 68 and its peracetylated variant 69, were 2- to 5 fold more active than the alkoxyamino-based 53 in six of the ten cell lines (0.53-1.3 μM vs. 1.8-5.9 μM, respectively). 68 and 69 are also notable as among the most active (i.e., mid- to high-nanomolar range) neoglycosides against the SKOV3 ovarian cancer line (see FIG. 8). These data suggest the type of neoglycoside handle employed greatly influences desired activity. When taken into account that aglycons 9, 65, and 71 are of similar potency, the variation in activity between the methoxyamino-, hydroxyamino-, and acyl hydrazine-based neoglycosides implicates the nature of the glycosidic bond to be the most significant contributor, wherein a prevalence of the acyclic nitrone or imine conjugate led to a reduction in potency.

Materials and Methods.

In General.

Mass spectrometric data were obtained on either a Waters (Milford, Mass.) LCT time-of-flight spectrometer for electrospray ionization (ESI) or a Varian ProMALDI (Palo Alto, Calif.) Fourier-transform ion cyclotron resonance mass spectrometer (FTICR) equipped with a 7.0 Tesla actively-shielded superconducting magnet and a Nd-YAG laser. NMR spectra were obtained on a Varian $^{Unity}$Inova 500 MHz instrument (Palo Alto, Calif.) using 99.8% CDCl3 with 0.05% v/v TMS or 99.8% CD₃OD in ampoules. $^1$H and $^{13}$C chemical shifts were referenced to TMS (for CDCl₃) or nondeuterated solvent (for CD₃OD). Multiplicities are indicated by s (singlet), d (doublet), t (triplet), q (quartet), qui (quintet), m (multiplet), and br (broad). Chemical shift assignments for anomeric mixtures, where possible, are noted as α or β with the atom responsible for the shift. $^1$H NMR characterization was supplemented with gCOSY for all neoglycoside library members as well as $^{13}$C and gHSQC for pilot reactions and alternate handle compounds. Tetrahydrofuran was dried using a column of activated alumina. All other solvents were used as provided by the supplier. Reagents were obtained from Aldrich or Sigma and were used as received. Flash chromatography was performed using 40-63 μm particle sized silica gel. Thin layer chromatography was performed on aluminum-backed, 254 nm UV-active plates with a silica gel particle size of 60 μm. Library purity was assessed by reverse phase HPLC using a Varian (Walnut Creek, Calif.) ProStar unit with a Phenomenex (Torrance, Calif.) Luna C18 4.6×250 mm column running a H20/MeCN 90/10 to 10/90 gradient over 13 m, followed by a 5 m isocratic flow, at a rate of 1.0 mL/m., A254 detection. Purity of the neoglycosides and aglycons was assessed to be greater than 95%, unless specified otherwise (see Table 2).

TABLE 5

$GI_{50}$ Cytotoxicity Data of Chlorambucil Neoglycoside Library

| entry | neoglycoside | A549 lung (+p53) | H1299 lung (−p53) | NCI-H460 lung | HCT-15 colorectal |
|---|---|---|---|---|---|
| 10 | D-Alloside | 3.4 ± 0.2[a] | 0.53 ± 0.05 | 9.5 ± 0.7 | 0.97 ± 0.07 |
| 11 | L-Alloside | 3.5 ± 0.2 | 1.3 ± 0.1 | 10.4 ± 0.8 | 1.7 ± 0.1 |
| 12 | D-Altroside | 2.4 ± 0.1 | 0.91 ± 0.05 | 6.6 ± 0.4 | 1.4 ± 0.1 |
| 13 | L-Altroside | 3.1 ± 0.2 | 1.3 ± 0.1 | 7.9 ± 0.5 | 1.4 ± 0.1 |
| 14 | D-Arabinoside | 2.0 ± 0.1 | 0.73 ± 0.03 | 5.0 ± 0.4 | 0.90 ± 0.04 |
| 15 | L-Arabinoside | 2.3 ± 0.2 | 0.84 ± 0.04 | 6.1 ± 0.5 | 1.00 ± 0.05 |
| 16 | D-Arabinoside, 2,3,5-Bn | >100 | >100 | >100 | 64 ± 8 |
| 17 | D-Cellobioside | 1.6 ± 0.1 | 1.8 ± 0.1 | 3.8 ± 0.3 | 2.3 ± 0.1 |
| 18 | D-Digitoxoside | 2.7 ± 0.2 | 1.1 ± 0.1 | 6.5 ± 0.4 | 1.3 ± 0.1 |
| 19 | D-Erythroside | 3.1 ± 0.8 | 1.1 ± 0.1 | 7.8 ± 0.9 | 0.77 ± 0.09 |
| 20 | D-Fucoside | 9.6 ± 0.4 | 3.5 ± 0.2 | 5.9 ± 0.3 | 0.82 ± 0.07 |
| 21 | L-Fucoside | 2.2 ± 0.1 | 1.2 ± 0.1 | 5.4 ± 0.3 | 1.4 ± 0.1 |
| 22 | L-Fucoside, 2,3,4-Bn | 6.4 ± 0.2 | 3.3 ± 0.2 | 15.8 ± 0.7 | 4.6 ± 0.2 |
| 23 | D-Galactoside | 4.4 ± 0.4 | 1.3 ± 0.1 | 9.7 ± 0.8 | 2.4 ± 0.1 |
| 24 | L-Galactoside | 4.8 ± 0.4 | 1.4 ± 0.1 | 10.4 ± 0.7 | 2.3 ± 0.3 |
| 25 | D-Galactoside, 2-deoxy | 3.2 ± 0.2 | 1.5 ± 0.1 | 6.6 ± 0.4 | 1.6 ± 0.1 |
| 26 | D-Galacturonoside | 17.1 ± 0.8 | 4.9 ± 0.7 | 34 ± 2 | 8.1 ± 0.6 |
| 27 | D-GalNAc | 22 ± 1 | 3.8 ± 0.4 | 42 ± 3 | 19.1 ± 0.8 |
| 28 | D-Glucoside | 4.5 ± 0.2 | 1.4 ± 0.1 | 12.3 ± 0.7 | 2.8 ± 0.2 |
| 29 | L-Glucoside | 6.8 ± 0.8 | 1.6 ± 0.1 | 14.3 ± 0.9 | 2.8 ± 0.2 |
| 30 | D-Glucoside, 2-deoxy | 3.1 ± 0.5 | 0.58 ± 0.06 | 5.4 ± 0.6 | 0.70 ± 0.05 |
| 31 | D-Glucoside, 2-fluoro | 2.6 ± 0.1 | 1.2 ± 0.1 | 6.4 ± 0.07 | 1.08 ± 0.04 |
| 32 | D-Glucoside, 3-fluoro | 3.0 ± 0.1 | 1.3 ± 0.1 | 7.1 ± 0.9 | 1.2 ± 0.1 |
| 33 | D-Glucoside, 3-O-Me | 3.6 ± 0.2 | 1.7 ± 0.1 | 7.8 ± 0.08 | 1.1 ± 0.1 |
| 34 | D-Glucoside, 6-amino | 3.7 ± 0.2 | 1.1 ± 0.1 | 5.0 ± 0.4 | 1.3 ± 0.1 |
| 35 | D-Glucoside, 6-N-alloc | 4.5 ± 0.3 | 2.1 ± 0.1 | 11.0 ± 0.1 | 2.1 ± 0.1 |
| 36 | D-Glucoside, 6-chloro | 3.0 ± 0.1 | 1.3 ± 0.1 | 5.8 ± 0.6 | 1.2 ± 0.1 |
| 37 | D-Glucoside, 6-deoxy | 4.6 ± 0.2 | 1.8 ± 0.1 | 8.5 ± 0.8 | 1.1 ± 0.1 |
| 38 | D-Glucuronoside | 5.5 ± 0.3 | 0.99 ± 0.03 | 9.1 ± 0.9 | 1.03 ± 0.05 |
| 39 | D-Glucuronolactonide | 3.7 ± 0.2 | 0.40 ± 0.01 | 3.8 ± 0.3 | 0.99 ± 0.06 |
| 40 | L-Guloside | 3.3 ± 0.2 | 0.55 ± 0.05 | 8.0 ± 0.7 | 0.88 ± 0.07 |
| 41 | D-Lyxoside | 2.3 ± 0.1 | 0.76 ± 0.05 | 5.2 ± 0.4 | 0.79 ± 0.05 |
| 42 | L-Lyxoside | 2.2 ± 0.1 | 0.88 ± 0.04 | 5.8 ± 0.1 | 0.95 ± 0.08 |
| 43 | D-Mannoside | 3.5 ± 0.2 | 1.01 ± 0.07 | 7.8 ± 0.7 | 1.9 ± 0.2 |
| 44 | L-Mannoside | 4.1 ± 0.2 | 1.2 ± 0.1 | 9.8 ± 0.9 | 2.2 ± 0.1 |
| 45 | D-ManNAc | 21 ± 2 | 2.7 ± 0.2 | 33.3 ± 0.5 | 22 ± 2 |
| 46 | D-Gal(1,4)-β-D-Man | 56 ± 1 | 24 ± 1 | 57.7 ± 0.5 | 31 ± 1 |
| 47 | D-Melibioside | 40 ± 2 | 17.8 ± 0.06 | 45.5 ± 0.4 | 20 ± 1 |
| 48 | D-MurNAc | 8.6 ± 0.6 | 2.4 ± 0.2 | 13.1 ± 0.3 | 3.1 ± 0.2 |
| 49 | L-Novioside | 5.8 ± 0.8 | 1.3 ± 0.2 | 9.7 ± 0.5 | 1.7 ± 0.2 |
| 50 | D-Olivoside | 3.1 ± 0.2 | 4.8 ± 0.5 | 5.7 ± 0.6 | 2.5 ± 0.2 |
| 51 | L-Rhamnoside | 2.5 ± 0.1 | 3.7 ± 0.3 | 5.3 ± 0.4 | 2.0 ± 0.1 |
| 52 | L-Rhamnoside, 2,3,4-Ac | 3.5 ± 0.1 | 5.0 ± 0.4 | 7.8 ± 0.8 | 3.7 ± 0.2 |
| 53 | D-Riboside | 2.8 ± 0.1 | 3.6 ± 0.3 | 5.9 ± 0.7 | 1.8 ± 0.1 |
| 54 | L-Riboside | 2.4 ± 0.1 | 3.3 ± 0.2 | 5.7 ± 0.6 | 2.1 ± 0.1 |
| 55 | D-Riboside, 2-deoxy | 2.6 ± 0.2 | 3.7 ± 0.2 | 5.8 ± 0.6 | 2.3 ± 0.1 |
| 56 | L-Riboside, 2-deoxy | 2.5 ± 0.1 | 3.9 ± 0.5 | 5.2 ± 0.6 | 2.2 ± 0.1 |
| 57 | D-Riboside, 2,3,5-Bn | >100 | 82 ± 7 | >100 | >100 |
| 58 | D-Taloside | 2.6 ± 0.1 | 3.0 ± 0.3 | 5.0 ± 0.6 | 2.2 ± 0.1 |
| 59 | L-Taloside | 2.7 ± 0.2 | 2.4 ± 0.2 | 4.3 ± 0.4 | 2.0 ± 0.1 |
| 60 | D-Threoside | 1.1 ± 0.1 | 0.37 ± 0.04 | 1.7 ± 0.4 | 0.53 ± 0.05 |
| 61 | L-Threoside | 2.0 ± 0.2 | 0.72 ± 0.03 | 1.9 ± 0.5 | 0.82 ± 0.05 |
| 62 | D-Xyloside | 2.3 ± 0.1 | 0.83 ± 0.04 | 4.5 ± 0.4 | 0.90 ± 0.05 |
| 63 | L-Xyloside | 2.2 ± 0.1 | 0.93 ± 0.03 | 2.9 ± 0.3 | 0.83 ± 0.04 |
| 1 | Chlorambucil | 6.1 ± 0.3 | 4.9 ± 0.2 | 11.0 ± 0.9 | 8.1 ± 0.1 |
| 9 | Methoxyamine aglycon | 3.2 ± 0.3 | 1.8 ± 0.2 | 4.4 ± 0.5 | 1.1 ± 0.1 |
| 66 | D-Fucoside | 6.4 ± 0.3 | 2.6 ± 0.1 | 4.9 ± 0.2 | 3.8 ± 0.3 |
| 67 | D-Glucuronolactonide | 10.4 ± 0.6 | 3.8 ± 0.1 | 13.1 ± 0.4 | 8.5 ± 0.5 |
| 68 | D-Riboside | 0.84 ± 0.05 | 1.6 ± 0.2 | 1.04 ± 0.06 | 0.87 ± 0.05 |
| 69 | D-Riboside, perOAc | 1.12 ± 0.07 | 1.05 ± 0.05 | 1.3 ± 0.1 | 1.1 ± 0.1 |
| 70 | D-Threoside | 3.0 ± 0.2 | 1.07 ± 0.08 | 3.8 ± 0.1 | 2.5 ± 0.1 |
| 65 | Hydroxyamine aglycon | 1.8 ± 0.1 | 1.4 ± 0.1 | 3.9 ± 0.3 | 3.0 ± 0.2 |
| 72 | D-Fucoside | 28 ± 1 | 8.7 ± 0.3 | 51 ± 2 | >100 |
| 73 | D-Glucuronolactonide | 31 ± 2 | 12.9 ± 0.7 | 43 ± 4 | >100 |
| 74 | D-Threoside | 7.5 ± 0.5 | 2.6 ± 0.2 | 10.8 ± 0.8 | 7.3 ± 0.4 |
| 75 | D-Xyloside | 14.8 ± 0.7 | 3.9 ± 0.2 | 26 ± 3 | >100 |
| 71 | Hydrazide aglycon | 4.3 ± 0.4 | 1.3 ± 0.1 | 6.9 ± 0.6 | 3.0 ± 0.2 |

TABLE 5-continued

GI$_{50}$ Cytotoxicity Data of Chlorambucil Neoglycoside Library

| entry | HT29 colorectal | Hep3b liver | MCF7 breast | DU-145 prostate | SF-268 CNS | SKOV3 ovary |
|---|---|---|---|---|---|---|
| 10 | 0.60 ± 0.9 | 4.4 ± 0.3 | 9.3 ± 0.7 | 5.8 ± 0.1 | 3.1 ± 0.1 | 3.0 ± 0.1 |
| 11 | 2.2 ± 0.1 | 2.5 ± 0.1 | 9.0 ± 0.7 | 6.0 ± 0.1 | 3.2 ± 0.1 | 3.1 ± 0.1 |
| 12 | 1.6 ± 0.2 | 1.7 ± 0.1 | 6.5 ± 0.1 | 4.1 ± 0.2 | 1.9 ± 0.1 | 1.9 ± 0.1 |
| 13 | 2.1 ± 0.2 | 2.0 ± 0.1 | 7.9 ± 0.8 | 4.1 ± 0.1 | 2.3 ± 0.1 | 2.5 ± 0.1 |
| 14 | 1.5 ± 0.2 | 1.6 ± 0.1 | 4.6 ± 0.1 | 3.3 ± 0.1 | 1.8 ± 0.1 | 2.0 ± 0.1 |
| 15 | 1.9 ± 0.1 | 1.9 ± 0.1 | 5.4 ± 0.1 | 3.6 ± 0.1 | 1.9 ± 0.1 | 2.2 ± 0.1 |
| 16 | 47 ± 1 | >100 | 82 ± 1 | >100 | 80 ± 5 | >100 |
| 17 | 1.9 ± 0.1 | 1.2 ± 0.1 | 1.7 ± 0.1 | 1.8 ± 0.1 | 1.5 ± 0.1 | 1.8 ± 0.1 |
| 18 | 2.1 ± 0.09 | 3.2 ± 0.1 | 6.3 ± 0.1 | 4.3 ± 0.1 | 2.8 ± 0.1 | 3.0 ± 0.1 |
| 19 | 1.6 ± 0.1 | 4.1 ± 0.9 | 8.0 ± 0.1 | 5.0 ± 0.7 | 2.4 ± 0.8 | 2.6 ± 0.9 |
| 20 | 6.7 ± 0.3 | 2.6 ± 0.2 | 3.0 ± 0.2 | 4.1 ± 0.9 | 1.7 ± 0.1 | 1.7 ± 0.1 |
| 21 | 2.3 ± 0.1 | 3.0 ± 0.1 | 0.78 ± 0.09 | 3.8 ± 0.1 | 2.0 ± 0.1 | 1.8 ± 0.1 |
| 22 | 7.5 ± 0.3 | 9.5 ± 0.4 | 4 ± 1 | 10.0 ± 0.4 | 5.7 ± 0.2 | 7.2 ± 0.4 |
| 23 | 3.3 ± 0.4 | 3.6 ± 0.3 | 1.3 ± 0.2 | 5.6 ± 0.3 | 1.9 ± 0.5 | 3.4 ± 0.5 |
| 24 | 3.7 ± 0.5 | 3.8 ± 0.3 | 1.3 ± 0.1 | 5.5 ± 0.2 | 2.0 ± 0.4 | 4.1 ± 0.6 |
| 25 | 3.5 ± 0.7 | 3.3 ± 0.1 | 1.04 ± 0.08 | 5.0 ± 0.7 | 2.2 ± 0.1 | 2.4 ± 0.1 |
| 26 | 14.9 ± 0.1 | 14.7 ± 0.8 | 4.5 ± 0.5 | 16.3 ± 0.5 | 8.9 ± 0.4 | 12.8 ± 0.5 |
| 27 | 12 ± 1 | 11.8 ± 0.4 | 4.4 ± 0.6 | 16.7 ± 0.7 | 4.2 ± 0.4 | 11 ± 1 |
| 28 | 2.9 ± 0.4 | 3.4 ± 0.1 | 1.5 ± 0.1 | 5.5 ± 0.2 | 1.8 ± 0.1 | 3.0 ± 0.1 |
| 29 | 4.6 ± 0.4 | 5.0 ± 0.6 | 1.8 ± 0.2 | 7.0 ± 0.5 | 2.2 ± 0.1 | 4.5 ± 0.6 |
| 30 | 1.2 ± 0.2 | 3.7 ± 0.3 | 5.4 ± 0.1 | 4.3 ± 0.3 | 2.5 ± 0.5 | 1.12 ± 0.1 |
| 31 | 2.4 ± 0.2 | 3.2 ± 0.1 | 7.3 ± 0.1 | 4.2 ± 0.1 | 2.2 ± 0.1 | 2.0 ± 0.1 |
| 32 | 2.6 ± 0.2 | 3.2 ± 0.1 | 7.0 ± 0.8 | 4.1 ± 0.1 | 2.2 ± 0.1 | 2.2 ± 0.1 |
| 33 | 2.7 ± 0.2 | 4.2 ± 0.2 | 8.3 ± 0.1 | 5.1 ± 0.1 | 2.8 ± 0.1 | 2.4 ± 0.1 |
| 34 | 2.5 ± 0.1 | 3.5 ± 0.2 | 3.7 ± 0.4 | 2.8 ± 0.1 | 2.2 ± 0.1 | 2.2 ± 0.1 |
| 35 | 2.8 ± 0.2 | 4.6 ± 0.2 | 7.4 ± 0.1 | 6.2 ± 0.4 | 3.1 ± 0.1 | 2.9 ± 0.1 |
| 36 | 2.1 ± 0.1 | 3.2 ± 0.2 | 4.9 ± 0.1 | 3.7 ± 0.1 | 2.1 ± 0.1 | 2.1 ± 0.1 |
| 37 | 2.2 ± 0.2 | 4.4 ± 0.3 | 5.8 ± 0.1 | 4.9 ± 0.1 | 2.9 ± 0.1 | 2.9 ± .0.1 |
| 38 | 3.2 ± 0.3 | 4.9 ± 0.3 | 6.0 ± 0.1 | 3.9 ± 0.1 | 1.6 ± 0.1 | 3.1 ± 0.1 |
| 39 | 3.6 ± 0.1 | 1.3 ± 0.1 | 1.1 ± 0.1 | 1.9 ± 0.1 | 0.46 ± 0.02 | 5.2 ± 0.1 |
| 40 | 2.9 ± 0.1 | 3.9 ± 0.2 | 3.2 ± 0.3 | 4.8 ± 0.1 | 2.0 ± 0.1 | 2.5 ± 0.1 |
| 41 | 2.0 ± 0.1 | 2.5 ± 0.1 | 1.0 ± 0.2 | 3.6 ± 0.1 | 1.6 ± 0.1 | 1.8 ± 0.1 |
| 42 | 2.4 ± 0.1 | 3.0 ± 0.1 | 0.94 ± 0.2 | 3.9 ± 0.1 | 1.2 ± 0.1 | 1.8 ± 0.1 |
| 43 | 2.6 ± 0.2 | 3.2 ± 0.2 | 1.9 ± 0.1 | 5.1 ± 0.2 | 1.8 ± 0.1 | 2.3 ± 0.1 |
| 44 | 3.4 ± 0.2 | 3.7 ± 0.2 | 2.2 ± 0.2 | 4.9 ± 0.1 | 2.0 ± 0.1 | 2.9 ± 0.1 |
| 45 | 8.7 ± 0.7 | 9.8 ± 0.7 | 9 ± 1 | 16 ± 1 | 3.4 ± 0.2 | 10.1 ± 0.9 |
| 46 | 34 ± 3 | 38 ± 2 | 26 ± 2 | 43 ± 3 | 19.1 ± 0.7 | 35 ± 1 |
| 47 | 27.4 ± 0.3 | 29 ± 3 | 21 ± 2 | 36 ± 1 | 16.3 ± 0.5 | 27 ± 1 |
| 48 | 6.3 ± 0.3 | 8.0 ± 0.4 | 4.5 ± 0.3 | 8.9 ± 0.3 | 4.1 ± 0.1 | 7.0 ± 0.2 |
| 49 | 6.0 ± 0.1 | 6 ± 1 | 4.8 ± 0.9 | 6.7 ± 0.5 | 5.1 ± 0.8 | 5.4 ± 0.8 |
| 50 | 3.2 ± 0.2 | 3.8 ± 0.2 | 3.1 ± 0.2 | 5.5 ± 0.1 | 2.3 ± 0.8 | 3.2 ± 0.1 |
| 51 | 2.4 ± 0.1 | 2.6 ± 0.1 | 2.2 ± 0.2 | 4.2 ± 0.1 | 1.9 ± 0.1 | 2.0 ± 0.1 |
| 52 | 4.3 ± 0.2 | 4.6 ± 0.2 | 3.2 ± 0.6 | 4.5 ± 0.1 | 3.0 ± 0.1 | 3.9 ± 0.1 |
| 53 | 2.3 ± 0.1 | 2.4 ± 0.1 | 1.1 ± 0.1 | 3.8 ± 0.6 | 1.9 ± 0.1 | 2.0 ± 0.1 |
| 54 | 2.2 ± 0.1 | 2.4 ± 0.1 | 0.97 ± 0.02 | 3.7 ± 0.1 | 2.1 ± 0.2 | 2.0 ± 0.1 |
| 55 | 2.6 ± 0.1 | 2.6 ± 0.1 | 0.96 ± 0.02 | 4.0 ± 0.1 | 2.1 ± 0.1 | 2.0 ± 0.1 |
| 56 | 2.3 ± 0.1 | 2.5 ± 0.1 | 1.3 ± 0.2 | 3.3 ± 0.1 | 2.0 ± 0.1 | 2.2 ± 0.1 |
| 57 | >100 | >100 | >100 | >100 | >100 | >100 |
| 58 | 1.8 ± 0.4 | 2.4 ± 0.1 | 1.5 ± 0.3 | 3.3 ± 0.1 | 1.7 ± 0.1 | 2.0 ± 0.1 |
| 59 | 1.9 ± 0.1 | 2.6 ± 0.1 | 1.8 ± 0.3 | 3.4 ± 0.1 | 1.7 ± 0.1 | 2.0 ± 0.1 |
| 60 | 0.41 ± 0.06 | 0.67 ± 0.06 | 1.8 ± 0.1 | 1.8 ± 0.1 | 1.5 ± 0.1 | 1.5 ± 0.1 |
| 61 | 1.2 ± 0.1 | 1.4 ± 0.1 | 0.87 ± 0.09 | 2.1 ± 0.1 | 1.3 ± 0.1 | 2.1 ± 0.1 |
| 62 | 1.6 ± 0.1 | 1.5 ± 0.1 | 0.91 ± 0.09 | 2.3 ± 0.1 | 1.4 ± 0.1 | 2.2 ± 0.1 |
| 63 | 1.5 ± 0.1 | 1.6 ± 0.1 | 1.2 ± 0.2 | 2.2 ± 0.1 | 1.5 ± 0.1 | 2.4 ± 0.1 |
| 1 | 5.0 ± 0.3 | 5.1 ± 0.2 | 8.2 ± 0.2 | 9.4 ± 0.2 | 5.4 ± 0.1 | 5.5 ± 0.4 |
| 9 | 2.3 ± 0.2 | 2.3 ± 0.4 | 1.9 ± 0.4 | 3.2 ± 0.2 | 1.7 ± 0.3 | 2.9 ± 0.2 |
| 66 | 4.6 ± 0.1 | 3.6 ± 0.3 | 2.7 ± 0.1 | 5.7 ± 0.4 | 1.4 ± 0.1 | 4.7 ± 0.1 |
| 67 | 9.9 ± 0.2 | 7.2 ± 0.3 | 4.1 ± 0.2 | 14.8 ± 0.8 | 3.1 ± 0.1 | 10.1 ± 0.4 |
| 68 | 0.90 ± 0.05 | >5 | 3.2 ± 0.2 | >5 | 1.5 ± 0.1 | 0.89 ± 0.04 |
| 69 | 0.96 ± 0.07 | >5 | 4.6 ± 0.3 | >5 | 1.6 ± 0.1 | 0.53 ± 0.01 |
| 70 | 3.2 ± 0.1 | 1.7 ± 0.1 | 2.0 ± 0.1 | 3.6 ± 0.2 | 1.2 ± 0.1 | 2.6 ± 0.1 |
| 65 | 2.5 ± 0.01 | 1.4 ± 0.1 | 2.0 ± 0.1 | 4.4 ± 0.3 | 1.6 ± 0.1 | 2.6 ± 0.1 |
| 72 | 16.7 ± 0.7 | 11.0 ± 0.3 | 6.3 ± 0.2 | 24 ± 2 | 5.8 ± 0.1 | 22 ± 1 |
| 73 | 30 ± 2 | 17.7 ± 0.4 | 9.9 ± 0.5 | 23 ± 2 | 8.9 ± 0.4 | 37 ± 2 |
| 74 | 4.8 ± 0.1 | 4.1 ± 0.4 | 4.2 ± 0.2 | 9.5 ± 0.7 | 2.6 ± 0.2 | 6.2 ± 0.6 |
| 75 | 7.2 ± 0.1 | 5.5 ± 0.4 | 4.5 ± 0.2 | 19 ± 2 | 2.5 ± 0.1 | 12.0 ± 0.5 |
| 71 | 4.2 ± 0.1 | 3.1 ± 0.1 | 2.3 ± 0.1 | 4.8 ± 0.3 | 1.5 ± 0.1 | 4.3 ± 0.2 |

[a]All values in μM.

N,O-Dimethyl 4-(4-N',N'-bis(2-chloroethyl)amino) phenylbutanamide (6)

Chlorambucil (1, 516 mg, 1.70 mmol) was dissolved in $CH_2Cl_2$ (15 mL) and cooled to 0° C. before adding N,O dimethylhydroxylamine HCl (181 mg, 1.86 mmol) and N-methylmorpholine (200 µL, 1.82 mmol). The coupling agent EDAC (347 mg, 1.81 mmol) was then added to the reaction slowly over 5 min to ensure dissolution. After 60 min, the reaction was quenched with 5% HCl (20 mL) and the acidic layer extracted with $CH_2Cl_2$ (20 mL). The organic layers were combined, washed with sat. aq. $NaHCO_3$ (20 mL) and the basic layer extracted with $CH_2Cl_2$ (20 mL). After combining the organic layers, washing with brine (20 mL), and drying with $Na_2SO_4$, solvent removal yielded a colorless oil (571 mg, 97%, $R_f$=0.23 EtOAc:Hex 1:2) that was used without further purification. $^1H$ NMR ($CDCl_3$, 500 MHz) δ 7.09 (d, J=8.8 Hz, 2H), 6.62 (d, J=8.8 Hz, 2H), 3.71-3.65 (m, 4H), 3.64 (s, 3H), 3.62-3.59 (m, 4H), 3.17 (s, 3H), 2.58 (t, J=7.7 Hz, 2H), 2.44 (t, J=7.0 Hz, 2H), 1.95-1.88 (m, 2H); $^{13}C$ NMR ($CDCl_3$, 125 MHz) δ 144.37, 131.17, 129.80, 112.31, 61.30, 53.74, 40.69, 34.33, 32.29, 31.35, 26.44; HRMS (ESI) m/z for $C_{16}H_{25}Cl_2N_2O_2$ ($[M+H]^+$) 347.1295, calc. 347.1288.

4-(4-N',N'-bis(2-chloroethyl)amino)phenylbutanal (7)

Weinreb amide 6 (571 mg, 1.64 mmol) was dissolved in anhydrous THF (8 mL) under Ar and cooled to 0° C. A suspension of lithium aluminum hydride in anhydrous THF (1.0 M, 1 mL) was added in one aliquot. After 5 min, the reaction was quenched with sat. aq. $KHSO_4$ (5 mL) followed by deionized water (5 mL). Extraction of the aldehyde was performed with $Et_2O$ (2×15 mL) and the organic layer was dried with $Na_2SO_4$. Solvent evaporation provided a yellowish oil (334 mg, 70%, $R_f$=0.65 EtOAc:Hex 1:2). $^1H$ NMR ($CDCl_3$, 500 MHz) δ 9.80 (s, 1H), 7.13 (d, J=8.8 Hz, 2H), 6.70 (d, J=8.8 Hz, 2H), 3.77-3.74 (m, 4H), 3.69-3.66 (m, 4H), 2.63 (t, J=7.6 Hz, 2H), 2.49 (td, J=7.3, 1.5 Hz, 2H), 2.00-1.94 (m, 2H); $^{13}C$ NMR ($CDCl_3$, 125 MHz) δ 202.42, 144.46, 130.37, 129.69, 112.23, 53.56, 43.16, 40.60, 33.91, 23.93; HRMS (MALDI) m/z for $C_{14}H_{20}Cl_2NO$ ($[M+H]^+$) 288.09091, calc. 288.09165.

N-Methoxy-4-(4-N',N'-bis(2-chloroethyl)amino) phenylbutanimine (8)

Aldehyde 6 (334 mg, 1.16 mmol) was dissolved in absolute EtOH (10 mL) followed by the addition of $MeONH_2.HCl$ (247 mg, 2.95 mmol) and $Et_3N$ (400 µL, 2.87 mmol). After 35 min, the solvent was removed in vacuo, providing the crude product as a white crystalline solid. The material was suspended in EtOAc:Hex 1:7 (50 mL) and filtered through a silica gel plug, which was flushed with solvent (400 mL). The purified imine was provided as a colorless oil containing a mixture of E- and Z-isomers (308 mg, 84%, $R_{fA}$=0.51 $R_{fB}$=0.43 EtOAc:Hex 1:7). $^1H$ NMR ($CDCl_3$, 500 MHz) δ 7.36 (t, J=6.2 Hz, 1H), 7.05 (d, J=8.8 Hz, 2H), 6.61 (d, J=8.8 Hz, 2H), 3.80 (s, 3H), 3.69-3.65 (m, 4H), 3.61-3.57 (m, 4H), 2.55 (t, J=7.7 Hz, 2H), 2.18 (q, J=7.7 Hz, 2H), 1.75 (qui, J=7.7 Hz, 2H); $^{13}C$ NMR ($CDCl_3$, 125 MHz) δ 150.58, 144.38, 130.87, 129.74, 112.28, 61.27, 53.67, 40.61, 34.14, 29.03, 28.72; HRMS (ESI) m/z for $C_{15}H_{23}Cl_2N_2O$ ($[M+H]^+$) 317.1187, calc. 317.1182.

N-Methoxy-4-(4-N',N'-bis(2-chloroethyl)amino) phenylbutylamine (9)

Imine 8 (308 mg, 0.971 mmol) was dissolved in absolute EtOH (15 mL), cooled to 0° C., and the reducing agent $BH_3.Et_3N$ (710 µL, 4.83 mmol) was added in one aliquot. Concentrated HCl:EtOH 1:1 (800 µL) was then dripped in slowly over 5 min. The reaction was quenched with sat. aq. $NaHCO_3$ (5 mL), 5 min after the acid solution was completely added, resulting in a white slurry. The organic solvent was removed under reduced pressure then more $NaHCO_3$ (5 mL) solution was added. The aqueous material was extracted with $CH_2Cl_2$ (3×20 mL) and dried with $Na_2SO_4$. The crude oil was purified by flash chromatography ($SiO_2$, EtOAc:Hex 1:2) providing the aglycon as a colorless oil (200 mg, 65%, $R_f$=0.37 EtOAc:Hex 1:2). NMR ($CDCl_3$, 500 MHz) δ 7.05 (d, J=8.6 Hz, 2H), 6.60 (d, J=8.7 Hz, 2H), 5.50 (s br, 1H), 3.69-3.65 (m, 4H), 3.61-3.57 (m, 4H), 3.50 (s, 3H), 2.91 (t, J=7.1 Hz, 2H), 2.53 (t, J=7.5 Hz, 2H), 1.61-1.58 (m, 2H), 1.55-1.49 (m, 2H); $^{13}C$ NMR ($CDCl_3$, 125 MHz) δ 144.20, 131.63, 129.62, 112.22, 61.80, 53.65, 51.80, 40.61, 34.66, 29.32, 26.98; HRMS (ESI) m/z for $C_{15}H_{25}Cl_2N_2O$ ($[M+H]^+$) 319.1334, calc. 319.1339.

N-Hydroxy-4-(4-N',N'-bis(2-chloroethyl)amino) phenylbutanimine (64)

Aldehyde 7 (442 mg, 1.53 mmol) was dissolved in absolute EtOH (10 mL) followed by the addition of $HONH_2.HCl$ (269 mg, 3.87 mmol) and $Et_3N$ (550 µL, 3.95 mmol). After 25 min, the solvent was removed in vacuo, providing the crude product as a white flaky solid. The material was purified by column chromatography ($SiO_2$, EtOAc:Hex 1:2), which yielded the imine as a colorless mixture of E- and Z-isomers (455 mg, 98%, $R_{fA}$=0.53 $R_{fB}$=0.45 EtOAc:Hex 1:2). $^1H$ NMR ($CDCl_3$, 500 MHz) δ 7.29 (t, J=6.3 Hz, 1H), 7.06 (d, J=8.8 Hz, 2H), 6.61 (d, J=8.8 Hz, 2H), 3.68-3.65 (m, 4H), 3.61-3.58 (m, 4H), 2.55 (t, J=7.7 Hz, 2H), 2.15 (q, J=7.7 Hz, 2H), 1.75 (qui, J=7.7 Hz, 2H); $^{13}C$ NMR ($CDCl_3$, 125 MHz) δ 147.98, 144.45, 131.01, 129.69, 112.22, 53.76, 40.59, 33.23, 29.10, 28.73; HRMS (ESI) m/z for $C_{14}H_{21}Cl_2N_2O$ ($[M+H]^+$) 303.1019, calc. 303.1025.

N-Hydroxy-4-(4-N',N'-bis(2-chloroethyl)amino) phenylbutylamine (65)

Imine 64 (455 mg, 1.50 mmol) was dissolved in absolute EtOH (10 mL), cooled to 0° C., and the reducing agent $BH_3.Et_3N$ (1.1 mL, 7.5 mmol) was added in one aliquot. Concentrated HCl:EtOH 1:1 (1.26 µL) was then dripped in slowly over 5 min. The reaction was quenched with sat. aq. $NaHCO_3$ (5 mL), 5 min after the acid solution was completely added, resulting in a white slurry. The organic solvent was removed under reduced pressure then more $NaHCO_3$ (5 mL) solution was added. The aqueous material was extracted with $CH_2Cl_2$ (4×25 mL) and dried with $Na_2SO_4$. The crude oil was purified by column chromatography ($SiO_2$, $MeOH:CH_2Cl_2$ 2:98 to 5:95) providing the aglycon as a colorless oil (302 mg, 66%, $R_f$=0.36 $MeOH:CH_2Cl_2$ 5:95). $^1H$ NMR ($CDCl_3$, 500 MHz) δ 7.05 (d, J=8.7 Hz, 2H), 6.61 (d, J=8.7 Hz, 2H), 5.23 (s br, 2H), 3.70-3.64 (m, 4H), 3.63-3.57 (m, 4H), 3.40 (s, 2H), 2.58-2.51 (m, 2H), 1.96-1.84 (m, 2H), 1.67-1.55 (m, 2H); $^{13}C$ NMR ($CDCl_3$, 125 MHz) δ 144.60, 131.08, 129.84, 112.47, 53.81, 50.43, 40.88, 34.58, 29.00, 27.16; HRMS (ESI) m/z for $C_{14}H_{23}Cl_2N_2O$ ($[M+H]^+$) 305.1175, calc. 305.1182.

4-(4-N',N'-bis(2-chloroethyl)amino)phenylbutanoic hydrazide (71)

Chlorambucil (1, 319 mg, 1.05 mmol) was dissolved in THF (10 mL), along with N-hydroxysuccinimide (132 mg, 1.15 mmol) and DIC (180 µL, 1.16 mmol). The reaction was warmed to 40° C. and stirred for 5.5 h. Hydrazine (40 μL, 1.27 mmol), pyridine (10 μL), and DMAP (5 mg, 0.04 mmol) were then introduced and the reaction proceeded for another 20 min. The solvent was removed in vacuo yielding a yellowish solid, which was suspended in MeOH:CH$_2$Cl$_2$ 3:97 and purified by column chromatography (SiO$_2$, MeOH:CH$_2$Cl$_2$ 3:97). The hydrazide product was collected as an opaque oil that solidified at −20° C. to a white amorphous solid (285 mg, 85% R$_f$=0.39 MeOH:CH$_2$Cl$_2$ 5:95). $^1$H NMR (CDCl$_3$, 500 MHz) δ 7.31 (s br, 1H), 7.05 (d, J=8.7 Hz, 2H), 6.61 (d, J=8.7 Hz, 2H), 3.90 (s br, 2H), 3.71-3.66 (m, 4H), 3.63-3.58 (m, 4H), 2.54 (t, J=7.6 Hz, 2H), 2.17-2.13 (m, 2H), 1.95-1.89 (m, 2H); $^{13}$C NMR (CDCl$_3$, 125 MHz) δ 20 173.80, 144.46, 130.47, 129.72, 112.26, 53.62, 40.66, 40.88, 34.10, 33.77, 27.19; HRMS (ESI) m/z for C$_{14}$H$_{22}$Cl$_2$N$_3$O ([M+H]$^+$) 318.1140, calc. 318.1134.

General Procedure for Neoglycoside Library Synthesis, Purification, and Characterization.

Aglycons 9, 65, or 71 (typically 0.12-0.16 mmol) were added to 1 dram vials along with stir fleas and dissolved in MeOH such that the aglycon was at a concentration of 90-100 mM. Glacial acetic acid (1.5 eq.) was introduced, reducing sugars (2 eq.) were added, the vials capped, and the vessels placed on a heating block/stir plate to react at 40° C. for 3-48 h. The vial caps were removed and the solvent evaporated by Speedvac apparatus (55° C., 3 h). Crude neoglycosides were suspended in CH$_2$Cl$_2$ (200 μL) using a vortex mixer then loaded onto 2000 mg silica gel solid phase extraction (SPE) columns (Alltech, Deerfield, Ill.) that were prewashed with MeOH/CH$_2$Cl$_2$ 2/98. The SPEs were eluted using a vacuum manifold, collecting fractions with a volume of approximately 2 mL. After the initial two fractions were obtained, eluting any unreacted aglycon or relatively nonpolar material, the following step gradients were used: MeOH/CH$_2$Cl$_2$ 5/95 for tetroses, pentoses, and substituted hexoses; MeOH/CH$_2$Cl$_2$ 10/90 for hexoses; MeOH/CHCl$_3$ 15/85 for disaccharides; MeOH/CHCl$_3$ 20/80 for glycuronosides. For polyprotected saccharides, a gradient of EtOAc/Hex 1/6 to 1/3 was used. Typically, all neoglycoside was eluted by the tenth or eleventh fraction, leaving unreacted sugar on the column. The fractions containing pure product were identified by TLC using UV light (254 nm) and p-anisaldehyde stain, then combined and dried. Library members were characterized by $^1$H and gCOSY NMR as well as either high-resolution ESI or MALDI mass spectrometry (see Tables S2 and S3, Supporting Information). Anomeric ratios were obtained by comparison of anomeric proton integration (see Tables S2 and S3, Supporting Information).

N-Methoxy-4-(4-N',N'-bis(2-chloroethyl)amino)
phenylbutylamino-D-riboside (53)

Aglycon 9 (40 mg, 0.13 mmol) was placed into a 1 dram vial, dissolved in MeOH (1.34 mL), and mixed with glacial acetic acid (10.7 μL). After adding D-ribose (57 mg, 0.38 mmol), the reaction was capped, warmed to 40° C. and allowed to stir for 3 h. Solvent was subsequently removed in vacuo and the resulting crude solid suspended in MeOH:CH$_2$Cl$_2$ 2:98 (250 μL) by vortex mixer. The mixture was purified by SPE (SiO$_2$, MeOH:CH$_2$Cl$_2$ 2:98 to 5:95), providing the white solid neoglycoside as a mixture of anomers (31 mg, 54%, R$_f$=0.34 MeOH:CH$_2$Cl$_2$ 5:95; α:β 1:3). $^1$H NMR (CD$_3$OD, 500 MHz) δ 7.08 (d, J=8.7 Hz, 2H), 6.68 (d, J=8.7 Hz, 2H), 4.56 (d, J=3.4 Hz, 0.25; H, α-H1'), 4.27 (d, J=8.7 Hz, 0.75; H, α-H1'), 4.15 (dd, J=5.4, 3.5 Hz, 0.25; H, α-H2'), 4.12 (s br, 0.75; H, β-H3'), 3.99 (t, J=5.6 Hz, 0.25; H, α-H3'), 3.90-3.86 (m, 0.25, α-H4'), 3.74-3.68 (m, 5H, α-H5$_A$'+β-H5$_A$'), 3.68-3.60 (m, 6.5; H, α-H5$_B$'+β-H2'+β-H4'+β-H5$_B$'), 3.58 (s, 3H), 3.05-2.98 (m, 0.75; H, β-H2A), 2.97-2.92 (m, 0.25; H, α-H2$_A$), 2.86-2.77 (m, 1H, H2$_B$), 2.56 (t, J=7.2 Hz, 2H), 1.71-1.56 (m, 4H); $^{13}$C NMR (CD$_3$OD, 125 MHz) δ 145.86, 132.73, 130.66, 113.61, 100.76 (α-C1'), 91.14 (β-C1'), 84.50 (α-C4'), 73.16 (α-C2'), 72.52 (α-C3'), 72.46 (β-C3'), 68.94 (β-C2'), 68.65 (βC4'), 65.94 (β-C5'), 64.21 (α-C5'), 62.82, 54.76 (α-C2), 54.68, 54.05 (β-C2), 41.82, 35.76, 30.70, 28.12; HRMS (ESI) m/z for C$_{20}$H$_{32}$Cl$_2$N$_2$NaO$_5$ ([M+Na]$^+$) 473.1581, calc. 473.1587.

N-Methoxy-4-(4-N',N'-bis(2-chloroethyl)amino)
phenylbutylamino-L-riboside (54)

Using the same procedure as 53, 9 (52 mg, 0.16 mmol) combined with L-ribose (48 mg, 0.32 mmol), yielded the anomeric mixture as a white solid (40 mg, 54%, R$_f$=0.34 MeOH:CH$_2$Cl$_2$ 5:95; α:β 1:3). $^1$H NMR (CD$_3$OD, 500 MHz) δ 7.05 (d, J=8.6 Hz, 2H), 6.67 (d, J=8.6 Hz, 2H), 4.52 (d, J=3.4 Hz, 0.25; H, α-H1'), 4.25 (d, J=8.7 Hz, 0.75; H, β-H1'), 4.11 (dd, J=5.4, 3.5 Hz, 0.25; H, α-H2'), 4.08 (s br, 0.75; H, β-H3'), 3.95 (t, J=5.5 Hz, 0.25; H, α-H3'), 3.87-3.83 (m, 0.25, α-H4'), 3.71-3.67 (m, 5H, α-H5$_A$'+β-H5$_A$'), 3.65-3.61 (m, 5.75; H, β-H5$_B$'+β-H4'+β-H5$_B$'), 3.60-3.59 (m, 0.75; H, β-H2'), 3.55 (s, 3H), 3.00-2.95 (m, 0.75; H, β-H2$_A$), 2.94-2.89 (m, 0.25; H, α-H2$_A$), 2.81-2.76 (m, 1H, H2$_B$), 2.53 (t, J=7.5 Hz, 2H), 1.66-1.55 (m, 4H); (CD$_3$OD, 125 MHz) δ 145.96, 132.83, 130.69, 113.70, 100.85 (α-C1'), 91.20 (β-C1'), 84.59 (α-C4'), 73.24 (α-C2'), 72.61 (α-C3'), 72.56 (β-C3'), 69.02 (β-C2'), 68.74 (β-C4'), 66.00 (β-C5'), 64.28 (α-C5'), 62.81, 54.78 (α-C2), 54.76, 54.07 (β-C2), 41.86, 35.80, 30.75, 28.15; HRMS (ESI) m/z for C$_{20}$H$_{32}$Cl$_2$N$_2$N$_a$O$_5$ ([M+Na]$^+$) 473.1579, calc. 473.1581.

N-Hydroxy-4-(4-N',N'-bis(2-chloroethyl)amino)
phenylbutylamino-D-fucoside (66)

Using aglycon 65 (63 mg, 0.21 mmol), the mixture of compounds was yielded as a white solid (54 mg, 58%, 22 R$_f$=0.11 MeOH:CH$_2$Cl$_2$ 5:95; α:β:nitrone 2.7:1:1.8). $^1$H NMR (CD$_3$OD, 500 MHz) δ 7.25 (d, J=5.8 Hz, 0.33; H, nitrone-H1'), 7.10-7.07 (m, 2H), 6.70-6.67 (m, 2H), 5.06 (dd, J=5.8, 2.1 Hz, 0.33; H, nitrone-H2'), 4.40 (d, J=4.9 Hz, 0.18; H, α-H1'), 4.30 (dd, J=5.8, 4.9 Hz, 0.18; H, α-H2'), 4.08 (dd, J=6.6, 1.8 Hz, 0.33; H, nitrone-H5'), 3.96 (dd, J=7.5, 5.8 Hz, 0.18; H, α-H3'), 3.89 (dd, J=8.7, 2.1 Hz, 0.33; H, nitrone-H3'), 3.86-3.79 (m, 1.33; H, nitrone-H2+α-H5'+β-H1'), 3.73-3.70 (m, 4.49; H, β-H2'), 3.67-3.63 (m, 4.18; H, α-H4'), 3.61-3.58 (m, 0.98; H, β-H4'αβ-H5'), 3.53-3.50 (m, 0.49; H, β-H3'), 3.48 (dd, J=8.7, 1.8 Hz, 0.33; H, nitrone-H4'), 3.11-3.06 (m, 0.49; H, α-H2$_A$), 3.05-3.01 (m, 0.18; H, α-H2$_A$), 2.79-2.75 (m, 0.49; H, β-H2$_B$), 2.74-2.68 (m, 0.18; H, α-H2$_B$), 2.60-2.54 (m, 2H), 1.91-1.87 (m, 0.66; H, nitrone-H3), 1.68-1.63 (m, 3.34; H), 1.30-1.26 (m, 3H, H6'); $^{13}$C NMR (CD$_3$OD, 125 MHz) δ 145.54 (nitrone-C1'), 144.64, 131.68, 129.45, 112.41, 99.46 (α-C1'), 94.89 (β-C1'), 86.70 (β-C2'), 78.52 (α-C2'), 77.32 (α-C3'), 74.99 (β-C3'), 73.68 (nitrone-C4'), 72.48 (β-C5'), 72.36 (β-C4'), 71.32 (nitrone-C3'), 67.76 (α-C5'), 67.38 (α-C4'), 67.26 (nitrone-C2'), 66.21 (nitrone-C5'), 64.69 (nitrone-C2), 54.87 (β-C2), 53.72 (α-C2), 53.49, 40.64, 34.59, 29.36, 28.16 (α/β-C3), 26.97 (nitrone-C3), 18.95 (α/β-C6'), 18.66 (nitrone-C6'); HRMS (MALDI) m/z for C$_{20}$H$_{32}$Cl$_2$N$_2$NaO$_5$ ([M+Na]$^+$) 473.15911, calc. 473.15805.

N-Hydroxy-4-(4-N',N'-bis(2-chloroethyl)amino)
phenylbutylamino-D-glucurono-6,3-lactonide (67)

Using aglycon 65 (58 mg, 0.19 mmol), the mixture of compounds was yielded as a colorless syrup (49 mg, 56%, $R_f$=0.28 MeOH:CH$_2$Cl$_2$ 5:95; α:β:nitrone 0:1:2.5). $^1$H NMR (CD$_3$OD, 500 MHz) δ 7.25 (d, J=6.3 Hz, 0.71; H, nitrone-H1'), 7.10 (d, J=8.6 Hz, 2H), 6.70 (d, J=8.6 Hz, 2H), 5.11-5.08 (m, 0.71; H, nitrone-H2'), 4.85-4.83 (m, 0.29; H, β-H4'), 4.79 (d, J=4.4 Hz, 0.29; H, β-H3'), 4.57 (d, J=2.3 Hz, 0.29; H, β-H1'), 4.54 (d, J=4.6 Hz, 0.71; H, nitrone-H5'), 4.49 (d, J=2.0 Hz, 0.29; H, β-H5'), 4.47 (d, J=2.8 Hz, 0.71; H, nitrone-H3'), 4.46 (d, J=2.3 Hz, 0.29; H, β-H2'), 4.33 (dd, J=4.6, 2.8 Hz, 0.71; H, nitrone-H4'), 3.91 (q, J=7.0 Hz, 1.42; H, nitrone-H2), 3.74-3.71 (m, 4H), 3.67-3.65 (m, 4H), 2.99-2.96 (m, 0.29; H, β-H2$_A$), 2.69-2.64 (m, 0.29; H, β-H2$_B$), 2.59 (t, J=7.5 Hz, 1.42; H, nitrone-H5), 2.69-2.64 (dd, J=7.2, 6.7 Hz, 0.58; H, β-H5), 1.94-1.87 (m, 1.42; H, nitrone-H3), 1.68-1.62 (m, 2.58; H, β-H3+H4); $^{13}$C NMR (CD$_3$OD, 125 MHz) δ 176.39 (C6'), 144.87, 141.51 (nitrone-C1'), 130.76, 129.48, 112.45, 104.94 (β-C1'), 85.74 (β-C3'), 80.64 (nitrone-C3'), 77.57 (β-C4'), 77.24 (β-C2'), 70.90 (nitrone-C5'), 69.97 (nitrone-C4'), 69.65 (β-C5'), 66.13 (nitrone-C2'), 65.02 (nitrone-C2), 55.41 (β-C2), 53.42, 40.66, 34.55 (β-C5), 33.99 (nitrone-C5), 29.15 (β-C3), 28.17, 26.79 (nitrone-C3); HRMS (MALDI) m/z for C$_{20}$H$_{28}$Cl$_2$N$_2$NaO$_6$ ([M+Na]$^+$) 485.12254, calc. 485.12166.

N-Hydroxy-4-(4-N',N'-bis(2-chloroethyl)amino) phenylbutylamino-D-riboside (68)

Using aglycon 65 (50 mg, 0.16 mmol), the product mixture was yielded as a white solid that was visualized as a single spot by TLC (18 mg, 25%, $R_f$=0.39 MeOH:CH$_2$Cl$_2$ 10:90; α:β:nitrone 1:1:2). $^1$H NMR (CD$_3$OD, 500 MHz) δ 7.17 (d, J=6.3 Hz, 0.5; H, nitrone-H1'), 7.07 (d, J=8.7 Hz, 2H), 6.66 (d, J=8.7 Hz, 2H), 4.99 (dd, J=6.3, 3.5 Hz, 0.5; H, nitrone-H2'), 4.51 (d, J=2.9 Hz, 0.25H, α-H1'), 4.18-4.17 (m, 0.25H, α-H2'), 4.16 (d, J=8.7 Hz, 0.25H, β-H1'), 4.12-4.09 (m, 0.5H, α/β-H4'+β-H2'), 3.89-3.86 (m, 0.5H, α-H3'+α/β-H5$_A$'), 3.86-3.85 (m, 1H, nitrone-H2), 3.84-3.81 (m, 0.25H, α/β-H5$_A$'), 3.78 (dd, J=11.5, 3.5 Hz, 0.5H, nitrone-H3'), 3.74-3.67 (m, 5H, nitrone-H5$_A$'+α/β-H4'+α/β-H5$_B$'), 3.65-3.58 (m, 5H, nitrone-H5$_B$'+α/β-H5$_B$'+β-H3'), 3.55-3.51 (m, 0.5H, nitrone-H4'), 3.08-3.02 (m, 0.25H, α-H2$_A$), 2.98-2.93 (m, 0.25H, α-H2$_B$), 2.74-2.67 (m, 0.5H, β-H2), 2.57 (t, J=7.4 Hz, 2H), 1.92-1.86 (m, 2H), 1.68-1.60 (m, 2H); $^{13}$C NMR (CD$_3$OD, 125 MHz) δ 144.79, 144.63 (nitrone-C1'), 130.80, 129.52, 112.45, 100.86 (α-C1'), 91.12 (β-C1'), 83.43 (α-C3'), 74.19 (nitrone-C3'), 72.98 (α-C2'), 72.31 (nitrone-C4'), 70.79 (β-C2'), 70.71 (α/β-C4'), 68.16 (nitrone-C2'), 67.88 (β-C3'), 67.55 (α/β-C4'), 64.85 (α/β-C5'), 64.82, 63.58 (nitrone-C5'), 62.59 (α/β-C5'), 53.54, 40.57, 34.09, 28.22, 26.78; HRMS (ESI) m/z for C$_{19}$H$_{30}$Cl$_2$N$_2$NaO$_5$ ([M+Na]$^+$) 459.1441, calc. 459.1424.

N-Acetoxy-4-(4-N',N'-bis(2-chloroethyl)amino)phenylbutylamino-D-riboside peracetate (69)

The D-riboside mixture designated 68 (23 mg, 0.053 mmol) was peracetylated by dissolving in THF (5 mL) and adding acetic anhydride (0.5 mL, 5 mmol), DMAP (1 mg, 0.008 mmol), and Et$_3$N (0.5 mL, 4 mmol). After 20 min, the solvent was removed in vacuo and the residue was purified by SPE chromatograpy (SiO$_2$, EtOAc:Hex 2:3). The product was collected as a mixture of anomers of a colorless oil (32 mg, >99%, $R_{fβ}$=0.38 $R_{fα}$=0.32 EtOAc:Hex 2:3; α:β=2:1). $^1$H NMR (CDCl$_3$, 500 MHz) δ 7.06-7.04 (m, 2H), 6.61 (d, J=8.6 Hz, 2H), 5.62 (s, 0.33H, β-H1'), 5.27-5.25 (m, 0.67H, α-H2'), 5.21 (dd, J=6.1, 5.4 Hz, 0.67H, α-H3'), 5.07 (dd, J=9.2, 2.6 Hz, 0.33H, β-H2'), 5.04-5.01 (m, 0.33H, β-H4'), 4.89 (d, J=2.9 Hz, 0.67H, α-H1'), 4.58 (d, J=9.2 Hz, 0.33H, β-H1'), 4.33-4.31 (m, 0.67H, α-H5$_A$'), 4.23-4.20 (m, 0.67H, α-H4'), 4.16 (dd, J=11.7, 5.4 Hz, 0.67H, α-H5$_B$'), 3.97 (dd, J=10.9, 5.4 Hz, 0.33H, β-H5$_A$'), 3.71-3.67 (m, 4.33H, β-H5$_B$'), 3.63-3.60 (m, 4H), 3.20-3.15 (m, 0.33H, β-H2$_A$), 3.11-3.06 (m, 0.67H, α-H2$_A$), 2.99-2.91 (m, 1H, α-H2$_B$+β-H2$_B$), 2.57-2.47 (m, 2H), 2.11 (s, 3H), 2.10 (s, 3H), 2.09 (s, 3H), 2.05 (s, 3H), 1.67-1.46 (m, 4H); $^{13}$C NMR (CDCl$_3$, 125 MHz) δ 170.72, 169.76, 169.51, 169.49, 144.35, 131.49, 129.74, 112.36, 96.56 (α-C1'), 88.60 (β-C1'), 77.85 (α-C4'), 71.99 (α-C2'), 70.58 (α-C3'), 68.93 (β-C3'), 66.47 (β-C4'), 65.72 (β-C2'), 63.55 (α-C5'), 63.21 (β-C5'), 54.06, 53.79, 40.71, 34.55, 29.20, 26.53, 20.93, 20.88, 20.68, 20.65; HRMS (ESI) m/z for C$_{27}$H$_{38}$Cl$_2$N$_2$NaO$_9$ ([M+Na]$^+$) 627.1859, calc. 627.1847.

N-Hydroxy-4-(4-N',N'-bis(2-chloroethyl)amino) phenylbutylamino-D-threoside nitrone (70)

Using aglycon 65 (35 mg, 0.11 mmol), the neoglycoside nitrone was yielded as a colorless syrup (23 mg, 49%, $R_f$=0.11 MeOH:CH$_2$Cl$_2$ 5:95). $^1$H NMR (CD$_3$OD, 500 MHz) δ 7.22 (d, J=5.8 Hz, 1H, H1'), 7.10 (d, J=8.6 Hz, 2H), 6.70 (d, J=8.6 Hz, 2H), 4.84 (dd, J=5.8, 4.2 Hz, 1H, H2'), 3.87-3.84 (m, 3H, H3'+H4'), 3.75-3.72 (m, 4H), 3.68-3.61 (m, 6H), 2.59 (t, J=7.4 Hz, 2H), 1.93-1.87 (m, 2H), 1.69-1.63 (m, 2H); $^{13}$C NMR (CD$_3$OD, 125 MHz) δ 146.11, 146.01 (C1'), 132.10, 130.72, 113.71, 73.93 (C3'), 68.77 (C2'), 65.95 (C4'), 64.09, 54.70, 41.85, 35.30, 29.41, 27.93; HRMS (MALDI) m/z for C$_{18}$H$_{28}$Cl$_2$N$_2$NaO$_4$ ([M+Na]$^+$) 429.13188, calc. 429.13183.

4-(4-N',N'-bis(2-chloroethyl)amino)phenylbutylhydrazido-β-D-fucoside (72)

Using aglycon 71 (47 mg, 0.15 mmol), the product was yielded as a colorless syrup (46 mg, 67%, $R_f$=0.28 MeOH:CH$_2$Cl$_2$ 10:90). $^1$H NMR (CD$_3$OD, 500 MHz) δ 7.09 (d, J=8.6 Hz, 2H), 6.70 (d, J=8.6 Hz, 2H), 3.86 (d, J=8.7 Hz, 1H, H1'), 3.74-3.72 (m, 4H), 3.68-3.65 (m, 4H), 3.64-3.62 (m, 2H, H3'+H5'), 3.54 (dd, J=9.5, 3.2 Hz, 1H, H4'), 3.48 (d, J=8.7 Hz, 1H, H2'), 2.56 (t, J=7.5 Hz, 2H), 2.21 (t, J=7.5 Hz, 2H), 1.90 (qui, J=7.5 Hz, 2H), 1.28 (d, J=6.4 Hz 3H); $^{13}$C NMR (CD$_3$OD, 125 MHz) δ 174.72, 144.86, 130.58, 129.53, 112.44, 91.30 (C1'), 74.29 (C4'), 72.12 (C3'), 72.03 (C5'), 68.38 (C2'), 53.45, 40.61, 34.02, 33.28, 27.65, 24.17, 15.93 (C6'); HRMS (MALDI) m/z for C$_{20}$H$_{31}$Cl$_2$N$_3$NaO$_5$ ([M+Na]$^+$) 486.15233, calc. 486.15330.

4-(4-N',N'-bis(2-chloroethyl)amino)phenylbutylhydrazido-D-glucurono-6,3-lactonide (73)

Using aglycon 71 (61 mg, 0.19 mmol), the mixture of compounds was yielded as a colorless syrup (42 mg, 44%, $R_{fA}$=0.55 $R_{fB}$=0.47 MeOH:CH$_2$Cl$_2$ 10:90; α:β:imine=0:1:1). $^1$H NMR (CD$_3$OD, 500 MHz) δ 7.57 (d, J=4.3 Hz, 0.35H, imine A-H1'), 7.41 (d, J=4.1 Hz, 0.15H, imine B-H1'), 7.09 (d, J=8.6 Hz, 2H), 6.70 (d, J=8.6 Hz, 2H), 4.91 (dd, J=6.4, 4.7 Hz, 0.5H, β-H4'), 4.85-4.79 (m, 0.5H, β-H3'), 4.78 (d, J=1.4 Hz, 0.5H, β-H1'), 4.68 (dd, J=7.6, 4.3 Hz, 0.35H, imine A-H2'), 4.63 (dd, J=7.8, 4.1 Hz, 0.15H, imine B-H2'), 4.57-4.54 (m, 1H, imine-H4'/H5'+β-H2'), 4.53-4.50 (m, 1.35H, imine A-H3'+imine-H4'/H5'+β-H5'), 4.46-4.44 (m, 0.15H, imine B-H3'), 3.75-3.71 (m, 4H), 3.68-3.65 (m, 4H), 2.71-2.54 (m, 2H), 2.27 (t, J=7.5 Hz, 1H), 2.20-2.15 (m, 1H), 1.96-1.87 (m, 2H); $^{13}$C NMR (CD$_3$OD, 125 MHz) δ 176.71 (imine-C6'), 176.08 (β-C6'), 171.83, 148.17 (imine A-C1'), 144.93, 144.85 (imine B-C1'), 130.37, 129.50, 112.43, 99.79 (β-C1'), 84.14 (β-C3'), 81.62 (imine BC3'), 81.53 (imine A-C3'), 77.83 (β-C4'), 70.96 (imine B-C4'/C5'), 70.88

(β-C2'), 70.11 (imine AC4'/C5'), 69.97 (imine B-C4'/C5'), 69.84 (imine A-C4'/C5'), 69.49 (β-C5'), 69.20 (imine A-C2'), 69.59 (imine B-C2'), 53.40, 40.62, 33.99, 33.58 (β-C2), 33.47 (imine-C2), 27.36; HRMS (MALDI) m/z for $C_{20}H_{27}Cl_2N_3NaO_6$ ([M+Na]$^+$) 498.11631, calc. 498.11691.

4-(4-N',N'-bis(2-chloroethyl)amino)phenylbutylhydrazido-D-threoside imine (74)

Using aglycon 71 (36 mg, 0.11 mmol), the neoglycoside imine was yielded as a colorless syrup (41 mg, 85%, $R_f$=0.19 MeOH:CH$_2$Cl$_2$ 10:90). $^1$H NMR (CD$_3$OD, 500 MHz) δ 7.53 (d, J=4.9 Hz, 0.6H, imine AH1'), 7.37 (d, J=5.5 Hz, 0.4H, imine B-H1'), 7.08 (d, J=8.6 Hz, 2H), 6.70 (d, J=8.6 Hz, 2H), 4.32 (t, J=4.4 Hz, 0.6H, imine A-H2'), 4.25 (m, 0.4H, imine B-H2'), 3.78-3.70 (m, 5H, imine-H3'), 3.69-3.60 (m, 6H, imine-H4'), 2.65 (t, J=7.5 Hz, 0.8H, imine B-H2), 2.58 (t, J=7.5 Hz, 1.2H, imine A-H2), 2.26 (t, J=7.5 Hz, 1.2H, imine A-H4), 1.98-1.90 (m, 2.8H, imine-H3+imine B-H3); $^{13}$C NMR (CD$_3$OD, 125 MHz) δ 171.67, 151.04 (imine A-C1'), 147.62 (imine B-C1'), 144.92, 130.40, 129.49, 112.44, 73.65 (imine B-C3'), 73.46 (imine A-C3'), 71.49 (imine B-C2'), 71.40 (imine A-C2'), 62.60 (imine-C4'), 53.42, 40.59, 34.19 (imine B-C2), 34.00 (imine A-C2), 33.56 (imine A-C4), 31.76 (imine B-C4), 27.41 (imine A-C3), 26.82 (imine B-C3); HRMS (MALDI) m/z for $C_{18}H_{27}Cl_2N_3NaO_4$ ([M+Na]$^+$) 442.12721, calc. 442.12708.

4-(4-N',N'-bis(2-chloroethyl)amino)phenylbutylhydrazido-D-xyloside (75)

Using aglycon 71 (60 mg, 0.19 mmol), the mixture of compounds was yielded as a colorless syrup (40 mg, 45%, $R_{fA}$=0.36 $R_{fB}$=0.29 MeOH:CH$_2$Cl$_2$ 10:90; α:β:imine=0:2.3:1). $^1$H NMR (CD$_3$OD, 500 MHz) δ 7.54 (d, J=5.0 Hz, 0.15H, imine A-H1'), 7.38 (d, J=5.5 Hz, 0.15H, imine B-H1'), 7.09 (d, J=8.6 Hz, 2H), 6.70 (d, J=8.6 Hz, 2H), 4.45 (d, J=3.8 Hz, 0.15H, imine A-H2'), 4.40 (t, J=4.9 Hz, 0.15H, imine B-H2'), 3.89 (dd, J=11.3, 5.4 Hz, 0.7H, β-H5$_A$'), 3.85 (d, J=8.7 Hz, 0.7H, β-H1'), 3.75-3.72 (m, 4.3H, imine B-H3'+imine A/B-H4'), 3.68-3.65 (m, 4.75H, imine A/B-H4'+imine-H5'), 3.59 (dd, J=7.8, 4.0 Hz, 0.15H, imine A-H3'), 3.52-3.45 (m, 0.7H, β-H4'), 3.39-3.36 (m, 0.7H, β-H3'), 3.23-3.16 (m, 1.4H, β-H2'+β-H5$_B$'), 2.56 (t, J=7.5 Hz, 2H), 2.27-2.24 (m, 0.6H, imine-H2), 2.21-2.17 (m, 1.4H, β-H2), 1.96-1.87 (m, 2H); $^{13}$C NMR (CD$_3$OD, 125 MHz) δ 174.67, 144.87, 130.53, 129.49, 112.43, 91.78 (β-C1'), 87.51 (imine A-C2'), 77.17 (β-C3'), 72.44 (imine A/B-C4'), 72.43 (imine B-C3'), 71.57 (imine A/B-C4'), 72.00 (imine B-C2'), 71.34 (β-C2'), 70.92 (imine A-C3'), 70.05 (β-C4'), 67.28 (β-C5'), 62.95 (imine-C5'), 53.43, 40.60, 33.99, 33.22, 27.67; HRMS (MALDI) m/z for $C_{19}H_{29}Cl_2N_3NaO_5$ ([M+Na]$^+$) 472.13712, calc. 472.13765.

Cell Proliferation Assays.

Testing was performed by the Keck-UWCCC Small Molecule Screening Facility (Madison, Wis.). General carcinoma cell line maintenance, compound handling and assay protocols have been previously reported. Briefly, cells were plated in 50 μL volumes at a density of 500 cells per well in 384-well clear bottom tissue culture plates. Serial dilutions of 30 mM DMSO compound stock solutions were accomplished in 96-well plates using a BioTek Precision XS liquid handler (Winooski, Vt.) to a concentration 100× greater than that of the most dilute assay. Final dilutions were performed in a 384-well plate in quadruplicate using a Beckman-Coulter Biomek FX liquid handler with a 384 channel pipetting head (Fullerton, Calif.) and were stored at −20° C. when not in use. Compounds were then added to the culture plates by the Biomek FX handler and were incubated at 37° C. for 7 d in an atmosphere containing 5% CO$_2$. The calcein AM reagent (acetoxymethyl ester; 10 μM) and ETHD-1 (100 μM; 30 μL total) were added, the treated cells incubated for 30 m at 37° C., and plates read for fluorescent emission using a Tecan Safire2 microplate reader (Duram, N.C.) at the appropriate wavelengths. Cell titer-glo reagent (15 μL; Promega Corp., Madison, Wis.) was added and the plates incubated for 10 m at room temperature with gentle agitation to lyse the cells. Each plate was re-examined for luminescence to verify inhibition. GI$_{50}$ values for cytotoxicity were determined using XLfit 4.2 as previously reported. For compound 60, the most active neoglycoside, the NCI60 human tumor cancer cell line screen was performed by the Developmental Therapeutics Program of the National Cancer Institute (Rockville, Md.) as previously described.

CONCLUSION

In summary, this study revealed a facile four step process, which could be conducted on gram scale in less than two hours of reaction time and required only a single chromatographic separation, to modify the drug chlorambucil (1) for chemoselective glycosylation. While prior syntheses of 1-glycoconjugates focused upon the use of typical metabolic sugars designed to enhance sugar-mediated uptake and led to modest overall improvements compared to 1, the current study revealed anticancer potency optimization was best accomplished via conjugation with novel non-metabolic sugars—culminating in the discovery of D-threoside 60 as the most active chlorambucil glycoside reported to date. Table 6 shows the results for the NCI 60 Human Tumor Cell Line Anticancer Screen for D-Threoside-60.

The discovery of 60 opens the door to a series of new questions relating to the precise mechanism(s) of improvement—including among the many possibilities: i) modulation of uptake (via novel targeting of known transporters and/or even raising the possibility of new sugar transport/receptor mediated-processes); ii) intracellular stabilization of the alkylating reagent (basically extending the intracellular T1/2); iii) enhancing the productive agent-DNA interactions (e.g., DNA affinity and/or specificity); and/or even iv) alternative targeting of the active species (e.g., RNA, proteins, and/or membrane targets). While the specific mechanism(s) remain to be elucidated, it is important to note that precedent does exists for 1 glucosylation to alter the mechanism of cellular uptake.

In addition to the lead discovery aspect of this project, it is also important to note that the corresponding in-depth product distribution analysis among N-alkoxyamino-, N-acyl hydrazine- and Nhydroxyamino-based neoglycosylation reactions revealed sugar-dependent partitioning among open and closed-ring neoglycosides in the latter two cases. Thus, this cumulative study also sheds new light (and a potential note of caution) on an under-appreciated chemical variability of glycoconjugates generated via the N-acyl hydrazine- and N-hydroxyamine-based chemoselective glycosylation methods more commonly applied in glycobiology.

TABLE 6

NCI 60 Human Tumor Cell Line Anticancer Screen for D-Threoside-60

| panel/cell line | Inhibition at 10 μM[a] | GI$_{50}$ (μM)[b] |
|---|---|---|
| Leukemia | | |
| CCRF-CEM | 21.19 | 2.36 |
| HL-60 (TB) | 68.31 | 1.88 |
| K-562 | 88.55 | — |
| MOLT-4 | 64.41 | 1.22 |
| RPMI-8226 | 15.94 | — |
| SR | 48.67 | 0.386 |
| Non-small cell lung | | |
| A549/ATCC | 69.72 | 12.2 |
| EKVX | 91.24 | 37.9 |
| HOP-62 | 73.20 | 8.28 |
| HOP-92 | 58.81 | 4.03 |
| NCI-H226 | 84.25 | 0.925 |
| NCI-H23 | 54.44 | 7.15 |
| NCI-H322M | 99.02 | >100 |
| NCI-H460 | 35.80 | 3.76 |
| NCI-H522 | 52.38 | 10.0 |
| Colon | | |
| COLO 205 | 93.34 | 12.7 |
| HCC-2998 | 73.29 | — |
| HCT-116 | 69.37 | 14.5 |
| HCT-15 | 77.10 | 19.7 |
| HT29 | 70.71 | 26.6 |
| KM12 | 97.57 | 30.0 |
| SW-620 | 68.08 | 12.4 |
| CNS | | |
| SF-268 | 67.83 | 5.75 |
| SF-295 | 56.59 | 6.47 |
| SF-539 | 51.79 | 8.80 |
| SNB-19 | 65.81 | 33.4 |
| SNB-75 | 66.74 | 19.5 |
| U251 | 59.94 | 13.1 |
| Prostate | | |
| PC-3 | 72.52 | 11.7 |
| DU-145 | 56.78 | 4.84 |
| Melanoma | | |
| LOX IMVI | 54.82 | 8.61 |
| MALME-3M | 69.73 | 20.2 |
| M14 | 67.23 | 9.25 |
| MDA-MB-435 | 83.03 | 21.1 |
| SK-MEL-2 | 100.16 | 20.2 |
| SK-MEL-28 | 116.87 | 36.5 |
| SK-MEL-5 | 79.00 | 17.7 |
| UACC-62 | 52.06 | 1.69 |
| Ovary | | |
| IGROV1 | — | 1.21 |
| OVCAR-3 | 85.34 | 15.3 |
| OVCAR-4 | 77.16 | 29.2 |
| OVCAR-5 | 111.11 | — |
| OVCAR-8 | 68.13 | 9.13 |
| NCI/ADR-RES | 61.54 | 4.61 |
| SKOV3 | 72.76 | 17.9 |
| Renal | | |
| 786-0 | 67.90 | 6.16 |
| A498 | 114.47 | 21.8 |
| ACHN | 14.27 | 4.34 |
| CAKI-1 | 13.59 | 11.5 |
| SN12C | 54.23 | 7.06 |
| TK-10 | 97.20 | 31.7 |
| UO-31 | 54.43 | 0.856 |
| Breast | | |
| MCF7 | 32.40 | 4.51 |
| MDA-MB-231 | 87.54 | 1.39 |
| HS 578T | 139.25 | 24.7 |
| BT-549 | 38.53 | 13.4 |
| T-47D | 48.01 | 6.37 |
| MDA-MB-468 | 43.87 | 7.25 |

[a]Percent growth inhibition at a single neoglycoside concentration (10 μM).
[b]Concentration required to reduce the growth of treated cells to half that of untreated cells.

REFERENCES (1) Křen, V.; Řezanka, T. Sweet Antibiotics. The role of glycosidic residues in antibiotic and antitumor activity and their randomization. *FEMS Microbiol. Rev.* 2008, 32, 858-889.

(2) Thorson, J. S.; Hosted, T. J., Jr.; Jiang, J.; Biggins, J. B.; Ahlert, J. Nature's carbohydrate chemists: the enzymatic glycosylation of bioactive bacterial metabolites. *Curr. Org. Chem.* 2001, 5, 139-167.

(3) Weymouth-Wilson, A. C. The role of carbohydrates in biologically active natural products. *Nat. Prod. Rep.* 1997, 14, 99-110.

(4) Salas, J. A.; Méndez, C. Engineering the glycosylation of natural products in Actinomycetes. *Trends Microbiol.* 2007, 15, 119-232.

(5) Thibodeaux, C. J.; Melançon, C. E.; Liu, H.-W. Unusual sugar biosynthesis and natural product glycodiversification. *Nature* 2007, 446, 1008-1016.

(6) Blanchard, S.; Thorson, J. S. Enzymatic tools for engineering natural product glycosylation. *Curr. Opin. Chem. Biol.* 2006, 10, 263-271;

(7) Griffith, B. R.; Langenhan, J. M.; Thorson, J. S. 'Sweetening' natural products via glycorandomization. *Curr. Opin. Biotechnol.* 2005, 16, 622-630.

(8) Langenhan, J. M.; Griffith, B. R.; Thorson, J. S, Neoglycorandomization and chemoenzymatic glycorandomization: two complementary tools for natural product diversification. *J. Nat. Prod.* 2005, 68, 1696-1711.

(9) Peri, F.; Dumy, P.; Mutter, M. Chemo- and stereoselective glycosylation of hydroxylamino derivatives: a versatile approach to glycoconjugates. *Tetrahedron* 1998, 54, 12269-12278.

(10) Peri, F.; Deutman, A.; La Ferla, B.; Nicotra F. Solution and solid-phase chemoselective synthesis of (1-6)-amino (methoxy) di- and trisaccharide analogs. *Chem. Commun.* 2002, 1504-1505.

(11) Carrasco, M. R.; Nguyen, M. J.; Burnell, D. R.; MacLaren, M. D.; Hengel, S. M. Synthesis of neoglycopeptides by chemoselective reaction of carbohydrates with peptides containing a novel N'-methyl-aminooxy amino acid. *Tetrahedron Lett.* 2002, 43, 5727-5729.

(12) Carrasco, M. R.; Brown, R. T. A versatile set of aminooxy amino acids for the synthesis of neoglycopeptides. *J. Org. Chem.* 2003, 68, 8853-8858.

(13) Carrasco, M. R.; Brown, R. T.; Serafimova, I. M.; Silva, O. Synthesis of N-Fmoc-O-(N'Boc-N'-methyl)-aminohomoserine, an amino acid for the facile preparation of neoglycopeptides. *J. Org. Chem.* 2003, 68, 195-197.

(14) Peri, F. Extending chemoselective ligation to sugar chemistry: convergent assembly of bioactive neoglycoconjugates. *Mini-Rev. Med. Chem.* 2003, 3, 651-658.

(15) Peri, F.; Jiménez-Barbero, J.; García-Aparicio, V.; Tvaroška, I.; Nicotra, F: Synthesis and conformational analysis of novel N(OCH₃)-linked disaccharide analogues. *Chem. Eur. J.* 2004, 10, 1433-1444.

(16) Peri, F.; Nicotra, F. Chemoselective ligation in glycochemistry. *Chem. Commun.* 2004, 623-627.

(17) Langenhan, J. M.; Thorson, J. S. Recent carbohydrate-based chemoselective ligation applications. *Curr. Org. Syn.* 2005, 2, 59-81.

(18) Carrasco, M. R.; Brown, R. T.; Doan, V. H.; Kandel, S. M.; Lee, F. C. 2-(N-Fmoc)-3-(N-Boc-Nmethoxy)-diaminopropanoic acid, an amino acid for the synthesis of mimics of O-linked glycopeptides. *Biopolymers* 2006, 84, 414-420.

(19) Nicotra, F.; Cipolla, L.; Peri, F.; La Ferla, B.; Redaelli, C. Chemoselective neoglycosylation. *Adv. Carbohydr. Chem. Biochem.* 2007, 61, 353-398.

(20) Langenhan, J. M.; Peters, N. R.; Guzei, I. A.; Hoffman, M. A.; Thorson, J. S. Enhancing the anticancer properties of cardiac glycosides by neoglycorandomization. *Proc. Nat. Acad. Sci. U.S.A.* 2005, 102, 12305-12310.

(21) Ahmed, A.; Peters, N. R.; Fitzgerald, M. K.; Watson, J. A., Jr.; Hoffmann, F. M.; Thorson, J. S. Colchicine glycorandomization influences cytotoxicity and mechanism of action. *J. Am. Chem. Soc.* 2006, 128, 14224-14225.

(22) Griffith, B. R.; Krepel, C.; Fu. X.; Blanchard, S.; Ahmed, A.; Edmiston, C. E.; Thorson, J. S. Model for antibiotic optimization via neoglycosylation: synthesis of lipo-neoglycopeptides active against VRE. *J. Am. Chem. Soc.* 2007, 129, 8150-8155.

(23) Langenhan, J. M.; Engle, J. M.; Slevin, L. K.; Fay, L. R.; Lucker, R. W.; Smith, K. R.; Endo, M. M. Modifying the glycosidic linkage in digitoxin analogs provides selective cytotoxins. *Bioorg. Med. Chem. Lett.* 2008, 18, 670-673.

(24) Goff, R. D.; Thorson, J. S. Enhancing the divergent activities of betulinic acid via neoglycosylation. *Org. Lett.* 2009, 11, 461-464.

(25) Everett, J. L.; Roberts, J. J.; Ross, W. C. J. Aryl-2-haloalkylamines. XII. Some carboxylic derivatives of N,N-bis(2-chloroethyl)aniline. *J. Chem. Soc.* 1953, 2386-2392.

(26) Jaksic, B.; Brugiatelli, M.; Krc, I.; Losonczi, H.; Holowiecki, J.; Planinc-Peraica, A.; Kusec, R.; Morabito, F.; Iacopino, P.; Lutz, D. High dose chlorambucil versus Binet's modified cyclophosphamide, doxorubicin, vincristine, and prednisone regimen in the treatment of patients with advanced B-cell chronic lymphocytic leukemia. Results of an international multicenter randomized trial. *Cancer* 1997, 79, 2107-2114.

(27) Robak, T.; Kasznicki, M. Alkylating agents and nucleoside analogues in the treatment of B cell chronic lymphocytic leukemia. *Leukemia* 2002, 16, 1015-1027.

(28) Nicolle, A.; Proctor, S. J.; Summerfield, G. P. High dose chlorambucil in the treatment of lymphoid malignancies. *Leuk. Lymphoma* 2004, 45, 271-275.

(29) Robak, T. Recent progress in the management of chronic lymphocytic leukemia. *Cancer Treat. Rev.* 2007, 33, 710-728.

(30) Robak, T.; Jamroziak, K.; Robak, P. Current and emerging treatments for chronic lymphocytic leukemia. *Drugs* 2009, 69, 2415-2449.

(31) Kahl B. S.; Bartlett, N. L.; Leonard, J. P.; Chen, L.; Ganjoo, K.; Williams, M. E.; Czuczman, M. S.; Robinson, K. S.; Joyce, R.; van der Jagt, R. H.; Cheson, B. D. Bendamustine is effective therapy in patients with rituximab-refractory, indolent B-cell non-hodgkin lymphoma: results from a multicenter study. *Cancer* 2010, 116, 106-114.

(32) Millard, J. T.; Raucher, S.; Hopkins, P. B. Mechlorethamine cross-links deoxyguanosine residues at 5'-GNC sequences in duplex DNA fragments. *J. Am. Chem. Soc.* 1990, 112, 2459-2460.

(33) Denny, W. A. DNA minor groove alkylating agents. *Curr. Med. Chem.* 2001, 8, 533-544.

(34) Bank, B. B.; Kanganis, D.; Liebes, L. F.; Silber, R. Chlorambucil pharmacokinetics and DNA binding in chronic lymphocytic leukemia lymphocytes. *Cancer Res.* 1989, 49, 554-559.

(35) Dorr, R. T.; Fritz, W. L. *Cancer Chemotherapy Handbook*; Elsevier Science: New York, 1980.

(36) Sanderson, B. J. S.; Johnson, K. J.; Henner, W. D. Induction of mutant lymphocytes in cyclophosphamide- and chlorambucil-treated patients. *Mutagenesis* 2001, 16, 197-202.

(37) Palayoor, S. T.; Mitchell, J. B.; Cerna, D.; Degraff, W.; John-Aryankalayil, M.; Coleman, C. N. PX-478, an inhibitor of hypoxia-inducible factor-1α, enhances radiosensitivity of prostate carcinoma cells. *Int. J. Cancer* 2008, 123, 2430-2437

(38) Veyhl, M.; Wagner, K.; Volk, C.; Gorboulev, V.; Baumgarten, K.; Weber, W.-M.; Schaper, M.; Bertam, B.; Wiessler, M.; Koepsell, H. Transport of the new chemotherapeutic agent β-Dglucosylisophosphoramidemustard (D-19575) into tumor cells is mediated by the Na⁺-D-glucose cotransporter SAAT1. *Proc. Natl. Acad. Sci. U.S.A.* 1998, 95, 2914-2919.

(39) (a) Schein, P. S.; Green, D.; Hammer, C. F.; McPherson, E.; Talebian, A. 6-bis-(2-chloroethyl)amino-6-deoxy-D-galactopyranose hydrochloride: synthesis, chemical characterization, murine P388 antitumor activity, and bone marrow toxicity. *J. Pharm. Sci.* 1989, 78, 918-921.

(40) Atassi, G.; Dumont, P.; Gosse, C.; Fournier, J. P.; Gouyette, A.; Roger, P. Characterization of the antitumor activity against solid tumors of a new nitrosoureido sugar: Cy 233. *Cancer Chemother. Pharmacol.* 1989, 25, 205-209.

(41) Sosnovsky, G.; Rao, N. U. M. In the search for new anticancer drugs. XXIII: exploration of a predictive design for anticancer drugs of carbohydrates containing N-nitrosochloroethylamino, Nnitrosomethyl, and N-nitrosoaminoxyl components. *J. Pharm. Sci.* 1991, 80, 693-699.

(42) Halmos, T.; Santarromana, M.; Antonakis, K.; Scherman, D. Synthesis of glucose-chlorambucil derivatives and their recognition by the human GLUT1 glucose transporter. *Eur. J. Pharmacol.* 1996, 318, 477-484.

(43) Iglesias-Guerra, F.; Candela, J. I.; Bautista, J.; Alcudia, F.; Vega-Perez, J. M. Potential anticancer drugs, Part 2. Alkylating agents from sugars. Alkyl hexopyranoside derivatives as carrier systems for chlorambucil. *Carbohydr. Res.* 1999, 316, 71-84.

(44) Vega-Perez, J. M.; Candela, J. I.; Blanco, E.; Iglesias-Guerra, F. Potential anticancer drugs. Part 3. Alkylating agents from sugars. Stereoselective synthesis of 2,3-diaminoglucoses from 2-nitroalkenes, as intermediates in the synthesis of carriers of chlorambucil. *Tetrahedron* 1999, 55, 9641-9650.

(45) Iglesias-Guerra, F.; Candela, J. I.; Blanco, E.; Alcudia, F.; Vega-Perez, J. M. Alkylating agents from sugars: synthesis of chlorambucil derivatives carried by chiral glycosyl glycerols derived from Dglucosamine. *Chirality* 2002, 14, 199-203.

(46) Reux, B.; Weber, V.; Galmier, M.-J.; Borel, M.; Madesclaire, M.; Madelmont, J.-C.; Debiton, E.; Coudert, P. Syn-

(47) Thorens, B.; Mueckler, M. Glucose transporters in the 21st century. *Am. J. Physiol. Endocrinol. Metab.* 2010, 298, 141-145.

(48) Zhao, F.-Q.; Keating, A. F. Functional properties and genomics of glucose transporters. *Curr. Genomics* 2007, 8, 113-128.

(49) Macheda, M. L.; Rogers, S.; Best, J. D. Molecular and cellular regulation of glucose transporter (GLUT) proteins in cancer. *J. Cell. Physiol.* 2005, 202, 654-662.

(50) Joost, H.-G.; Thorens, B. The extended GLUT-family of sugar/polyol transport facilitators: nomenclature, sequence characteristics, and potential function of its novel members (review). *Mol. Membrane. Biol.* 2001, 18, 247-256.

(51) Merino, P.; Franco, S.; Merchan, F. L.; Tejero, T. A facile synthesis of glycosyl hydroxylamines. *Synth. Commun.* 1997, 27, 3529-3537.

(52) Dondoni, A.; Giovannini, P. P.; Perrone, D. New synthesis of pyrrolidine homoazasugars via aminohomologation of furanoses and their use for the stereoselective synthesis of aza-C-disaccharides. *J. Org. Chem.* 2002, 67, 7203-7214.

(53) Cicchi, S.; Marradi, M.; Corsi, M.; Faggi, C.; Goti, A. Chiral nitrones from lactols, 1. Preparation of N-Glycosyl-hydroxylamines and their oxidation to nitrones for the enantioselective synthesis of isoxazolidines. *Eur. J. Org. Chem.* 2003, 4152-4160.

(54) Bendiak, B. Preparation, conformation, and mild hydrolysis of 1-glycosyl-2-acetylhydrazines of the hexoses, pentoses, 2-acetamido-2-deoxyhexoses, and fucose. *Carbohydr. Res.* 1997, 304, 85-90.

(55) Leteux, C.; Childs, R. A.; Chai, W.; Stoll, M. S.; Kogelberg, H.; Feizi, T. Biotinyl-L-3-(2-naphthyl)-alanine hydrazide derivatives of N-glycans: versatile solid-phase probes for carbohydraterecognition studies. *Glycobiology* 1998, 8, 227-236.

(56) Auge, J.; Lubin-Germain, N. Glycosylhydrazides, a new class of sugar surfactants. Preparation and amphiphilic properties of 1-glycosyl-2-acylhydrazines. *J. Carbohydr. Chem.* 2000, 19, 379-392.

(57) Peluso, S.; Ufret, M. L.; O'Reilly, M. K.; Imperiali, B. Neoglycopeptides as inhibitors of oligosaccharyl transferase: insight into negotiating product inhibition. *Chem. Biol.* 2002, 9, 1323-1328.

(58) Guillaumie, F.; Thomas, O. R. T.; Jensen, K. J. Immobilization of pectin fragments on solid supports: novel coupling by thiazolidine formation. *Bioconjugate Chem.* 2002, 13, 285-294:

(59) Flinn, N. S.; Quibell, M.; Monk, T. P.; Ramjee, M. K.; Urch, C. J. A single-step method for the production of sugar hydrazides: intermediates for the chemoselective preparation of glycoconjugates. *Bioconjugate Chem.* 2005, 16, 722-728.

(60) Grigor'ev, I. A. Nitrones: Novel Strategies in Synthesis. In *Nitrile Oxides, Nitrones, and Nitronates in Organic Synthesis,* 2nd Edition; Feuer, H, Ed.; John Wiley & Sons, Inc.: Hoboken, N.J., 2008; pp 129-434.

(61) Developmental Therapeutics Program NCI/NIH Home Page. http://dtp.nci.nih.gov/branches/btb/ivclsp.html (accessed May 4, 2010).

(62) Shoemaker, R. H. The NCI60 human tumour cell line anticancer drug screen. *Nature Rev. Cancer* 2006, 6, 813-823.

In this application, the present invention has been described in what is perceived to be the most practical and preferred embodiments and examples, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims. All references cited herein are incorporated by reference for all purposes.

What is claimed is:

1. A chlorambucil neoglycoside having the general formula:

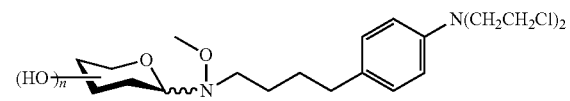

wherein

represents a reducing sugar moiety selected from the group consisting of an L-sugar, a D-sugar, a deoxy-sugar, a dideoxy-sugar, a glucose epimer, a sugar substituted with benzyl, acetyl, halogen, amino, methyl or alloc, a uronic acid, and an oligosaccharide.

2. The chlorambucil neoglycoside of claim 1, wherein the reducing sugar moiety is selected from the group consisting of D-allose (10), L-allose (11), D-altrose (12), L-altrose (13), D-arabinose (14), L-arabinose (15), 2,3,5-O-tribenzyl-D-arabinose (16), D-cellobiose (17), D-digitoxose (18), D-erythrose (19), D-fucose (20), L-fucose (21), 2,3,4-O-tribenzyl-L-fucose (22), D-galactose (23), L-galactose (24), 2-deoxy-D-galactose (25), D-galacturonose (26), N-acetyl-D-galactosamine (27), D-glucose (28), L-glucose (29), 2-deoxy-D-glucose (30), 2-deoxy-2-fluoro-D-glucose (31), 3-deoxy-3-fluoro-D-glucose (32), 3-O-methyl-D-glucose (33), 6-deoxy-6-amino-D-glucose (34), 6-deoxy-6-amino-6-N-alloc-D-glucose (35), 6-chloro-6-deoxy-D-glucose (36), 6-deoxy-D-glucose (37), D-glucuronose (38), D-glucuronolactone (39), L-gulose (40), D-lyxose (41), L-lyxose (42), D-mannose (43), L-mannose (44), N-acetyl-D mannosamine (45), D-Galacto-(1,4)-β-D-Mannose (46), D-melibiose (47), D-MurNAc (48), L-noviose (49), D-olivose (50), L-rhamnose (51), 2,3,4-tri-O-acetyl-L-rhamnose (52), D-ribose (53), L-ribose (54), 2-deoxy-D-ribose (55), 2-deoxy-L-ribose (56), 2,3,5-tri-O-benzyl-D-ribose (57), D-talose (58), L-talose (59), D-threose (60), L-threose (61), D-xylose (62), and L-xylose (63).

3. The chlorambucil neoglycoside of claim 2, wherein the reducing sugar moiety is D-arabinose (14), L-arabinose (15), D-glucuronolactone (39), D-threose (60), L-threose (61), D-xylose (62), or L-xylose (63).

4. The chlorambucil neoglycoside of claim 3, wherein the reducing sugar is D-glucuronolactone (39) or D-threose (60).

5. The chlorambucil neoglycoside of claim 4, wherein the reducing sugar is D-threose (60).

6. A chlorambucil neoglycoside having the general formula:

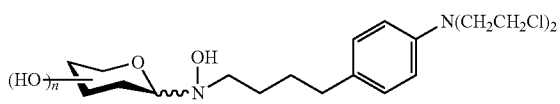

wherein

represents a reducing sugar moiety selected from the group consisting of an L-sugar, a D-sugar, a deoxy-sugar, a dideoxy-sugar, a glucose epimer, a sugar substituted with benzyl, acetyl, halogen, amino, methyl or alloc, a uronic acid, and an oligosaccharide.

7. The chlorambucil neoglycoside of claim 6, wherein the reducing sugar moiety is D-fucose (66), D-glucuronolactone (67), or D-ribose (68).

8. A chlorambucil neoglycoside produced when an aglycon chlorambucil analog selected from the group consisting of

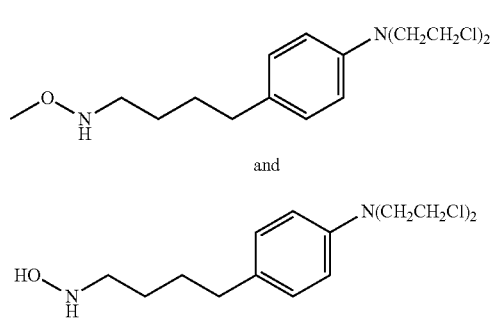

is contacted with a reducing sugar selected from the group consisting of an L-sugar, a D-sugar, a deoxy-sugar, a dideoxy-sugar, a glucose epimer, a sugar substituted with benzyl, acetyl, halogen, amino, methyl or alloc, a uronic acid, an oligosaccharide and mixtures thereof.

9. The chlorambucil neoglycoside of claim 8, wherein the reducing sugar is selected from the group consisting of D-allose, L-allose, D-altrose, L-altrose, D-arabinose, L-arabinose, 2,3,5-O-tribenzyl-D-arabinose, D-cellobiose, D-digitoxose, D-erythrose, D-fucose, L-fucose, 2,3,4-O-tribenzyl-L-fucose, D-galactose, L-galactose, 2-deoxy-D-galactose, D-galacturonose, N-acetyl-D-galactosamine, D-glucose, L-glucose, 2-deoxy-D-glucose, 2-deoxy-2-fluoro-D-glucose, 3-deoxy-3-fluoro-D-glucose, 3-O-methyl-D-glucose, 6-amino-6-deoxy-D-glucose, 6-N-alloc-6-amino-6-deoxy-D-glucose, 6-chloro-6-deoxy-D-glucose, 6-deoxy-D-glucose, D-glucuronose, D-glucuronolactone, L-gulose, D-lyxose, L-lyxose, D-mannose, L-mannose, N-acetyl-D-mannosamine, D-Galacto-(1,4)-β-D-Mannose, D-melibiose, D-MurNAc, L-noviose, D-olivose, L-rhamnose, 2,3,4-tri-O-acetyl-L-rhamnose, D-ribose, L-ribose, 2-deoxy-D-ribose, 2-deoxy-L-ribose, 2,3,5-tri-O-benzyl-D-ribose, D-talose, L-talose, D-threose, L-threose, D-xylose, L-xylose; and mixtures thereof.

10. A composition comprising the chlorambucil neoglycoside according to claim 1 or a pharmaceutically acceptable salt thereof, combined with a pharmaceutically acceptable carrier.

11. A library of chlorambucil neoglycosides comprising two or more of the chlorambucil neoglycosides according to claim 1.

12. A method of treating cancer cells in a subject comprising the step of contacting the cancer cells in the subject with an effective amount of one or more of the chlorambucil neoglycosides according to claim 1, whereby said cancer cells are treated in the subject.

13. A method of treating cancer cells in a subject comprising the step of contacting the cancer cells in the subject with an effective amount of one or more of a chlorambucil neoglycoside having the formula:

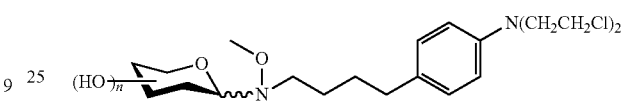

wherein

represents a reducing sugar moiety selected from the group consisting of D-allose (10), D-altrose (12), D-arabinose (14), D-fucose (20), L-fucose (21), 2-deoxy-D-glucose (30), D-glucuronose (38), D-glucuronolactone (39), L-gulose (40), D-lyxose (41), L-lyxose (42), L-ribose (54), 2-deoxy-D-ribose (55), D-threose (60), L-threose (61), D-xylose (62), and L-xylose (63); or a pharmaceutically acceptable salt thereof, whereby said cancer cells are treated in the subject.

14. The method of claim 13, wherein the reducing sugar moiety is D-arabinose (14), L-arabinose (15), D-glucuronolactone (39), D-threose (60), L-threose (61), D-xylose (62), or L-xylose (63).

15. The method of claim 14, wherein the reducing sugar is D-glucuronolactone (39) or D-threose (60).

16. The method of claim 15, wherein the reducing sugar is D-threose (60).

17. The method of claim 13, wherein the cancer cells being contacted with an effective amount of the chlorambucil neoglycoside or pharmaceutically acceptable ester, salt or prodrug thereof are selected from human lung cancer cells, human colorectal cancer cells, human liver cancer cells, human breast cancer cells, human ovarian cancer cells, and human central nervous system cancer cells.

* * * * *